US012714692B2

(12) United States Patent
Leng et al.

(10) Patent No.: US 12,714,692 B2
(45) Date of Patent: Aug. 25, 2026

(54) BACTERIAL DNA GYRASE INHIBITORS AND METHODS OF USE THEREOF

(71) Applicants: THE FLORIDA INTERNATIONAL UNIVERSITY BOARD OF TRUSTEES, Miami, FL (US); UNIVERSITY OF CENTRAL FLORIDA RESEARCH FOUNDATION, INC., Orlando, FL (US)

(72) Inventors: Fenfei Leng, Palmetto Bay, FL (US); Eddy Alfonso, Miami, FL (US); Zifang Deng, Miami, FL (US); Adel Nefzi, Miami, FL (US); Kyle Rohde, Orlando, FL (US)

(73) Assignees: THE FLORIDA INTERNATIONAL UNIVERSITY BOARD OF TRUSTEES, Miami, FL (US); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 534 days.

(21) Appl. No.: 18/139,681

(22) Filed: Apr. 26, 2023

(65) Prior Publication Data

US 2023/0364057 A1 Nov. 16, 2023

Related U.S. Application Data

(60) Provisional application No. 63/334,868, filed on Apr. 26, 2022.

(51) Int. Cl.

| | |
|---|---|
| ***A61K 31/381*** | (2006.01) |
| ***A61K 31/122*** | (2006.01) |
| ***A61K 31/136*** | (2006.01) |
| ***A61K 31/137*** | (2006.01) |
| ***A61K 31/15*** | (2006.01) |
| ***A61K 31/164*** | (2006.01) |
| ***A61K 31/192*** | (2006.01) |
| ***A61K 31/195*** | (2006.01) |
| ***A61K 31/196*** | (2006.01) |
| ***A61K 31/197*** | (2006.01) |
| ***A61K 31/24*** | (2006.01) |
| ***A61K 31/345*** | (2006.01) |
| ***A61K 31/351*** | (2006.01) |
| ***A61K 31/352*** | (2006.01) |
| ***A61K 31/357*** | (2006.01) |

(Continued)

(52) U.S. Cl.

CPC .......... *A61K 31/404* (2013.01); *A61K 31/122* (2013.01); *A61K 31/136* (2013.01); *A61K 31/137* (2013.01); *A61K 31/15* (2013.01); *A61K 31/164* (2013.01); *A61K 31/192* (2013.01); *A61K 31/195* (2013.01); *A61K 31/196* (2013.01); *A61K 31/197* (2013.01); *A61K 31/24* (2013.01); *A61K 31/345* (2013.01); *A61K 31/351* (2013.01); *A61K 31/352* (2013.01); *A61K 31/357* (2013.01); *A61K 31/365* (2013.01); *A61K 31/366* (2013.01); *A61K 31/381* (2013.01); *A61K 31/41* (2013.01); *A61K 31/4155* (2013.01); *A61K 31/4162* (2013.01); *A61K 31/4178* (2013.01); *A61K 31/4184* (2013.01); *A61K 31/422* (2013.01); *A61K 31/4245* (2013.01); *A61K 31/426* (2013.01); *A61K 31/427* (2013.01); *A61K 31/428* (2013.01); *A61K 31/429* (2013.01); *A61K 31/433* (2013.01); *A61K 31/436* (2013.01); *A61K 31/4365* (2013.01); *A61K 31/437* (2013.01); *A61K 31/438* (2013.01); *A61K 31/4402* (2013.01); *A61K 31/443* (2013.01); *A61K 31/4436* (2013.01); *A61K 31/4439* (2013.01); *A61K 31/45* (2013.01); *A61K 31/47* (2013.01); *A61K 31/473* (2013.01); *A61K 31/4745* (2013.01); *A61K 31/48* (2013.01); *A61K 31/496* (2013.01); *A61K 31/498* (2013.01); *A61K 31/502* (2013.01); *A61K 31/513* (2013.01); *A61K 31/515* (2013.01); *A61K 31/517* (2013.01); *A61K 31/519* (2013.01); *A61K 31/53* (2013.01); *A61K 31/5377* (2013.01); *A61K 31/538* (2013.01); *A61K 31/635* (2013.01); *A61K 31/7076* (2013.01); *A61P 31/04* (2018.01)

(58) Field of Classification Search

None

See application file for complete search history.

(56) References Cited

U.S. PATENT DOCUMENTS

2018/0256674 A1* 9/2018 Jeon .................... A61K 9/0014

OTHER PUBLICATIONS

Cleveland Clinic. Antiobiotics. Retreived from the internet on Sep. 22, 2025, https://my.clevelandclinic.org/health/treatments/16386-antibiotics (Year: 2025).*

(Continued)

*Primary Examiner* — Lauren Wells

(74) *Attorney, Agent, or Firm* — SALIWANCHIK, LLOYD & EISENSCHENK

(57) ABSTRACT

The subject invention provides fluorophore-quencher nucleic acid molecules comprising relaxed or supercoiled DNA molecules, and their use in rapid and efficient high-throughput screening (HTS) assays to screen and identify compounds that inhibit DNA gyrases. These compounds can be used as antibiotics for treating bacterial infections, especially, multidrug resistant bacterial infections.

15 Claims, 52 Drawing Sheets

(51) Int. Cl.

| | |
|---|---|
| ***A61K 31/365*** | (2006.01) |
| ***A61K 31/366*** | (2006.01) |
| ***A61K 31/404*** | (2006.01) |
| ***A61K 31/41*** | (2006.01) |
| ***A61K 31/4155*** | (2006.01) |
| ***A61K 31/4162*** | (2006.01) |
| ***A61K 31/4178*** | (2006.01) |
| ***A61K 31/4184*** | (2006.01) |
| ***A61K 31/422*** | (2006.01) |
| ***A61K 31/4245*** | (2006.01) |
| ***A61K 31/426*** | (2006.01) |
| ***A61K 31/427*** | (2006.01) |
| ***A61K 31/428*** | (2006.01) |
| ***A61K 31/429*** | (2006.01) |
| ***A61K 31/433*** | (2006.01) |
| ***A61K 31/436*** | (2006.01) |
| ***A61K 31/4365*** | (2006.01) |
| ***A61K 31/437*** | (2006.01) |
| ***A61K 31/438*** | (2006.01) |
| ***A61K 31/4402*** | (2006.01) |
| ***A61K 31/443*** | (2006.01) |
| ***A61K 31/4436*** | (2006.01) |
| ***A61K 31/4439*** | (2006.01) |
| ***A61K 31/45*** | (2006.01) |
| ***A61K 31/47*** | (2006.01) |
| ***A61K 31/473*** | (2006.01) |
| ***A61K 31/4745*** | (2006.01) |
| ***A61K 31/48*** | (2006.01) |
| ***A61K 31/496*** | (2006.01) |
| ***A61K 31/498*** | (2006.01) |
| ***A61K 31/502*** | (2006.01) |
| ***A61K 31/513*** | (2006.01) |
| ***A61K 31/515*** | (2006.01) |
| ***A61K 31/517*** | (2006.01) |
| ***A61K 31/519*** | (2006.01) |
| ***A61K 31/53*** | (2006.01) |
| ***A61K 31/5377*** | (2006.01) |
| ***A61K 31/538*** | (2006.01) |
| ***A61K 31/635*** | (2006.01) |
| ***A61K 31/7076*** | (2006.01) |
| ***A61P 31/04*** | (2006.01) |

(56) References Cited

OTHER PUBLICATIONS

Frieri et al. Antibiotic resistance, Journal of Infection and Public Health, vol. 10, Issue 4, 2017. (Year: 2017).*

May et al. The Antiobiotic Novobiocin Binds and Activates the ATPase That Powers Lipopolysaccharide Transport. Journal of the American Chemical Society, vol. 139, Issue 48. Published 2017. (Year: 2017).*

CAS STNext. Registry File. Registry No. 134391-43-9. Published 2008. Retrieved from the Internet on Feb. 18, 2026, www.stn.org. (Year: 2008).*

Alfonso, Eddy E. et al. “Potent Inhibition of Bacterial DNA Gyrase by Digallic Acid and Other Gallate Derivatives.” ChemMedChem 17(23):1-8, (Year: 2022).

Alfonso, Eddy E. et al. “Novel and Structurally Diversified Bacterial DNA Gyrase Inhibitors Discovered through a Fluorescence-Based High-Throughput Screening Assay.” ACS Pharmacology & Translational Science, 5(10):932-944, (Year: 2022).

* cited by examiner

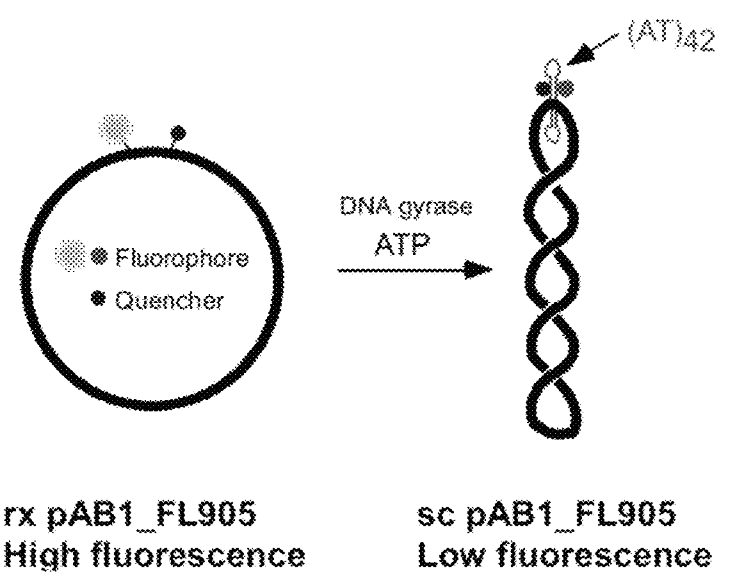
FIG. 1
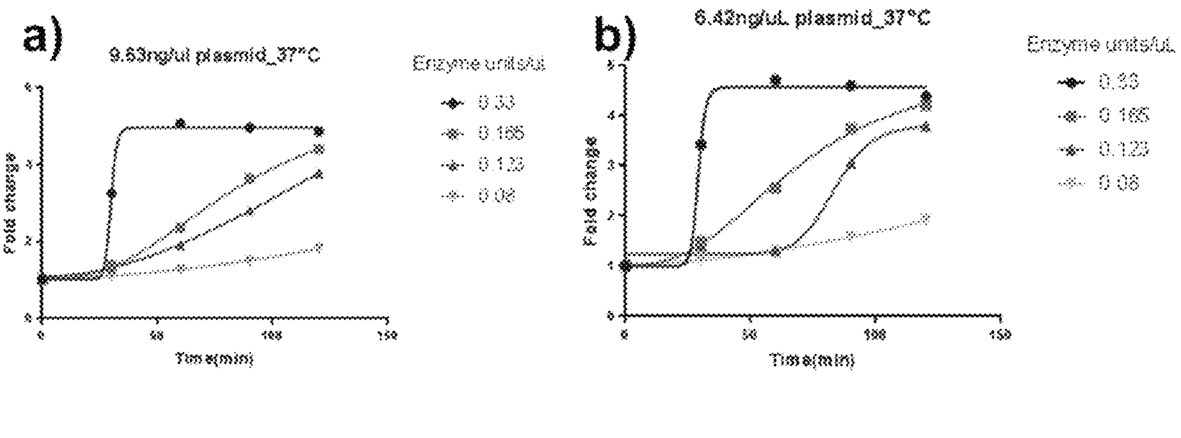
FIG. 2A
FIG. 2B

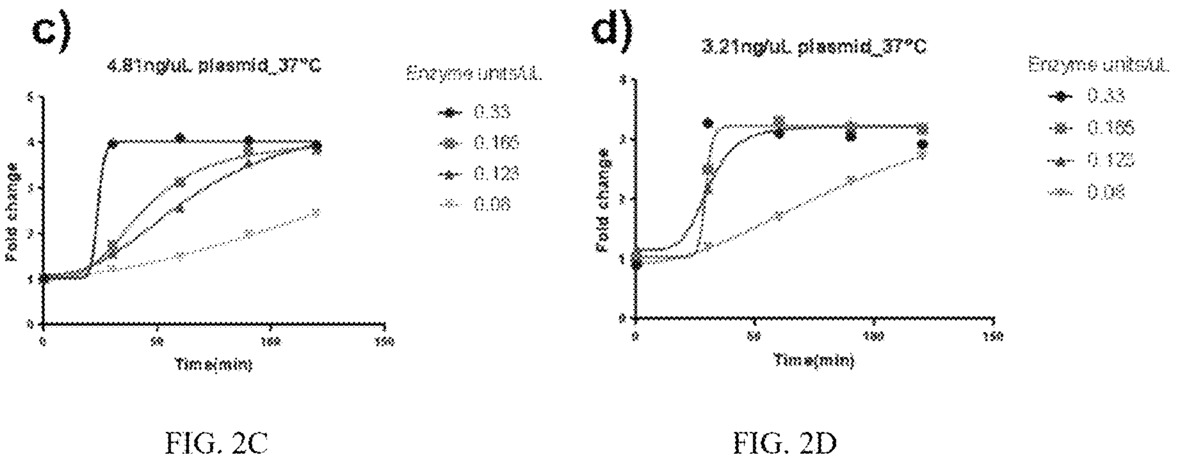
FIG. 2C
FIG. 2D
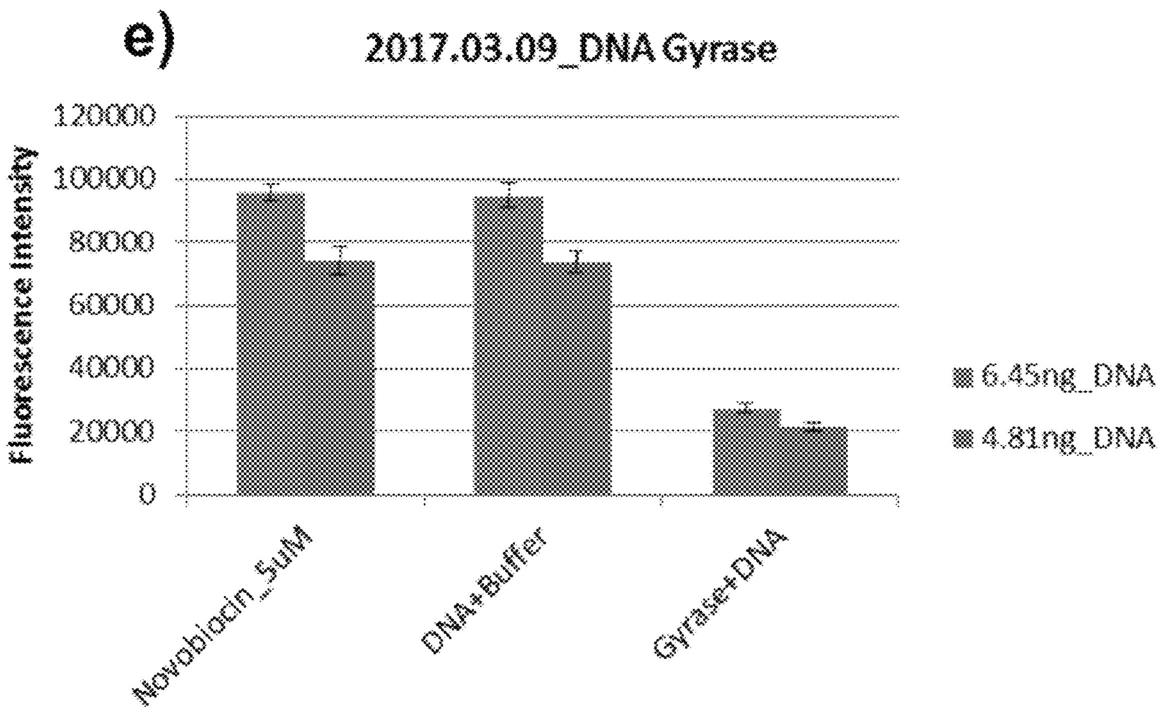
FIG. 2E c)

| Pos Control | 812525 +- 15302 | Signal/Background | 2.4 | Z Factor | 0.738 |
|---|---|---|---|---|---|
| Neg Control | 338057 +- 26067 | Signal/Noise | 18.2 | Signal Window | 22.9 |

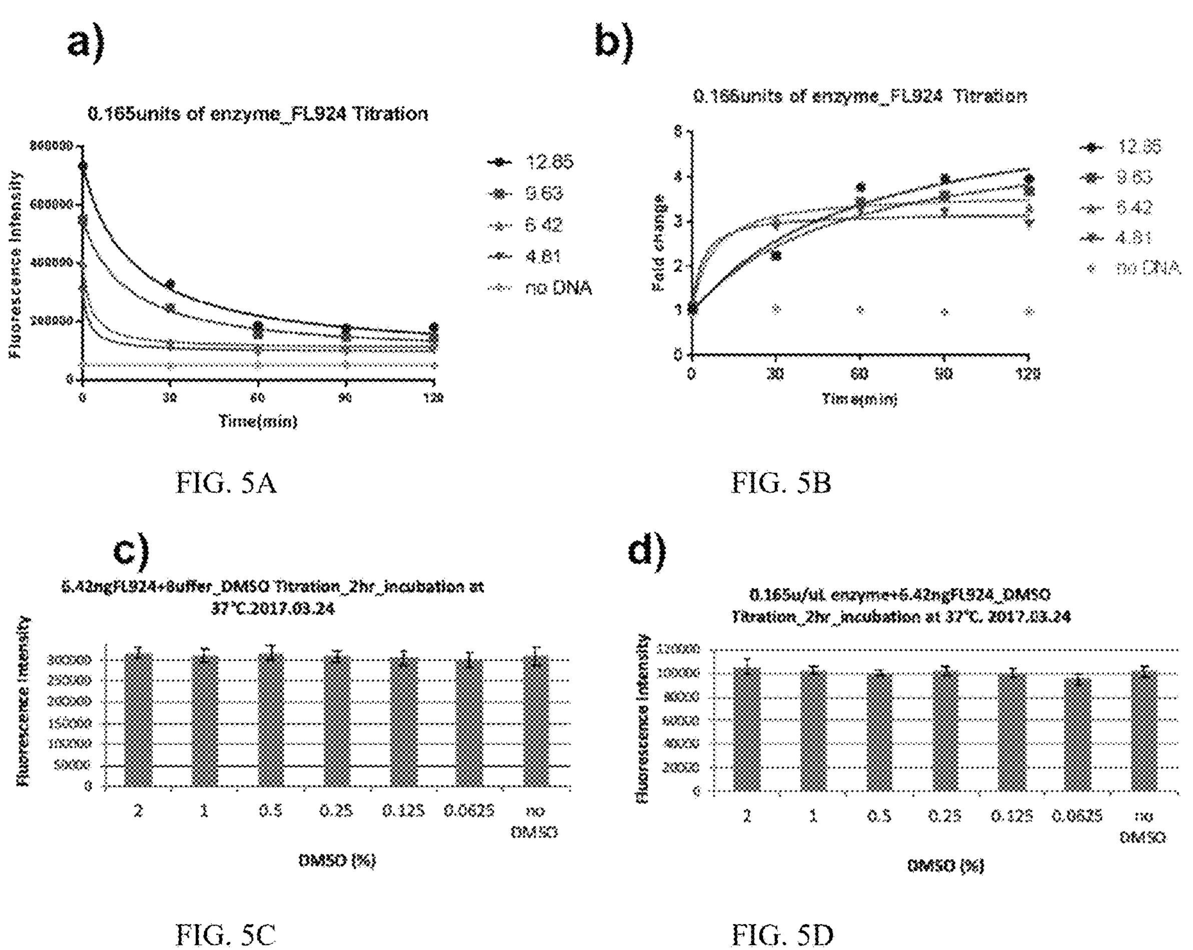
FIG. 5A
FIG. 5B
FIG. 5C
FIG. 5D
e) Novobiocin Titration
0.165units of enzyme/uL + 6.425ng/uL of FL-924
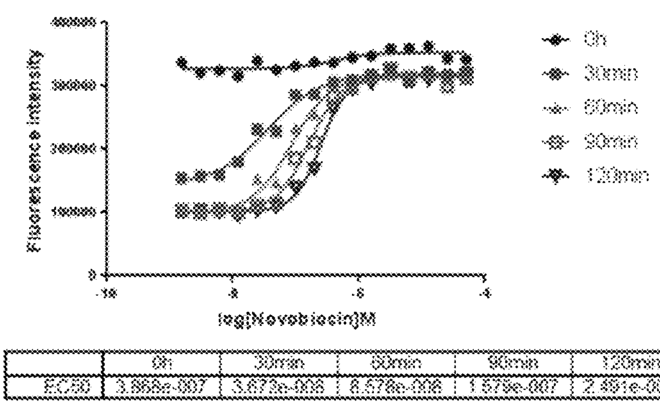
| | 0h | 30min | 60min | 90min | 120min |
|---|---|---|---|---|---|
| EC50 | 3.868e-007 | 3.672e-008 | 6.578e-008 | 1.579e-007 | 2.491e-007 |
FIG. 5E

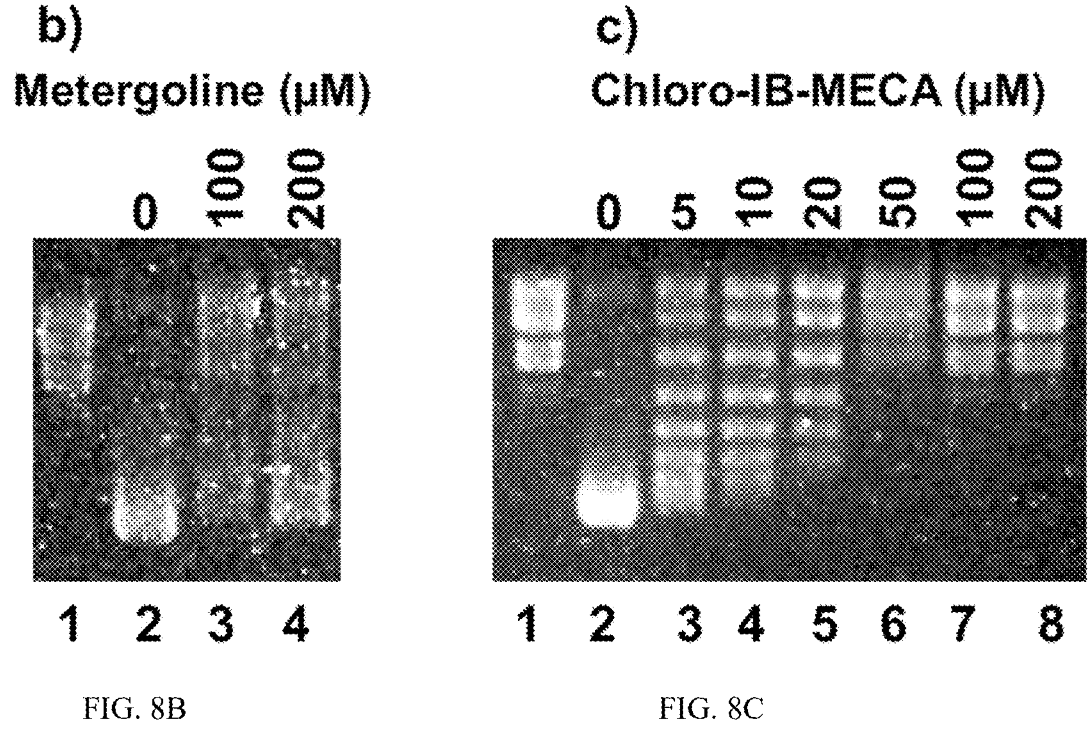
FIG. 8B
FIG. 8C
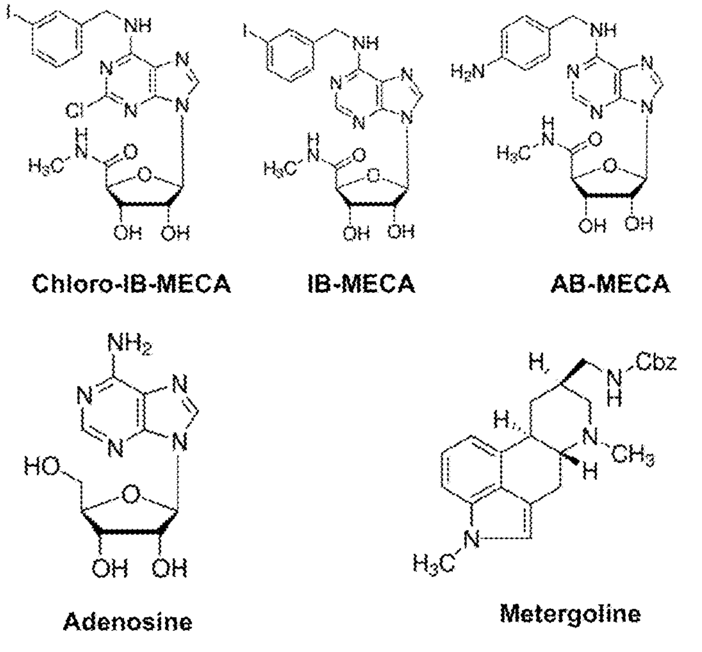
Chloro-IB-MECA IB-MECA AB-MECA
Adenosine Metergoline
FIG. 9

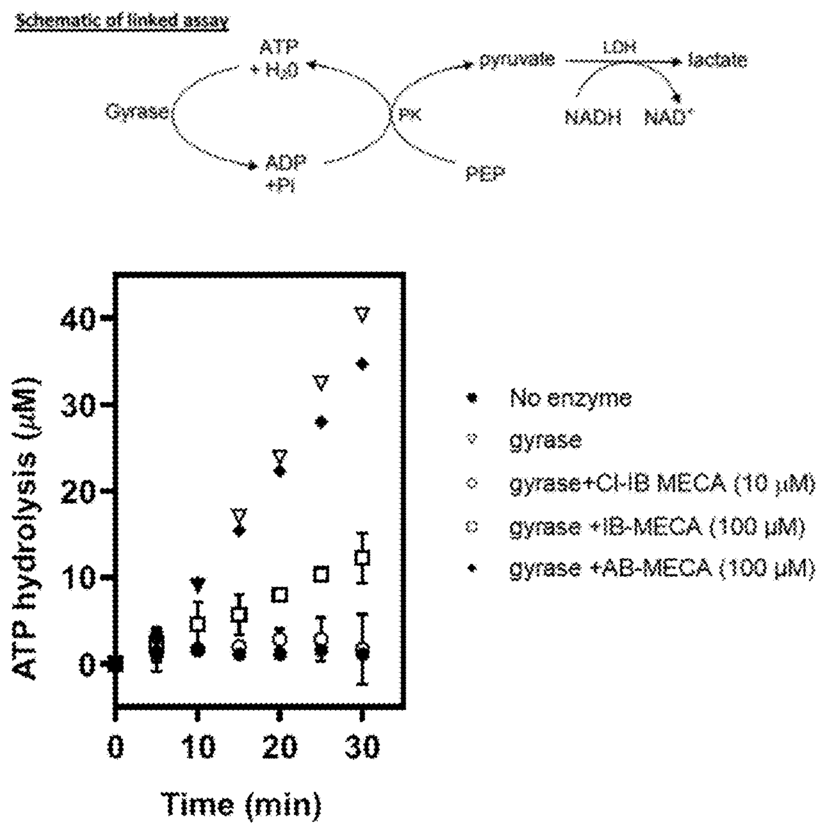
FIG. 11
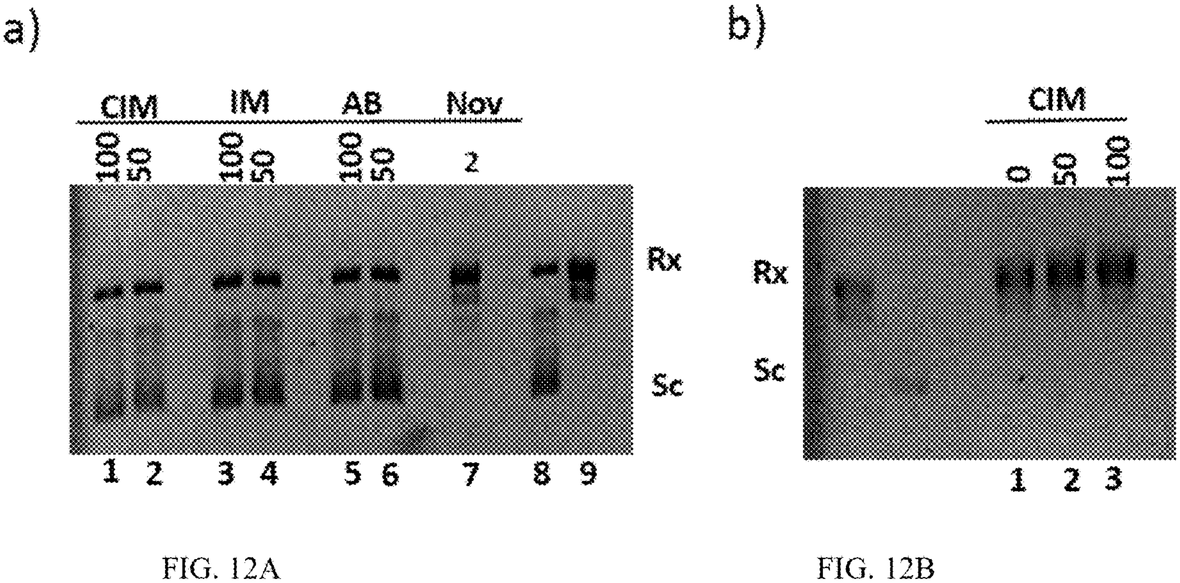
FIG. 12A
FIG. 12B

Clorobiocin
1 bithiazoles

Novobiocin
2

Ciprofloxacin

Echinomycin 9-aminoacridine

Pyronine Y

Clofazimine

Anthracenyl

Ethacridine

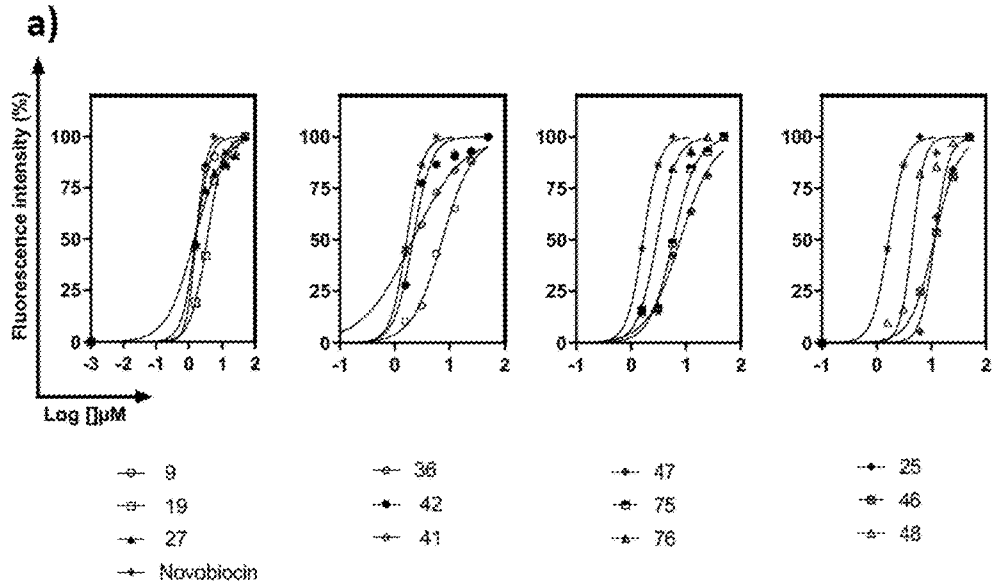
FIG. 26A
b)
| Compound # | IC50 (μM) |
|---|---|
| 9 | 1.69 |
| 19 | 3.55 |
| 25 | 10.62 |
| 27 | 1.74 |
| 36 | 7.421 |
| 41 | 1.48 |
| 42 | 2.18 |
| 46 | 11.23 |
| 47 | 1.87 |
| 48 | 4.28 |
| 75 | 5.28 |
| 76 | 2.53 |
| Novobiocin | 1.85 |
FIG. 26B
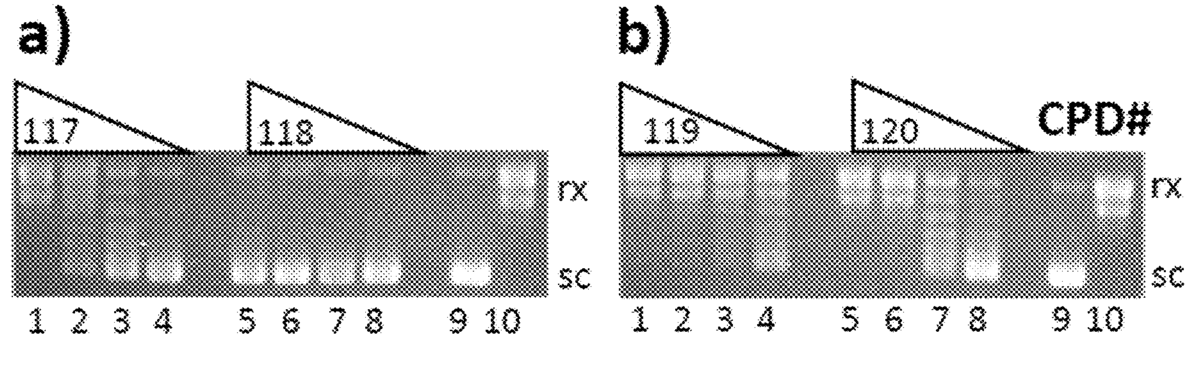
FIG. 27A
FIG. 27B

| Compound | $IC_{50}$ (µM) | MIC µM | |
|---|---|---|---|
| | | *S.aureus* | MRSA |
| 48 | 4.2 | 3.125 | 3.125 |
| 125 | 4.929 | N | N |
| 124 | 5.549 | 1.56 | 1.56 |
| 119 | 7.71 | 0.78 | 0.78 |
| 120 | 7.85 | 1.56 | 1.56 |
| 46 | 11.43 | N | N |
| 25 | 11.48 | N | N |
| 117 | 15.72 | 1.56 | 1.56 |
| 121 | 28.01 | 3.125 | 3.125 |
| 123 | 28.16 | 1.56 | 1.56 |
| 118 | N/A | N | N |
| 122 | N/A | N | N |

48

$IC_{50}$ = 4.2 µM

46

$IC_{50}$ = 11.43 µM

120

$IC_{50}$ = 7.85 µM

25

$IC_{50}$ = 11.48 µM 118 117 48

$IC_{50} > 200\ \mu M$ $IC_{50} = 15.72\ \mu M$ $IC_{50} = 4.2\ \mu M$ 123 120 48

IC50 = 28.16 μM IC50 = 7.85 μM IC50 = 4.2 μM

122
IC50 > 200 µM

121
IC50 = 28.01 µM

119
$IC_{50}$ = 7.71 µM

124
$IC_{50}$ = 5.5 µM

125
IC50 =4.9 µM

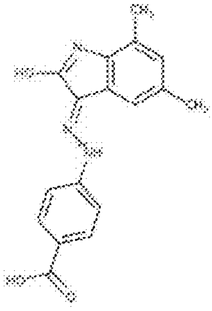
9
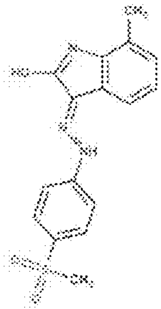
109
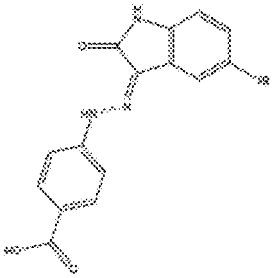
111
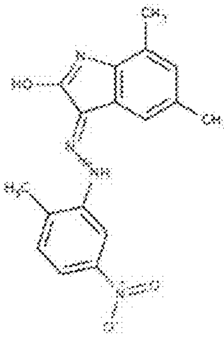
114
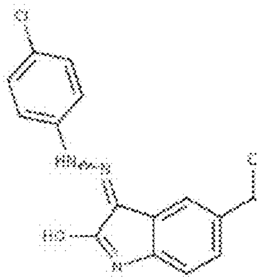
115
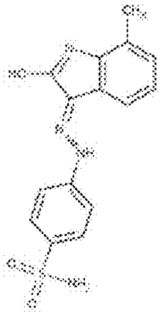
116
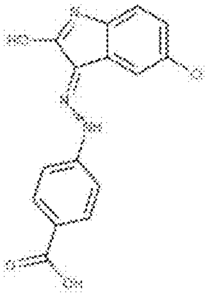
126
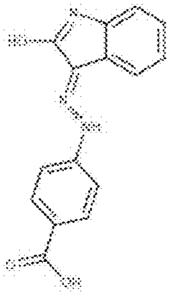
127
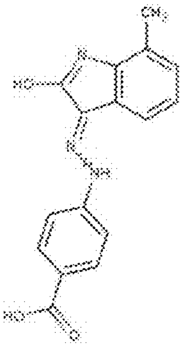
128
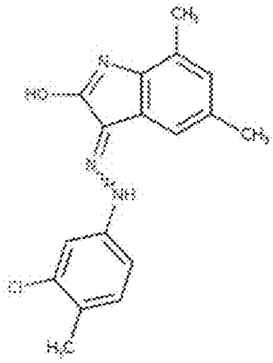
132
FIG. 33
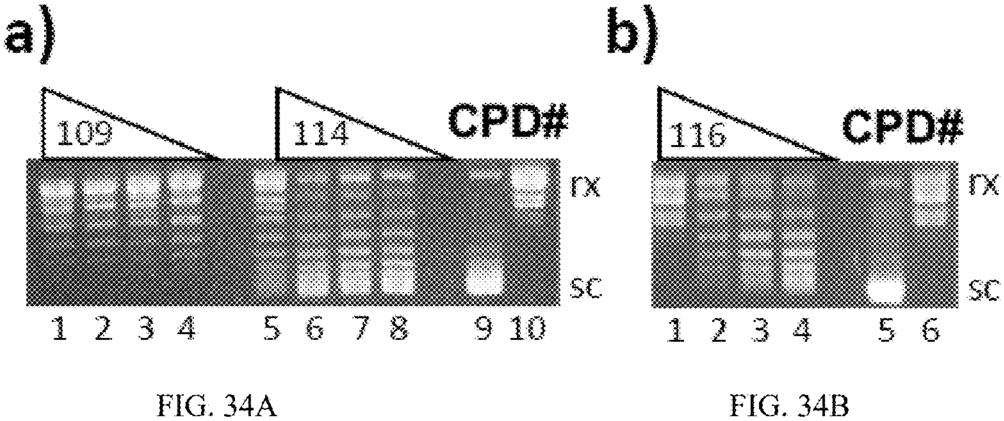
FIG. 34A
FIG. 34B

| Compound | IC50 (μM) | MIC (μM) | |
|---|---|---|---|
| | | *S.aureus* | MRSA |
| 9 | 1.609 | 3.125 | 3.125 |
| 109 | 2.317 | N | N |
| 114 | 26.96 | N | N |
| 115 | 35 | N | N |
| 116 | 10.28 | N | N |
| 126 | 6.193 | 100 | 100 |
| 127 | 11.67 | 50 | 50 |
| 128 | 2.507 | 50 | 50 |
| 132 | 27.7 | N | N |

2,6,7-Trihydroxy-9-methylxanthen-3-one

CPD #75

Rhein CPD #82

Emodin

CPD #242

Erythrosin B

CPD #253

Alizarin

CPD #256 variamycin

NSC219148

CPD #225

CPD83 CPD106 CPD136 CPD137

CPD138 CPD139 CPD140

CPD141 CPD142 CPD143

CPD144 CPD145 CPD146

N-(6-chloro-4-phenylquinazolin-2-yl)guanidine

CPD#154
IC50=3.13 μM
DSDB

1-[(4-carbamoylphenyl)carbamoyl]ethyl 1,4-dihydroxynaphthalene-2-carboxylate

CPD #40
NK and DSDB

3-[(4-[(2-carboxyethyl)amino]-9,10-dioxo-9,10-dihydroanthracen-1-yl)amino]propanoic acid

CPD#173
NK

7-((2-(3,5-Dibromo-4-hydroxyphenyl)ethyl)amino)-5,8-quinolinedione

NSC668394

CPD #232
NK

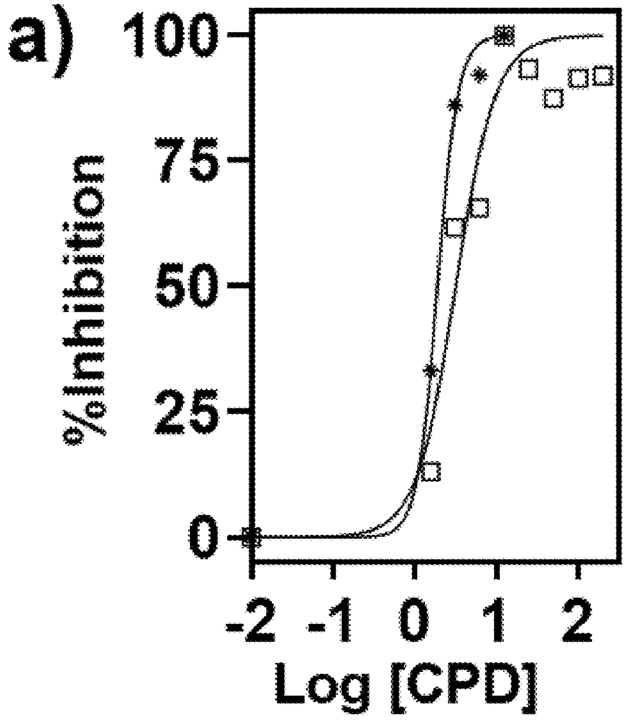
FIG. 39A
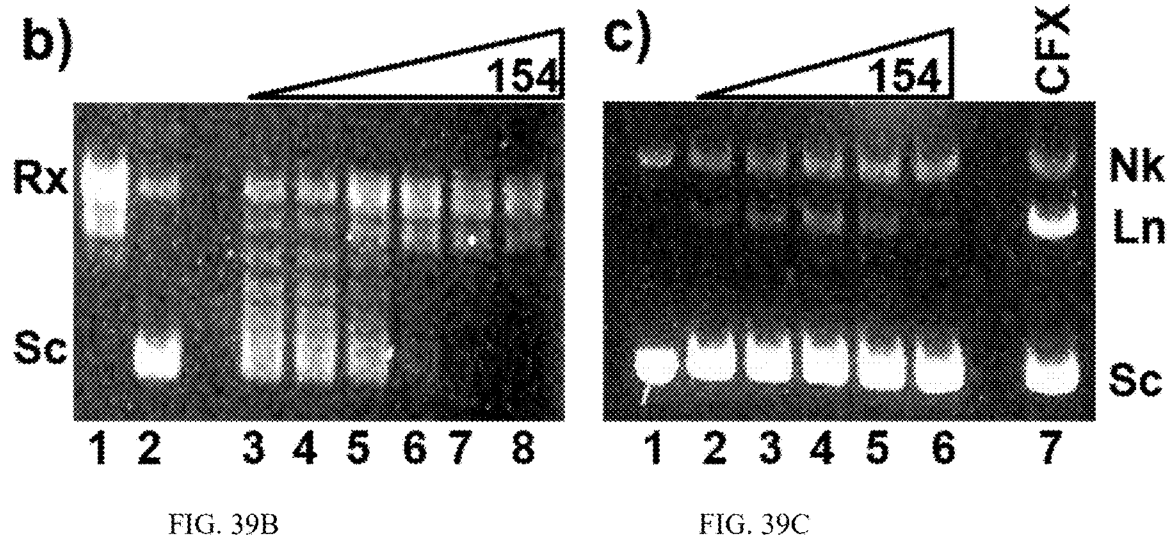
FIG. 39B
FIG. 39C

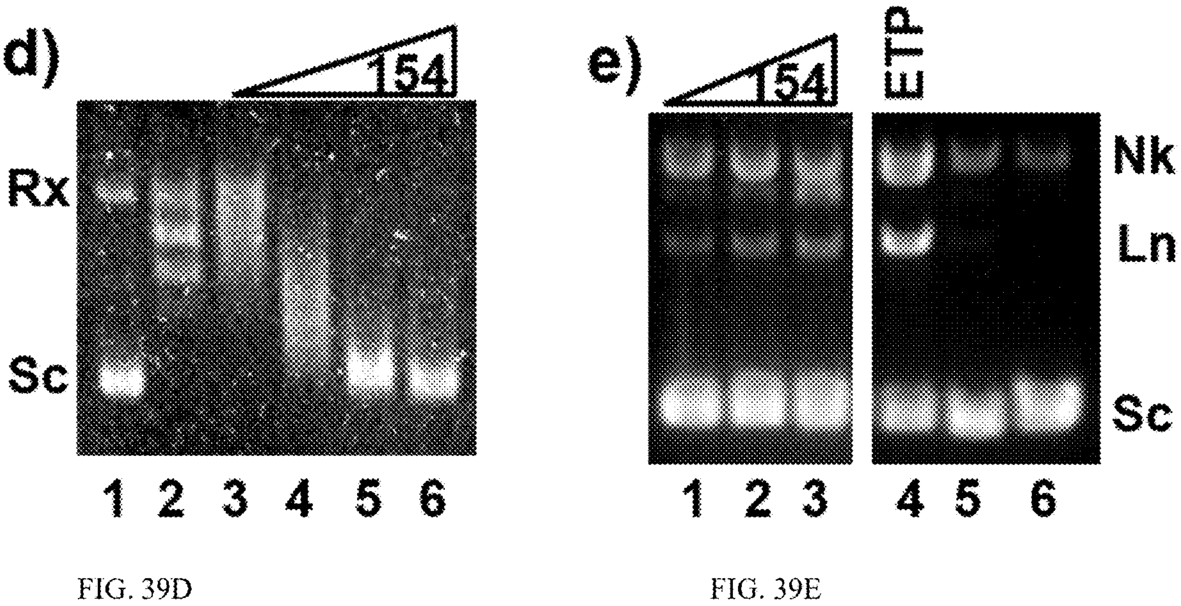
FIG. 39D
FIG. 39E
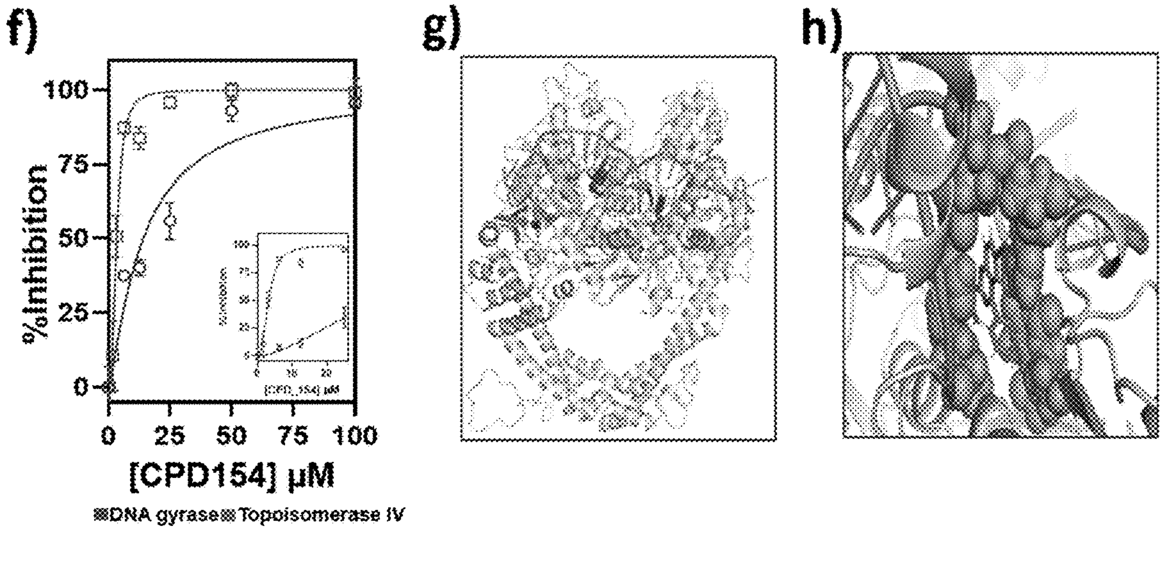
FIG. 39F
FIG. 39G
FIG. 39H

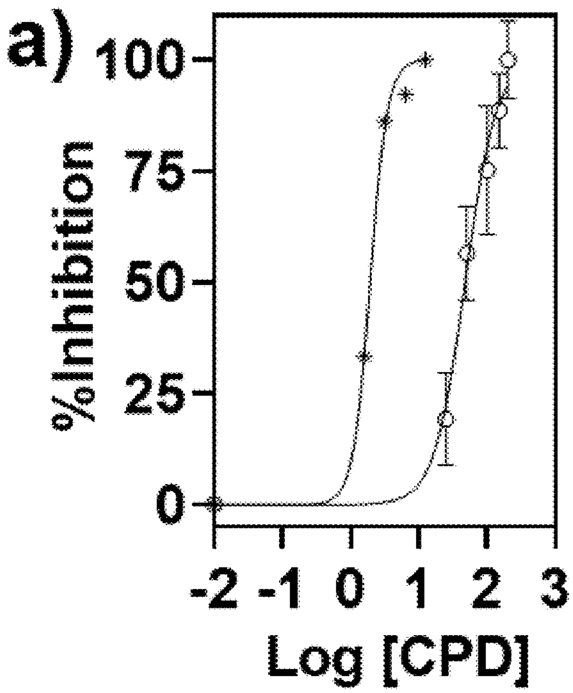
FIG. 40A
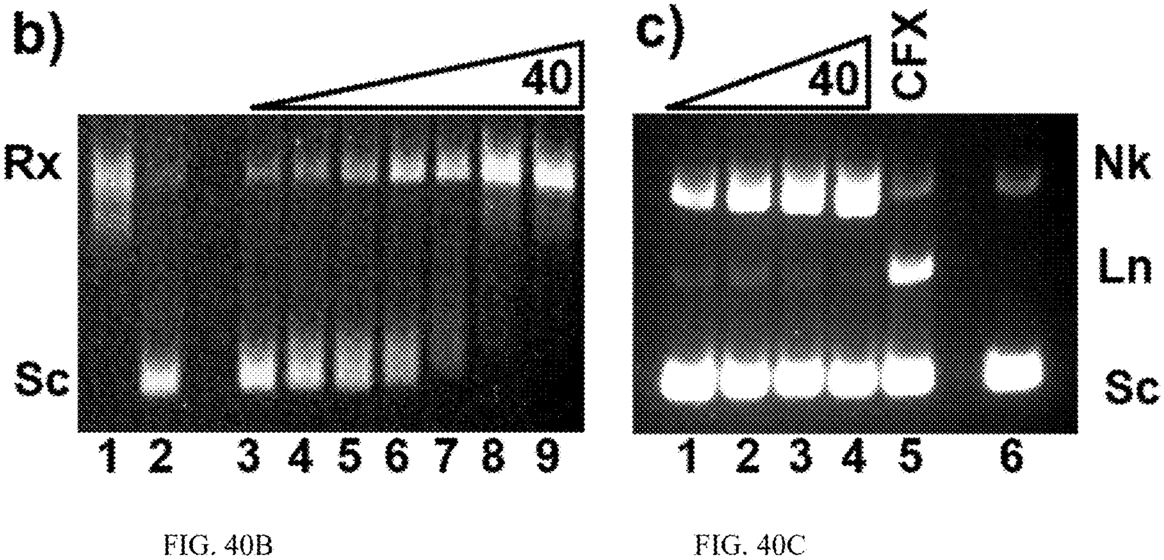
FIG. 40B
FIG. 40C a

IC50, 2.1 μM b

IC50 > 200 μM c

IC50, 26 μM d

IC50, 13.8 μM e

IC50, 100 μM f

IC50, 18.8 μM

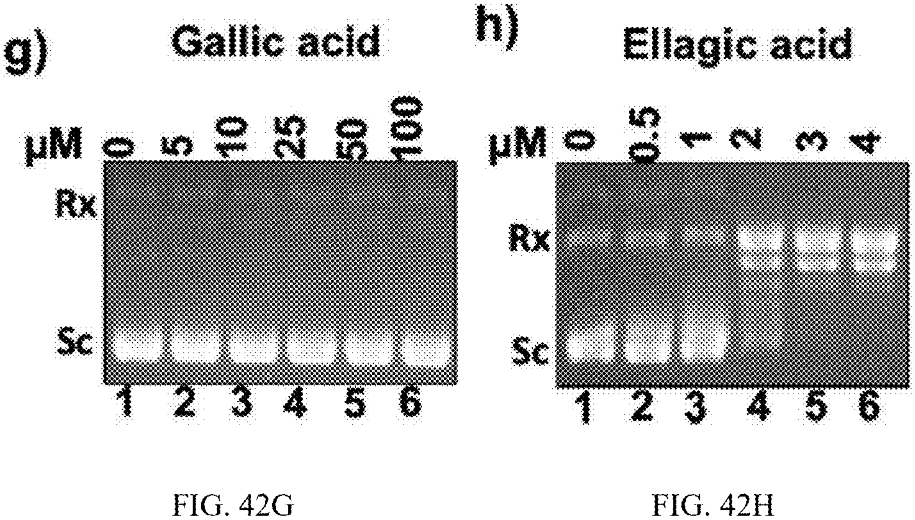
FIG. 42G
FIG. 42H
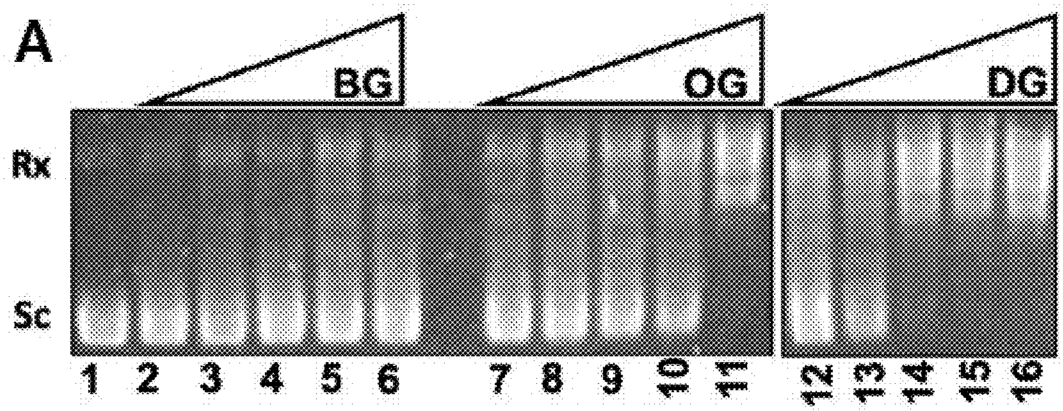
FIG. 43A
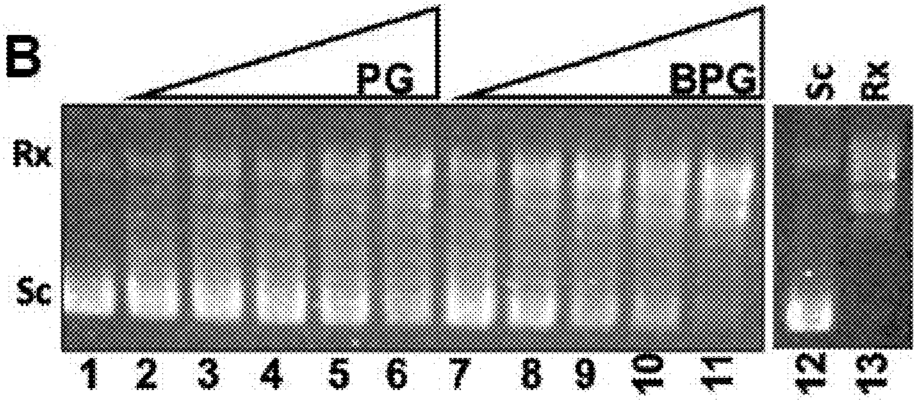
FIG. 43B

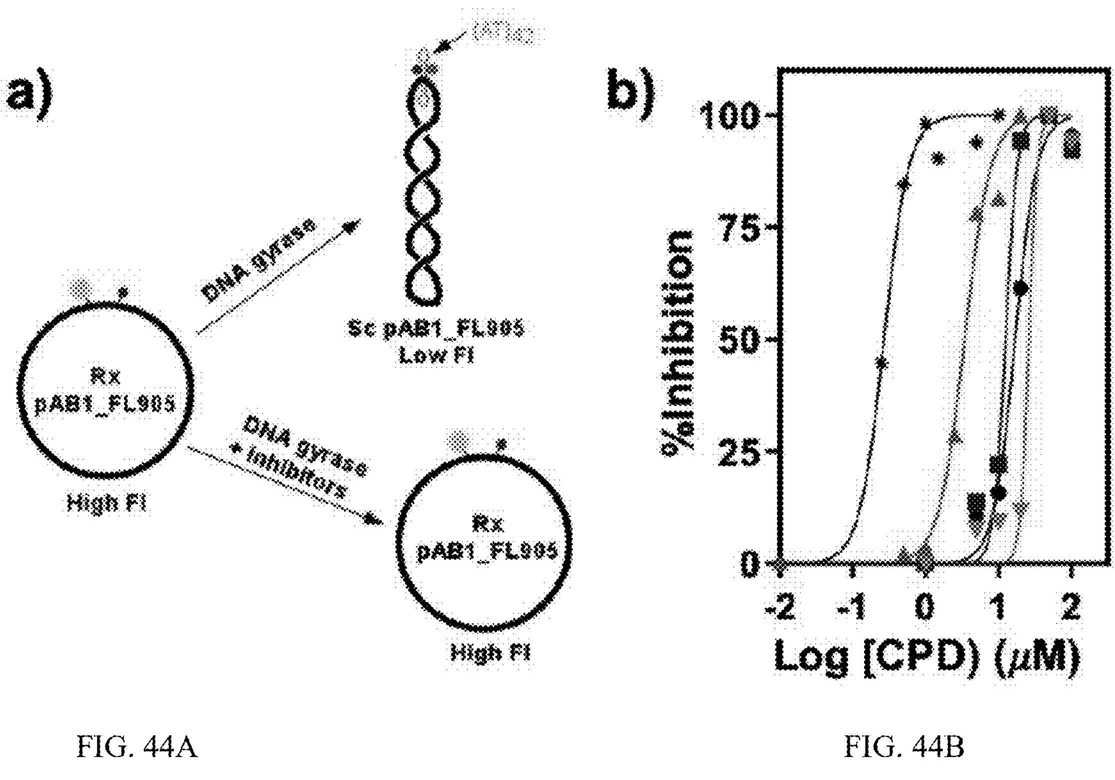
FIG. 44A
FIG. 44B
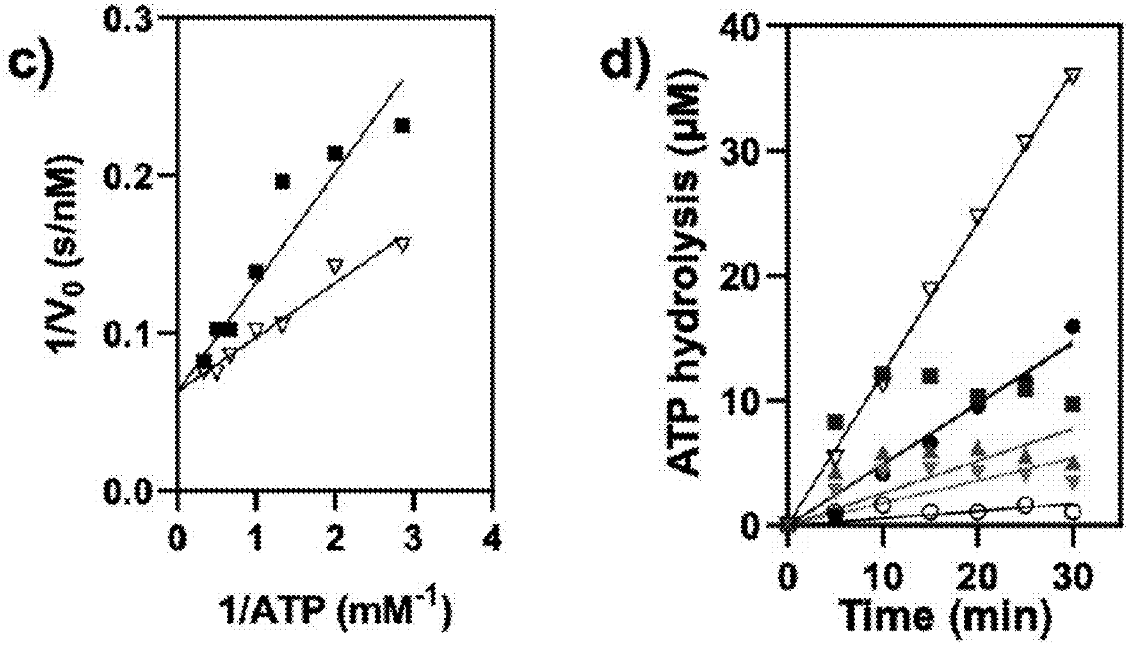
FIG. 44C
FIG. 44D

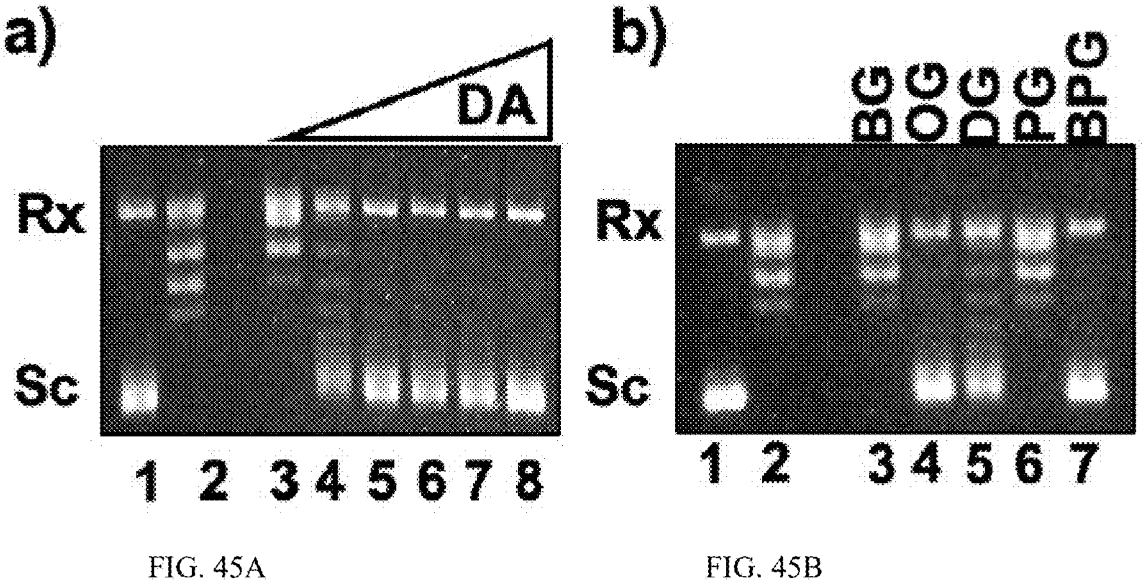
FIG. 45A
FIG. 45B
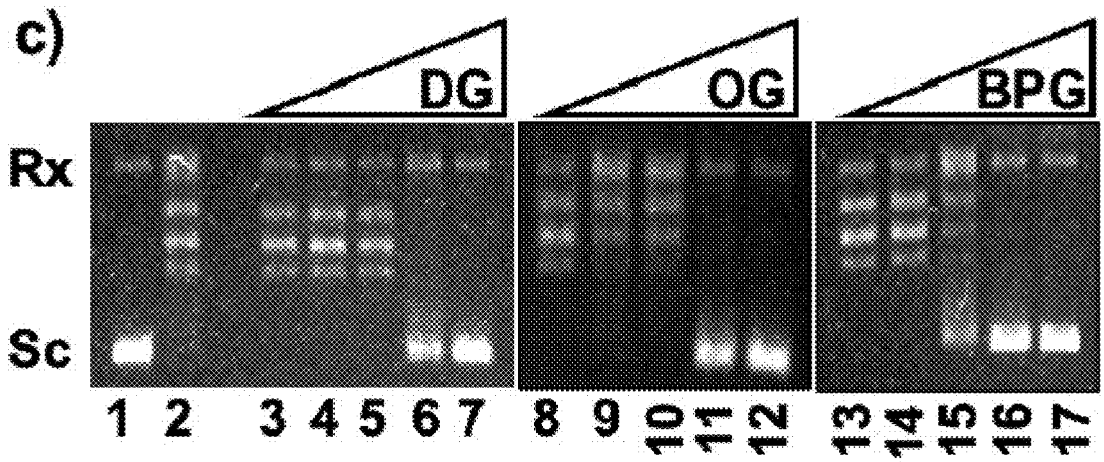
FIG. 45C

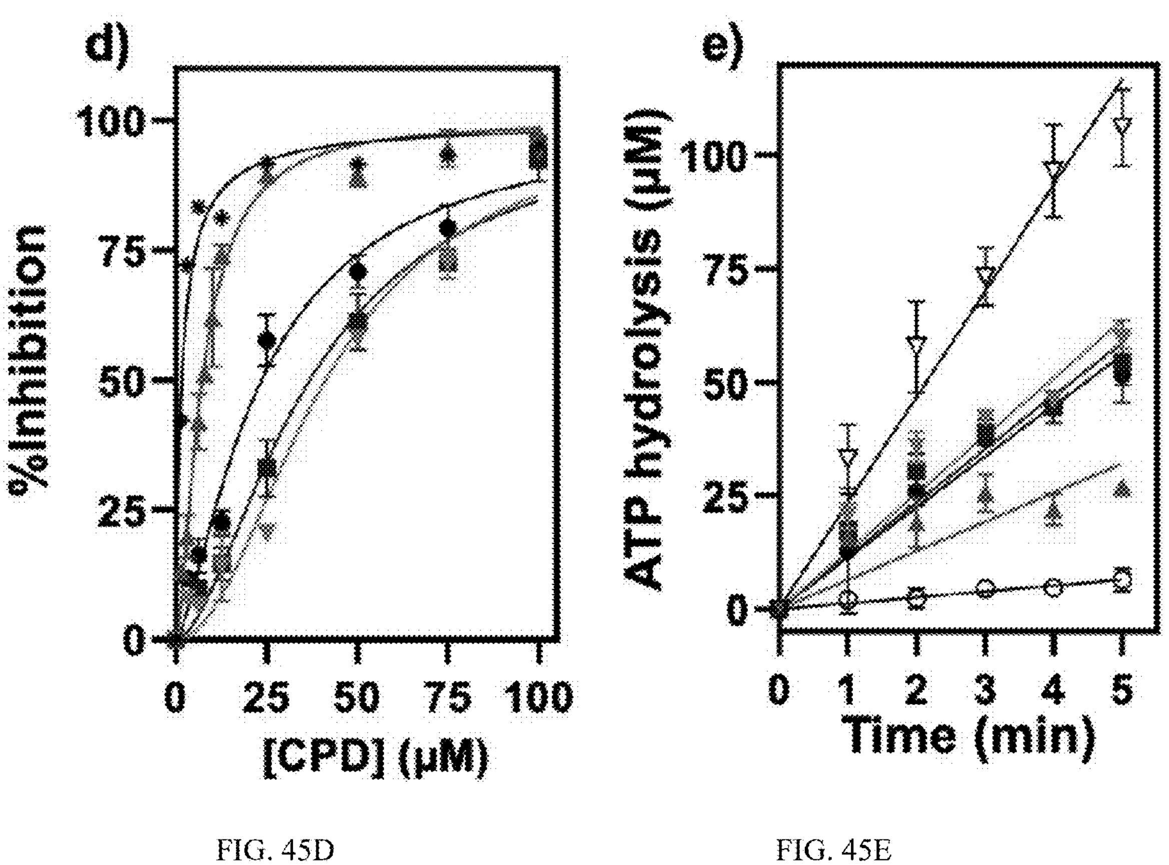
FIG. 45D
FIG. 45E
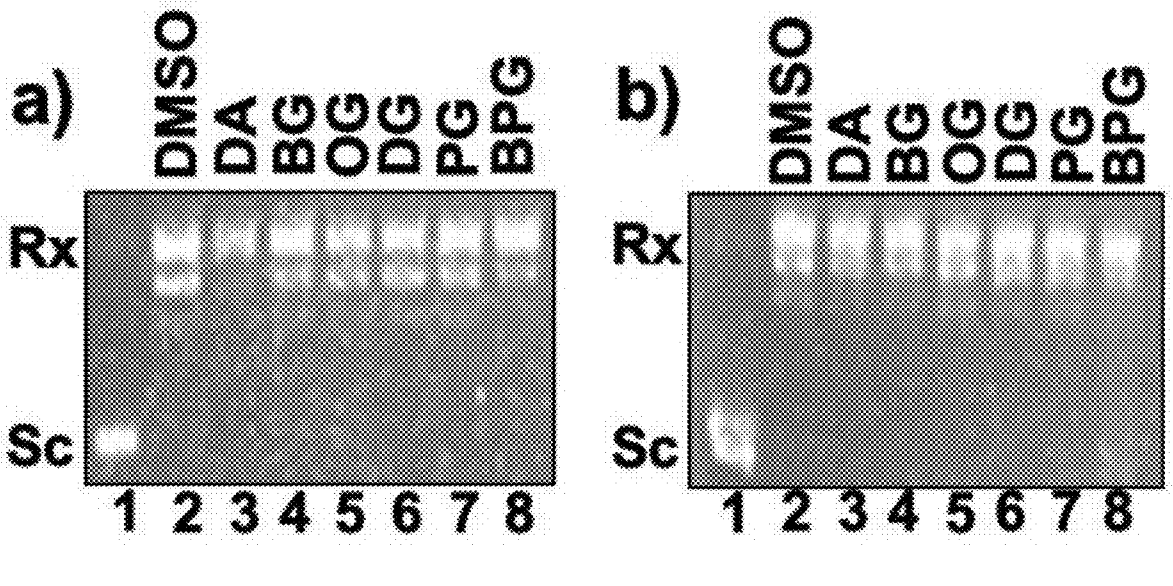
FIG. 46A
FIG. 46B

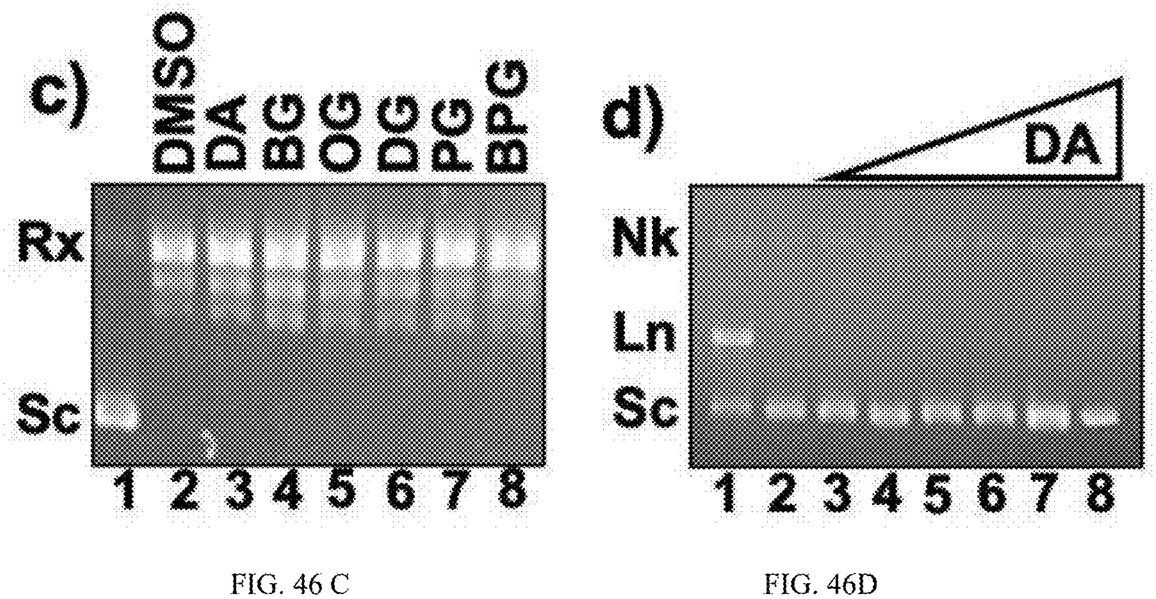
FIG. 46 C
FIG. 46D
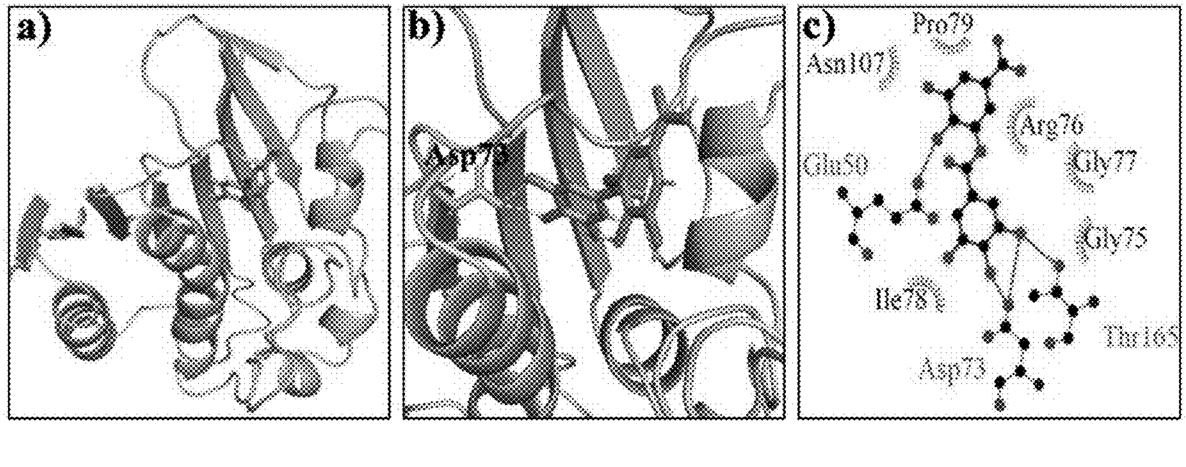
FIG. 47A
FIG. 47B
FIG. 47C

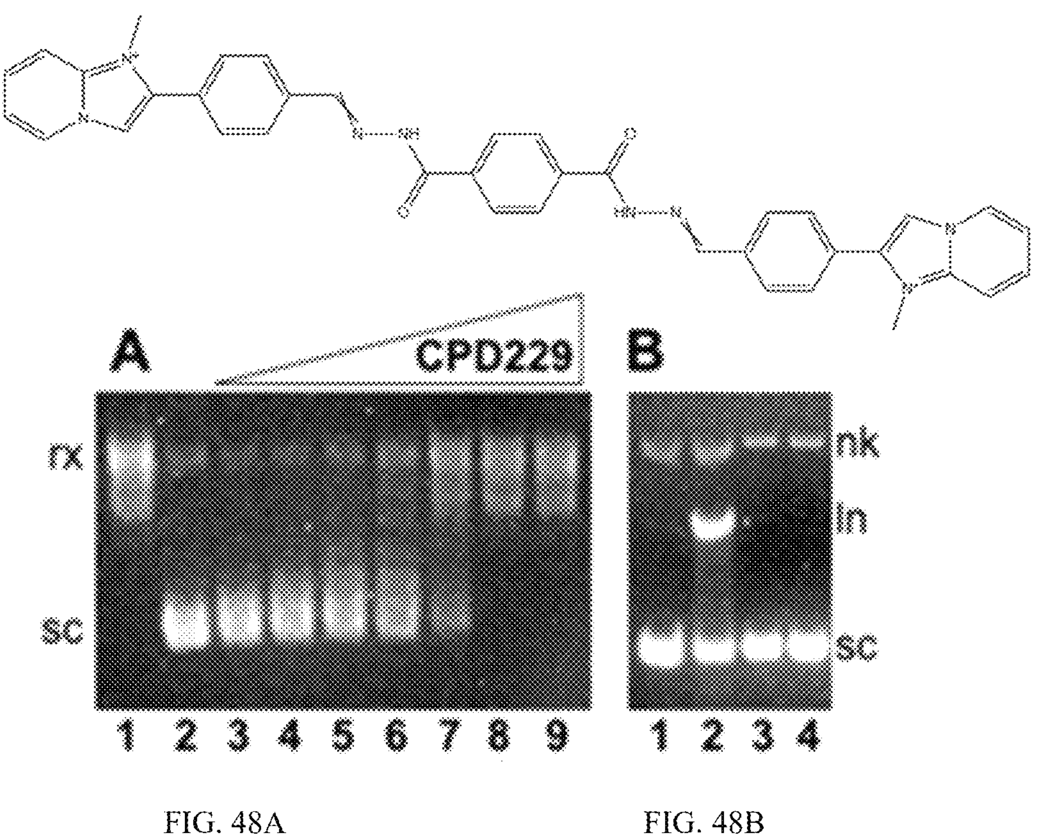
FIG. 48A
FIG. 48B
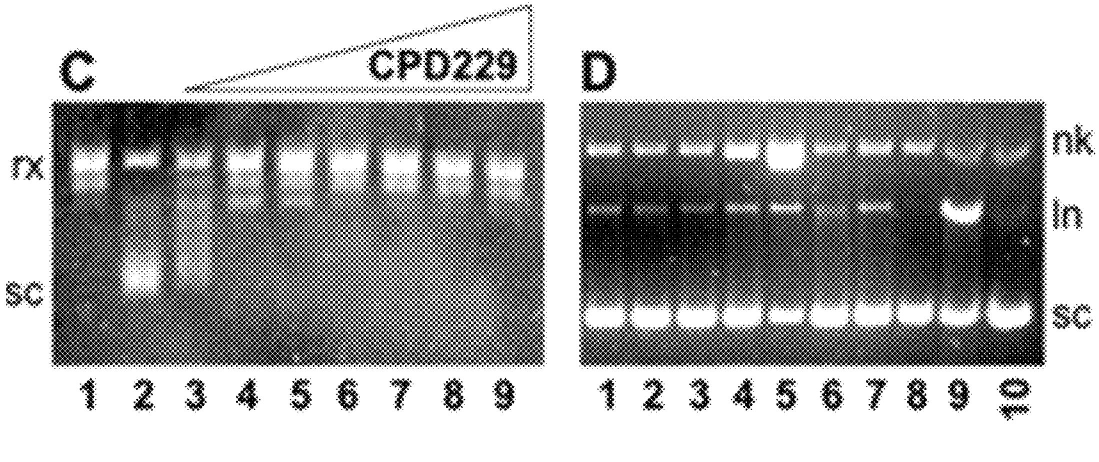
FIG. 48C
FIG. 48D

BACTERIAL DNA GYRASE INHIBITORS AND METHODS OF USE THEREOF

CROSS-REFERENCE TO RELATED APPLICATION

This application claims the benefit of U.S. Provisional Application Ser. No. 63/334,868 filed Apr. 26, 2022, which is hereby incorporated by reference herein in its entirety.

GOVERNMENT SUPPORT

The subject invention was made with government support under AI125973 awarded by the National Institutes of Health. The government has certain rights in the invention.

BACKGROUND OF THE INVENTION

Tuberculosis (TB), a communicable disease caused by *Mycobacterium tuberculosis* (Mtb), was the world's deadliest disease from a single infectious agent prior to the COVID-19 pandemic. In 2020, about 10 million people developed TB and 1.5 million died. The COVID 19 pandemic has reversed years of progress in efforts to reduce the global impact of TB, with WHO estimating that 400,000 more people died from TB in 2020.

The steady rise of drug-resistant TB is a serious global public health concern. In 2019, about half a million TB patients developed rifampicin-resistant TB (RR-TB), of which approximately 400,000 had multidrug-resistant TB (MDR-TB). Additionally, there are also reports of nonresponsive Totally Drug-Resistant TB (TDR-TB). Treatment success declines rapidly with increasing drug resistance. In fact, XDR-TB and TDR-TB are not treatable and result in 100% mortality.

The alarming increase of drug resistant TB requires the discovery and development of new classes of TB drugs that are effective against the difficult to treat MDR-, XDR-, and TDR-TB. In addition to heritable drug resistance from genetic mutations, in vivo growth conditions can contribute to treatment failure by inducing phenotypic drug tolerance. Conditions within macrophages and within the granuloma (e.g., hypoxia, low pH) induce a physiological state that renders bacilli less susceptible to antibiotics. A regimen that includes at least five effective TB medicines is currently recommended by WHO for treatment of MDR-TB, and the treatment requires 9-12 months of clinical monitoring. Thus, there is an urgent need for potent new drugs that are able to shorten treatment duration and to kill intracellular, latent and drug-resistant Mtb.

Prokaryotic DNA gyrase is a type II topoisomerase that can introduce (−) supercoils to DNA substrates with the hydrolysis of ATP. This enzyme is composed of two different subunits, gyrA and gyrB that form an active $A_2B_2$ complex. Because DNA gyrase only exists in bacteria and is an essential enzyme, it is possible to inhibit DNA gyrase without affecting host human enzymes. Additionally, DNA gyrase can form covalent enzyme-DNA complex intermediates. This property makes gyrase an excellent bactericidal target for developing antibiotics.

Indeed, DNA gyrase is an essential enzyme in Mtb, and represents a validated and highly vulnerable target for new antibiotics to treat MDR-TB. Fluoroquinolones (FQ) are among the most successful antibiotics targeting DNA gyrase. The mechanism of antibacterial activities of fluoroquinolones is to stabilize the enzyme-DNA cleavage-complex, which is ultimately responsible for cell death. This gyrase poisoning mechanism makes fluoroquinolones one of the most effective antibiotics. Moxifloxacin and levofloxacin are on the WHO List of Essential Medicines for the treatment of MDR-TB.

Unfortunately, fluoroquinolones may cause serious adverse effects for certain patients. The adverse effects include tendonitis and tendon rupture, peripheral neuropathy, hyperglycemia, and aortic dissections and aortic aneurysm. As a result, the FDA issued several warnings for the use of fluoroquinolones and added black box warnings on all fluoroquinolones.

In addition, the use of fluoroquinolones as effective anti-TB drugs is compromised by the emerging resistance to fluoroquinolones in Mtb. The fluoroquinolone resistance is mainly due to mutations of Mtb gyrase within the small quinolone-resistance-determining region (QRDR). Most fluoroquinolone mutations occur in the QRDR of GyrA. Certain mutations, although rare, also appear in the QRDR of GyrB. Because fluoroquinolones have been explored extensively in terms of improving spectrum and potency, and overcoming resistance, the limits of what these compounds can provide likely have been reached.

Bacterial resistance to fluoroquinolones makes the development of new, more effective antibiotics an urgent issue especially for Gram-negative bacterial infections. Therefore, it is a need to develop and identify new types of compounds targeting bacterial topoisomerases including DNA gyrases, for example, targeting a different region of Mtb gyrase, to overcome fluoroquinolone-resistance and offer a promising strategy for treating bacterial infections, e.g., fluoroquinolone-resistant MDR-TB.

BRIEF SUMMARY OF THE INVENTION

The subject invention provides fluorophore-quencher nucleic acid molecules comprising relaxed or supercoiled DNA molecules, and their use in rapid and efficient high-throughput screening (HTS) assays, e.g., an supercoiling dependent fluorescence quenching (SDFQ)-based HTS assay, to identify inhibitors of DNA gyrases from the millions of compounds found in small molecule libraries, e.g., the National Institutes of Health's Molecular Libraries Small Molecule Repository library (MLSMR), that potentially target DNA gyrases.

The subject invention also provides compounds, compositions and methods for inhibiting DNA gyrases. The subject invention also provides compounds, compositions and methods for treating and/or preventing infections caused by pathogens such as bacteria, preferably, via the inhibition of DNA gyrases of the pathogens. Advantageously, because DNA gyrase only exists in bacterial cells and is an essential enzyme, the compounds and compositions of the subject invention can target bacterial DNA gyrase without affecting host human enzymes.

In one embodiment, the compounds have activity against bacterial pathogens, including both gram-positive and -negative bacteria. In a further embodiment, the compounds have activity against mycobacteria. In specific embodiments, the compounds have activity against *E. coli, Staphylococcus aureus, Streptococcus pneumoniae, Helicobacter pylori, Enterococcus faecalis, Mycobacterium avium* or *Mycobacterium tuberculosis*. In a preferred embodiment, the compounds have activity against *M. tuberculosis* and pulmonary non-tuberculosis mycobacteria (NTM), such as *Mycobacterium abscessus*.

In one embodiment, the compounds and compositions of the subject invention can be used to inhibit the growth of pathogens by inhibiting DNA gyrases.

In one embodiment, the compounds are used as antibacterial drugs in antibacterial therapy. In a specific embodiment, the compounds are used in treatment of infectious diseases, preferably, tuberculosis. In another embodiment, the compounds are bactericidal against drug resistant bacterial pathogens, preferably, *M. tuberculosis* and *Staphylococcus aureus*.

In one embodiment, the current invention also provides a method for treating a bacterial infection in a subject, comprising administering an effective amount of the pharmaceutical composition comprising one or more compounds according to the subject invention, to a subject in need of such treatment. In a preferred embodiment, the subject is a human.

Further provided herein are kits for screening for inhibitors targeting DNA gyrases using the circular plasmid DNA molecules. The methods, molecules and kits herein described can be used in connection with pharmaceutical, medical, and veterinary applications, as well as fundamental scientific research and methodologies, as would be identifiable by a skilled person upon reading of the present disclosure.

BRIEF DESCRIPTION OF THE DRAWINGS

FIG. 1 shows the supercoiling dependent fluorescence quenching (SDFQ) assay by *E. coli* DNA gyrase in 1×gyrase buffer using plasmid pAB1_FL905. Fluorescence intensity is dependent on the supercoiling status of the plasmid.

FIGS. 2A-2E show SDFQ assays by *E. coli* DNA gyrase in 1×gyrase buffer using different concentrations of pAB1_FL905: 9.63 (A), 6.42, (B), 4.81 (C), and 3.212 (D) ng/μL of pAB1_FL905. (E) Two different concentrations 6.45 and 4.81 ng/μL of pAB1_FL905 were used in the SDFQ assays. Fluorescence was measured using λex=484 nm and λe=520 nm.

FIGS. 5A-5E show SDFQ assays by *E. coli* DNA gyrase in 1×gyrase buffer using pAB1_FL924 to determine the optimal conditions for the HTS assays. (A) different concentrations of pAB1_FL924 were used. (B) Different concentrations of *E. coli* DNA gyrase were used. (C) and (D) DMSO's effects. (e) Novobiocin potently inhibited *E. coli* DNA gyrase activities. Fluorescence was measured using λex=531 nm and λem=595 nm.

FIGS. 8A-8C show the inhibition of *E. coli* DNA gyrase activities by metergoline and chloro-IB-MECA. (A) The SDFQ assays. (B) and (C) The agarose gel-based DNA gyrase assays. The $IC_{50}$ of chloro-IB-MECA is less than 5 μM.

FIG. 9 shows the chemical structures of chloro-IB-MECA, IB-MECA, AB-MECA, adenosine, and metergoline.

FIG. 11 shows the inhibition of the ATPase activities of *E. coli* DNA gyrase by chloro-IB-MECA and IB-MECA. In contrast, 100 μM of AB-MECA did not inhibit the ATPase activities of *E. coli* DNA gyrase.

FIGS. 12A-12D show effects of chloro-IB-MECA (CIM), IB-MECA (IM), and ABMECA (AM) on Mtb DNA gyrase (A). Chloro-IB-MECA did not inhibit *E. coli* DNA topoisomerase I (B), *E. coli* DNA topoisomerase IV (C, lanes 1-5), and human DNA topoisomerase Iialpha (c, lanes 6-7). (D) Chloro-IB-MECA did not DNA double stranded DNA breaks. All experiments were described in Method.

FIGS. 26A-26B show SDFQ-based gyrase inhibition assays to determine the inhibition $IC_{50}$ of MolPort compounds against *E. coli* DNA gyrase. SDFQ-based gyrase inhibition assays were described in Methods. (A) The SDFQ titration assays. (B) The inhibition $IC_{50}$ values against *E. coli* DNA gyrase.

FIGS. 27A-27F show agarose gel-based gyrase inhibition assays to determine the inhibition $IC_{50}$ of psoralen derivatives against *E. coli* DNA gyrase. Agarose gel-based gyrase inhibition assays were described in Methods. Compound # are placed above the gels. (A) to (D). Lanes 1-4 or 5-8 correspond, respectively, to 50, 25, 12.5, and 6.25 μM of the compounds used in the assays. Lanes 9 and 10 are sc and rx pAB1, respectively. (E) Lanes 1-4 correspond, respectively, to 50, 25, 12.5, and 6.25 μM of the compounds used in the assays. Lanes 5 and 6 are se and rx pAB1, respectively. (F) Lanes 1-4 or 5-8 correspond, respectively, to 12.5, 6.25, 3.13, and 1.56 μM of the compounds used in the assays. Lanes 9 and 10 are se and rx pAB1, respectively.

FIGS. 28A-28B show SDFQ-based gyrase inhibition assays to determine the inhibition $IC_{50}$ of all psoralen derivatives against *E. coli* DNA gyrase. SDFQ-based gyrase inhibition assays were described in Methods. (A) The SDFQ titration assays. (B) The inhibition $IC_{50}$ values against *E. coli* DNA gyrase and MIC of the psoralen derivatives against *S. aureus* and MRSA.

FIG. 29 shows structure-activity relationships. A $CH_3$ group in R9 improves the in vitro inhibitory activities against *E. coli* DNA gyrase.

FIG. 33 shows the chemical structures of compound 9 and derivatives.

FIGS. 34A-34D show agarose gel-based gyrase inhibition assays to determine the inhibition $IC_{50}$ of compound 9 derivatives against *E. coli* DNA gyrase. Agarose gel-based gyrase inhibition assays were described in Methods. Compound # are placed above the gels. (A), (C), and (D). Lanes 1-4 or 5-8 correspond, respectively, to 50, 25, 12.5, and 6.25 μM of the compounds used in the assays. Lanes 9 and 10 are sc and rx pAB1, respectively. (B) Lanes 1-4 correspond, respectively, to 50, 25, 12.5, and 6.25 μM of the compounds used in the assays. Lanes 5 and 6 are se and rx pAB1, respectively.

FIGS. 35A-35B show SDFQ-based gyrase inhibition assays to determine the inhibition $IC_{50}$ of compound 9 and derivatives against *E. coli* DNA gyrase. SDFQ-based gyrase inhibition assays were described in Methods. (A) The SDFQ titration assays. (B) The inhibition $IC_{50}$ values against *E. coli* DNA gyrase and MIC of compound 9 and derivatives against *S. aureus* and MRSA.

FIGS. 39A-39H show compound 154 as a bacterial DNA gyrase poison. (A) SDFQ-based gyrase assays in the presence of compound 154 (open squares) and novobiocin (solid circles). The $IC_{50}$ values against *E. coli* DNA gyrase are 3.1±0.7 μM. The standard deviations are calculated according to three independent experiments. (B) Agarose gel-based gyrase inhibition assays for compound 154. Lanes 3-8 correspond to 1.56, 3.12, 6.25, 12.5, 25, and 50 μM of the compound, respectively. Lanes 1 and 2 are relaxed and supercoiled plasmid pAB1, respectively. (C) Gyrase-mediated DNA cleavage assays were performed as described in Methods using plasmid pBR322. Lanes 1 do not contain a gyrase inhibitor. Lanes 2-5 contain 10, 50, 100, 150, and 200 μM of compound 154, respectively. Lane 7 contain 50 μM of ciprofloxacin (CFX). (D) Agarose gel-based inhibition assays against human DNA topoisomerase 2α for compound 154. Lanes 3-6 correspond to 0, 25, 50, and 100 μM of the compound, respectively. Lanes 1 and 2 are relaxed and supercoiled plasmid pAB1, respectively. (E) Human DNA topoisomerase 2α-mediated DNA cleavage assays were performed as described in Materials and Methods using plasmid pBR322. Lanes 1 do not contain any inhibitors. Lanes 1-3 contain 50, 100, and 200 μM of compound 154, respectively. Lane 4 contain 100 μM of etoposide (ETP). Lanes 5 and 6 contain DNA samples from the assay mixtures in the absence of etoposide and human DNA topoisomerase 2a, respectively. Symbols Rx, Sc, Nk, and Ln represent relaxed, supercoiled, nicked, and linear DNA, respectively. (F) Compound 154 is a gyrase poison that inhibits *E. coli* DNA gyrase and Topoisomerase IV. (G) and (H) show molecular models of compound 154 binding to gyrase-DNA complexes. (G) Compound 154 is shown in space fill model. (H) Compound 154 (stick model) intercalates between DNA base pairs (space fill models).

FIGS. 40A-40G show compound 40 as a bacterial DNA gyrase poison. (A) SDFQ-based gyrase assays in the presence of compound 40 (open squares) and novobiocin (solid circles). The $IC_{50}$ values against *E. coli* DNA gyrase are 47.6±3.7 μM. The standard deviations are calculated according to three independent experiments. (B) Agarose gel-based gyrase inhibition assays for compound 40. Lanes 3-9 correspond to 6.25, 12.5, 25, 50, 100, 150, and 200 μM of compound 40, respectively. Lanes 1 and 2 are relaxed and supercoiled plasmid pAB1, respectively. (C) Gyrase-mediated DNA cleavage assays were performed as described in Materials and Methods using plasmid pBR322. Lanes 6 and 1 to 4 contain 0, 50, 100, 150, and 200 μM of compound 40, respectively. Lane 5 contain 50 μM of ciprofloxacin (CFX). (D) Agarose gel-based inhibition assays against human DNA topoisomerase 2a for compound 40. Lanes 3-6 correspond to 12.5, 25, 50, and 100 μM of compound 40, respectively. Lanes 1 and 2 are relaxed and supercoiled plasmid pAB1, respectively. (E) Human DNA topoisomerase 2α-mediated DNA cleavage assays were performed as described in Materials and Methods using plasmid pBR322. Lanes and 2 contain 100 and 200 μM of compound 40, respectively. Lane 3 contains 100 μM of etoposide (ETP). Lanes 4 and 5 contain DNA samples from the assay mixtures in the absence of etoposide and human DNA topoisomerase 2a, respectively. Symbols Rx, Sc, Nk, and Ln represent relaxed, supercoiled. (F) and (G) show molecular models of compound 40 binding to gyrase-DNA complexes. (F) Compound 40 is shown in space fill model. (G) Compound 40 (stick model) intercalates between DNA base pairs.

FIGS. 42A-42H show inhibition of *E. coli* DNA gyrase activity by gallic acid derivatives. (A-D) Chemical structure of (A) tannic acid, (B) digallic acid, (C) gallic acid and (D) egallic acid. (E-H) Inhibition of *E. coli* DNA gyrase supercoiling activities by tannic acid, digallic acid, gallic acid, and ellagic acid. Novobiocin was used as a positive control. Symbols: Rx, relaxed plasmid pAB1; Sc, supercoiled pAB1.

FIGS. 43A-43B show the inhibition of *E. coli* DNA gyrase by gallate derivatives. Symbols: Rx, relaxed plasmid pAB1; Sc, supercoiled pAB1. (A) Lanes 1-6 contain 0, 5, 10, 20, 50 and 100 μM of butyl gallate, respectively. Lanes 7-11 indicate 5, 10, 20, 50 and 100 μM of octyl gallate, respectively. Lanes 12-16 indicate 5, 10, 20, 50 and 100 μM of dodecyl gallate, respectively. (B) Lanes 1-6 contain 0, 5, 10, 20, 50 and 100 μM of phenyl gallate, respectively. Lanes 7-11 indicate 5, 10, 20, 50 and 100 μM of biphenyl gallate, respectively. Lanes 12 and 13 represent supercoiled and relaxed plasmid pAB1, respectively. BG: butyl gallate, OG: octyl gallate, DG: dodecyl gallate, PG: phenyl gallate, and BPG: biphenyl gallate.

FIGS. 44A-44D show the inhibition of the ATPase activities of *E. coli* DNA gyrase by Digallic acid and other gallate derivatives. (A and B) SDFQ-based DNA gyrase supercoiling assays. (A) An experimental strategy to study DNA gyrase inhibitors. The IC50 values can be determined by a titration experiment. (B) Titration experiments to determine the IC50 of digallic acid (red up triangles), octyl gallate (green down triangles), dodecyl gallate (blue squares), biphenyl gallate (black circles), and novobiocin (stars). (C and D) Digallic acid and other gallate derivatives are competitive inhibitors of the ATPase activities of *E. coli* DNA gyrase. (D) Lineweaver-Burk plot or double-reciprocal plot of *E. coli* DNA gyrase in the absence (open triangles) or presence (closed squares) of 500 nM digallic acid. (D) ATP hydrolysis activities of *E. coli* DNA gyrase in presence of different gallate derivatives (100 μM). Symbol: DNA gyrase only, open down triangles; digallic acid, red up triangles; octyl gallate, green down triangles; dodecyl gallate, blue squares; biphenyl gallate, black circles; and novobiocin (open circles).

FIGS. 45A-45E show the inhibition of *E. coli* DNA topoisomerase IV by digallic acid and other gallate derivatives. Relaxation assays by *E. coli* DNA topoisomerase IV and the ATPase assays were performed. (A) Digallic acid potently inhibits *E. coli* DNA topoisomerase IV. Lanes 2-8 contain 0, 6.25, 8, 10, 12.5, 25, and 50 μM of digallic acid, respectively. Lane 1 is supercoiled plasmid pAB1. IC50 of digallic acid against *E. coli* DNA topoisomerase IV was estimated to be ~8 μM. (B) Inhibition of gallate derivatives against *E. coli* DNA topoisomerase IV at 100 μM. (C) Titration experiments to determine IC50 of dodecyl gallate, octyl gallate, and biphenyl gallate against *E. coli* DNA topoisomerase IV. Symbols: Digallic acid, DA; butyl gallate, BG; octyl gallate, OG; dodecyl gallate, DG; phenyl gallate, PG; and biphenyl gallate, BPG; Ln, linear DNA, Nk, nicked DNA, Rx, relaxed DNA, Sc, supercoiled DNA. (D) SDFQ-based DNA relaxation assays to determined IC50 of digallic acid (red up triangles), octyl gallate (green down triangles), dodecyl gallate (blue squares), biphenyl gallate (black circles), and novobiocin (stars). The supercoiled, fluorescently-labeled plasmid pAB1_FL905 was used. Fluorescence measurements were performed in a Biotek Synergy H1 Hybrid Plate Reader using a wavelength of 494 nm and 521 nm for excitation and emission, respectively. (E) ATP hydrolysis activities of *E. coli* DNA topoisomerase IV in presence of different gallate derivatives (100 μM). Symbol: DNA gyrase only, open down triangles; digallic acid, red up triangles; octyl gallate, green down triangles; dodecyl gallate, blue squares; biphenyl gallate, black circles; and novobiocin (open circles).

FIGS. 46A-46D show that digallic acid and gallate derivatives did not strongly inhibit *E. coli* DNA topoisomerase I (A), human DNA topoisomerase I (B), and human DNA topoisomerase IIα (C). 100 μM of compounds were used. (D) DNA gyrasemediated DNA cleavage assays were performed. Lanes 2-6 contain 0, 6.25, 12.5, 50, 100, 150, and 200 μM of digallic acid, respectively. Lane 1 contains 10 μM of ciprofloxacin. Symbols: Digallic acid, DA; butyl gallate, BG; octyl gallate, OG; dodecyl gallate, DG; phenyl gallate, PG; and biphenyl gallate, BPG; Ln, linear DNA, Nk, nicked DNA, Rx, relaxed DNA, Sc, supercoiled DNA.

FIGS. 47A-47I show molecular models of digallic acid (A-C), dodecyl gallate (D-F), and biphenyl gallate (G-1) binding to the ATP binding pocket of *E. coli* DNA Gyrase B. A hydrogen bond is formed between all gallate derivatives (digallic acid, dodecyl gallate, and biphenyl gallate) and residue Asp73. C, F, and I show schematic 2-D representations of *E. coli* DNA gyrase-ligand complexes. Hydrogen bonds are highlighted as green dashed lines. Hydrophobic contacts are shown as an arc with spokes radiating towards the ligand atoms.

FIGS. 48A-48D show CPD 229 and analogs as bacterial DNA gyrase poisons. The $IC_{50}$ against *E. coli* (A) and Mtb (C) gyrase were determined using the gel-based gyrase inhibition assays. The gyrase mediated DNA cleavage assays (B and D) were performed using pBR322. (A) 229 inhibits *E. coli* gyrase. Lane 1, rx pAB1. Lanes 2-9 contain 0, 3.1, 6.3, 12.5, 25, 50, 100, and 200 μM of 229. (B) 229 induces DNA nicking by *E. coli* gyrase. Lane 1, no inhibitor; lane 2, 50 μM of ciprofloxacin; and lanes 3 and 4 contain 50 and 100 μM of 229, respectively. (C) 229 potently inhibits Mtb gyrase. Lane 1, rx pAB1. Lanes 2-9 contain 0, 3.1, 6.3, 12.5, 25, 50, 100, and 200 μM of 229. (D) Mtb gyrase mediated DNA cleavage assays for 229 (lanes 1 (100 μM) and 2 (50 μM)), 259 (lane 3), 260 (lane 4), 261 (lane 5), 262 (lane 6), 263 (lane 7), 264 (lane 8), and ciprofloxacin (lane 9, 50 μM). 100 μM of CPDs were used. Symbols rx, nk, ln, and sc represent relaxed, nicked, linear, and supercoiled DNA, respectively.

DETAILED DESCRIPTION OF THE INVENTION

Figure 3A:
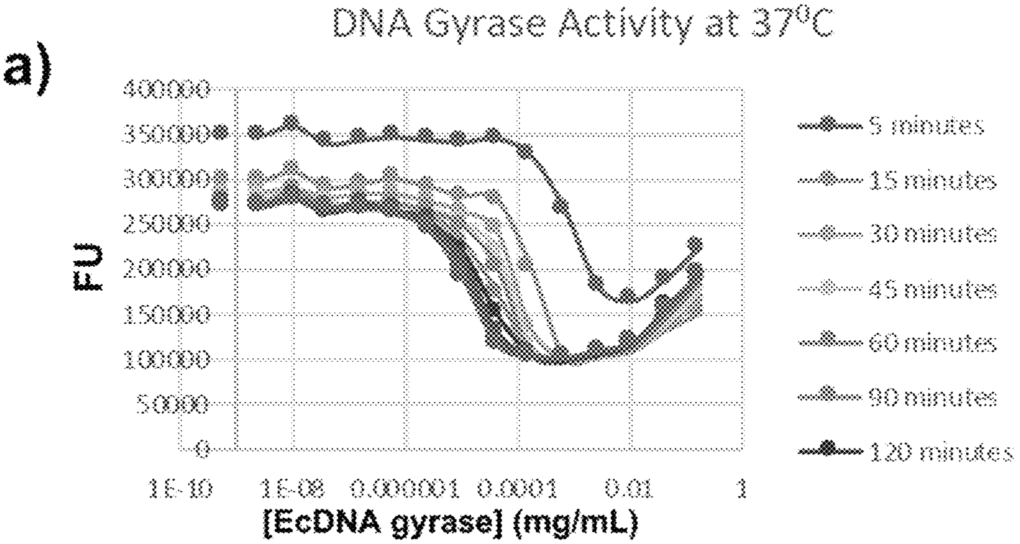
FIGS. 3A-3C show SDFQ assays by *E. coli* DNA gyrase in 1×gyrase buffer using pAB1_FL905. (A) Different concentrations of *E. coli* DNA gyrase were used. (B) Time courses in the presence or absence of *E. coli* DNA gyrase. 3.21 ng/μL of pAB1_FL905 was used. (C) DMSO's effects on SDFQ assays. Fluorescence was measured using λex=484 nm and λe=520 nm.

The subject invention provides fluorophore-quencher nucleic acid molecules comprising relaxed or supercoiled DNA molecules, and their use to study DNA topology, and DNA gyrases.

The subject invention provides rapid and efficient high-throughput screening (HTS) assays, e.g., in 384-well or 1536-well plates, using these nucleic acid molecules to identify inhibitors of DNA gyrases from millions of compounds in small molecule libraries that potentially target DNA gyrases. Also provided are synthetic entities yielded by screening chemical compound libraries for further development of inhibitors of DNA gyrases.

The subject invention also provides compounds, compositions and methods for inhibiting DNA gyrases. The subject invention also provides compounds, compositions and methods for treating and/preventing infections caused by pathogens such as bacteria, preferably, via the inhibition of DNA gyrases of the pathogens. Advantageously, because DNA gyrase only exists in bacterial cells and is an essential enzyme, the compounds and compositions of the subject invention can target bacterial DNA gyrase without affecting host human or other animal enzymes.

In one embodiment, the subject invention provides a method to produce fluorescently labeled, relaxed (rx) or supercoiled (sc) DNA molecules to study DNA topoisomerases by supercoiling dependent fluorescence quenching (SDFQ) (FIG. 1). This assay stems from a property of alternating $(AT)_n$ sequences in the closed circular plasmids that undergo rapid cruciform formation-deformation depending on the supercoiling status of the plasmids. The distance between a pair of fluorophore-quencher inserted in the $(AT)_n$ sequence is dramatically changed when the plasmids adopt an sc or rx form, as does the fluorescence intensity of the plasmid. These DNA molecules are excellent tools to examine relaxation/supercoiling kinetics of various DNA topoisomerases and can be configured into HTS assays to identify gyrase inhibitors.

In accordance with the subject invention, nucleic acids comprising an adenosine-thymidine repeat $(AT)_n$ sequence comprise at least one fluorophore and at least one quencher conjugated to the same strand when present in a circular double-stranded DNA molecule, which can be used for fast detection of changes in DNA topology. The fluorophore and quencher conjugated to the same DNA strand of a double-stranded $(AT)_n$ sequence quickly interconvert between an extruded and an unextruded conformation upon supercoiling of the circular DNA. In the supercoiled state, the $(AT)_n$ sequence adopts, for example, a hairpin structure that brings the fluorophore and the quencher into close proximity and leads to the quenching of fluorophore fluorescence. In the relaxed circular DNA molecule, where the $(AT)_n$ is in a double-stranded conformation, the fluorophore and quencher are located at a sufficient distance such that no quenching occurs and the fluorophore fluoresces.

The instant fluorophore-quencher comprising (AT), nucleic acid sequences have advantageous properties. For example, interconversion between the extruded and unextruded conformation of the fluorophore-quencher nucleic acid sequences occurs with fast kinetics allowing rapid detection of changes in fluorescence as the circular DNA undergoes structural changes upon supercoiling and relaxation. The instant fluorophore-quencher (AT), nucleic acids can be used to gauge superhelicity of DNA molecules and detect the presence of DNA topology-affecting enzymes. The instant fluorophore-quencher nucleic acids are well-suited for high-throughput analyses of topology changes of DNA because of the speed of change in DNA conformation and the fast kinetics of changes in fluorescence.

In specific embodiments, the nucleic acids comprising the repeat $(AT)_n$ sequence are circular double-stranded (ds) DNA molecules, e.g., plasmids, which have the ability to interconvert between a relaxed (rx) configuration and a supercoiled (sc) configuration.

In certain embodiments, the circular double-stranded plasmid may comprise, for example, about 1000 base pairs to 100,000 base pairs, about 1000 base pairs to 50,000 base pairs, about 1000 base pairs to 20,000 base pairs, about 1000 base pairs to 10,000 base pairs, about 1000 base pairs to 5000 base pairs, about 1000 base pairs to 4000 base pairs, about 1000 base pairs to 3000 base pairs, about 1500 base pairs to 3000 base pairs, or about 2000 base pairs to 3000 base pairs.

In one embodiment, the circular double-stranded plasmid comprises a sequence comprising adenosine-thymidine repeats $(AT)_n$ ($n \geq 2$) in each strand. In some embodiments, $n \geq 2$, 3, 4, 5, 6, 7, 8, 9, 10, 11, 12, 13, 14, 15, 16, 17, 18, 19, 20, 21, 22, 23, 24, 25, 26, 27, 28, 29, 30, 34, 32, 33, 34, 35, 36, 37, 38, 39, 40, 41, 42, 43, 44, 45, 46, 47, 48, 49, or 50. In a specific embodiment, in the se state, the sequence comprising (AT)n adopts, for example, the hairpin/cruciform structures in each strands of the circular double-stranded plasmid, while in the rx circular dsDNA molecule, the sequences comprising (AT)n are in a double-stranded conformation.

In specific embodiments, the $(AT)_n$ sequence of the instant fluorophore-quencher nucleic acid can comprise a low of about 12 AT dinucleotides to a high of about 50 AT dinucleotides. For example, the instant fluorophore-quencher nucleic acid can comprise AT dinucleotide sequences from about 12 ATs to about 17 ATs; about 18 ATs to about 25 ATs; about 26 ATs to about 33 ATs; about 34 to about 41 ATs; or about 42 to about 50 ATs.

The (AT), sequence of the instant nucleic acid can comprise the at least one fluorophore and the at least one quencher conjugated to a deoxythymidine (dT) at a predetermined distance from the 5' end of the $(AT)_n$ sequence. For example, the quencher can be located at, for example, the $4^{th}$, $5^{th}$, $6^{th}$, $7^{th}$, $8^{th}$, $9^{th}$, $10^{th}$, $11^{th}$, $12^{th}$, $13^{th}$, or $14^{th}$ position from the 5' start of the $(AT)_n$ sequence. The fluorophore may be located at, for example, the $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, or $40^{th}$ position from the 5' start of the $(AT)_n$ sequence.

Many fluorophores can be used to make the instant fluorophore-quencher nucleic acids. For example, the fluorophore can be 6-FAM (fluoroscein), Cy3™, TAMRA™, JOE, Cy5™, Cy5.5™, MAX, TET™, Carboxy-X-Rhodamine, TYE™ 563, TYE™ 665, TYE 705, Yakima Yellow®, Hexachlorofluorescein, TEX 615, Alexa Fluor® 488, Alexa Fluor® 532, Alexa Fluor® 546, Alexa Fluor® 594, Alexa Fluor® 647, Alexa Fluor® 660, Alexa Fluor® 750m 5' IRDye® 700, 5'IRDye® 800, 5' IRDye®800CW, ATTO™ 488, ATTO™ 532, ATTO™ 550, ATTO™ 565, ATTO™ Rho101, ATTO™ 590, ATTO™ 633, ATTO™ 647, Rhodamine Green™-X, Rhodamine Red™-X, 5-TAMRA™, WEllRED D2, WellRED D3, WellRED D4, Texas Red®-X, Lightcycler® 640, DY 750, BODIPY FL, EDANS, or IAEDANS.

The quenchers used to make the instant fluorophore-quencher nucleic acids can be, for example, Dabcyl, DDQ-I, Eclipse, Iowa Black FQ, BHQ-1, QSY-7, BHQ-2, DDQ-II, Iowa Black RQ, QSY-21, or BHQ-3.

In a specific embodiment, the circular double-stranded DNA comprising at least one fluorophore and at least one quencher on the same strand undergoes supercoiling in the presence of a DNA gyrase, wherein the fluorophore-quencher comprising nucleic acid sequence undergoes rapid localized DNA conformation transition, i.e. interconversion from the unextruded conformation in the double-stranded DNA to an extruded conformation in the supercoiled state and quenching of fluorophore fluorescence occurs based on the close proximity of the fluorophore and quencher in the extruded conformation. Thus, the instant circular DNA plasmids comprising fluorophore-quencher containing nucleic acid sequences can be used to detect the presence of, and study the properties of, DNA gyrases, and to screen or identify inhibitors of DNA gyrases. In a specific embodiment, the DNA gyrase is *E. coli* DNA gyrase or Mtb DNA gyrase.

In one embodiment, the subject invention provides an SDFQ-based HTS assay to identify inhibitors targeting bacterial DNA gyrase. After screening the NCATS compound library containing 370,620 compounds, 102 new bacterial DNA gyrase inhibitors were identified/discovered. Several new gyrase inhibitors cause the gyrase-mediated double-stranded DNA breaks and DNA nicks, and most likely are new DNA gyrase poisons.

Advantageously, because the new DNA gyrase inhibitors are structurally different from fluoroquinolones (FQs), the clinically important antibiotics targeting DNA gyrase, these new gyrase inhibitors use a mechanism of action (MoA) different from FQs and have potential to overcome multidrug resistance and be used as new antibiotics to treat multidrug resistant bacterial infections. These newly discovered DNA gyrase inhibitors provide novel scaffolds for the design and synthesis of bacterial DNA gyrase inhibitors to combat antibacterial resistance.

In one embodiment, the subject invention provides methods for HTS to identify inhibitors of DNA gyrase, the method comprising providing a sample carrier, e.g., HTS plates such as a microplate, comprising arrays of individual reservoirs, each reservoir containing a compound of a screening library or a control, adding a circular dsDNA molecule of the subject invention and an DNA gyrase in each reservoir; and determining the inhibitors based on the fluorescence in each reservoir.

In one embodiment, the DNA gyrase inhibitor of the subject invention has a general structure of formula (I):

(I)

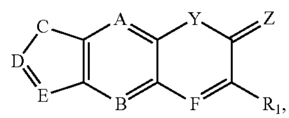

wherein Y is $CR_2R_3$, O, S, or $NR_4$; A and B are each independently $CR_5$ or N; C is $CR_6R_7$, O, S or $NR_8$; D and E are each independently $CR_9$ or N; F is $CR_9$ or N; and Z is O or S, wherein $R_1$, $R_2$, $R_3$, $R_5$, $R_6$, $R_7$, and $R_9$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxy, hydroxy, carboxy, carbonyl, amine, amide, ester, haloalkyl, haloaryl, thio, thioamide, urea, and thiourea; and $R_4$ and R8 are each independently selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxy, hydroxy, carboxy, carbonyl, amine, amide, ester, haloalkyl, haloaryl, thio, thioamide, urea, and thiourea.

In one embodiment, the DNA gyrase inhibitors are psoralen and derivatives having a structure of formula (II):

(II)

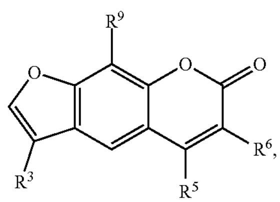

wherein $R^3$, $R^5$, $R^6$, and $R^9$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxy, hydroxy, carboxy, carbonyl, amine, amide, ester, haloalkyl, haloaryl, thiol, thioamide, urea, and thiourea.

In a specific embodiment, $R^9$ is H or alkyl, preferably, C1-C3 alkyl, more preferably, methyl.

In a specific embodiment, $R^5$ is alkyl, preferably, C1-C3 alkyl, more preferably, methyl.

In a specific embodiment, $R^6$ is carboxyl, preferably, $(CH_2)_2COOH$.

In specific embodiments, $R^3$ is alkyl, aryl or substituted aryl. In a preferred embodiment, $R^3$ is methyl, or

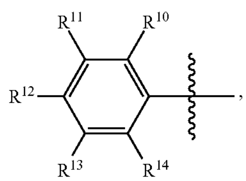

wherein $R^{10}$, $R^{11}$, $R^{12}$, $R^{13}$, and $R^{14}$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, and substituted heterocycloalkyl.

In a preferred embodiment, $R^3$ is

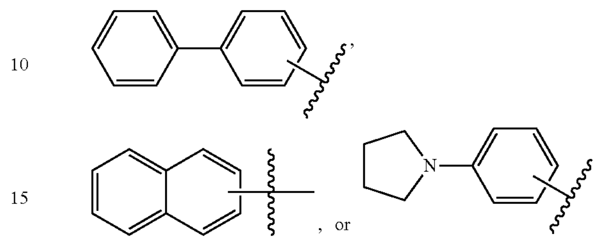

, or

In a specific embodiment, $R^3$ is selected from

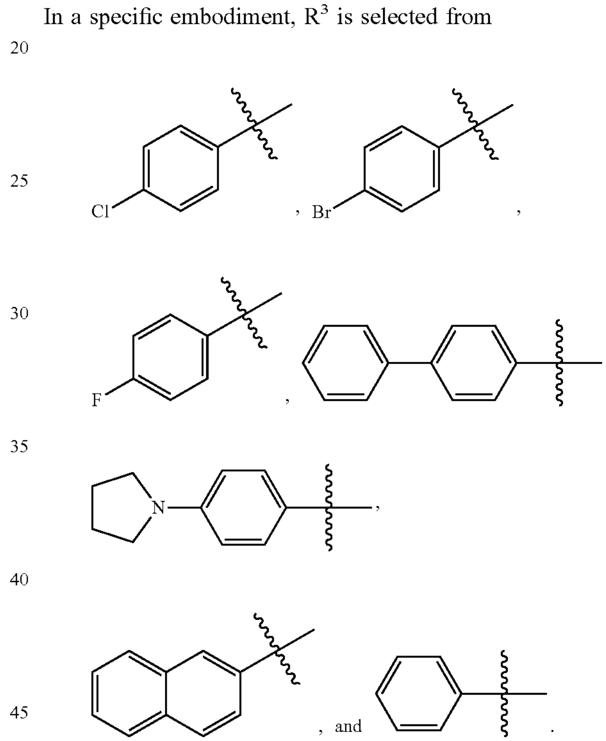

, and

In one embodiment, the DNA gyrase inhibitor of the subject invention has a general structure of formula (III):

(III)

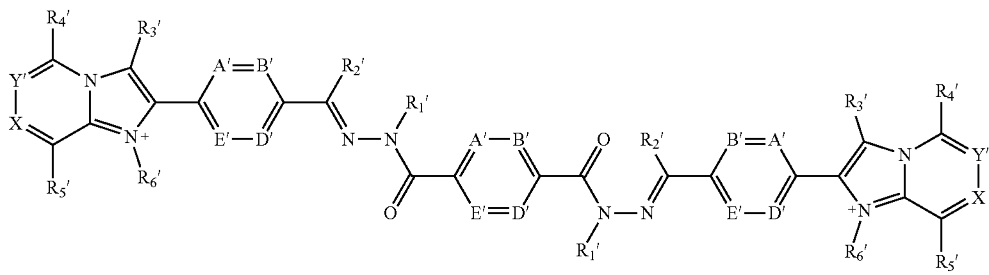

wherein X, Y', A', B', E', and D' are each independently selected from CH, CR and N; R, $R_1'$, $R_2'$, $R_3'$, $R_4'$, and $R_5'$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_6$' is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In one embodiment, the DNA gyrase inhibitor of the subject invention has a general structure of formula (IV):

(IV)

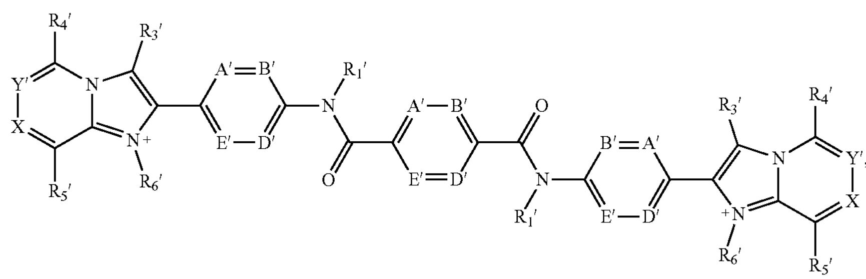

wherein X, Y', A', B', E', and D' are each independently selected from CH, CR and N; R, $R_1$', $R_3$', $R_4$' and $R_5$' are each independently selected from halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_6$' is selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In one embodiment, the DNA gyrase inhibitor of the subject invention is a terephthalamide analog having a general structure of formula (V):

(V)

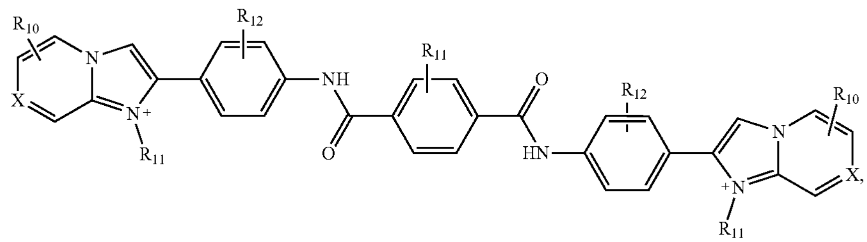

wherein X is selected from CH, CR and N; R, $R_{10}$ and $R_{12}$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_{11}$ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In one embodiment, the DNA gyrase inhibitor of the subject invention has a general structure of formula (VI):

(VI)

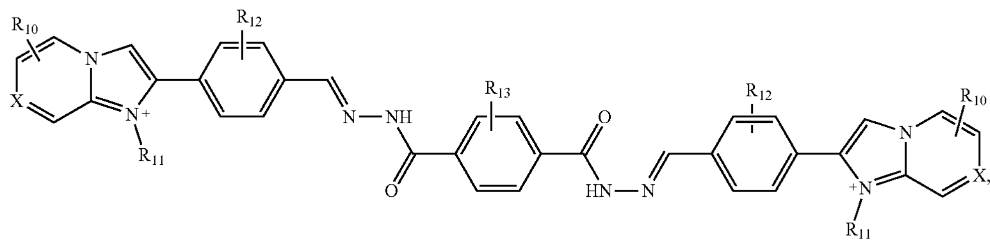

wherein X is selected from CH, CR and N; R, $R_{10}$ and $R_{12}$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; $R_{11}$ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_{13}$ is selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In one embodiment, the DNA gyrase inhibitor of the subject invention has a general structure of formula (VII):

(VII)

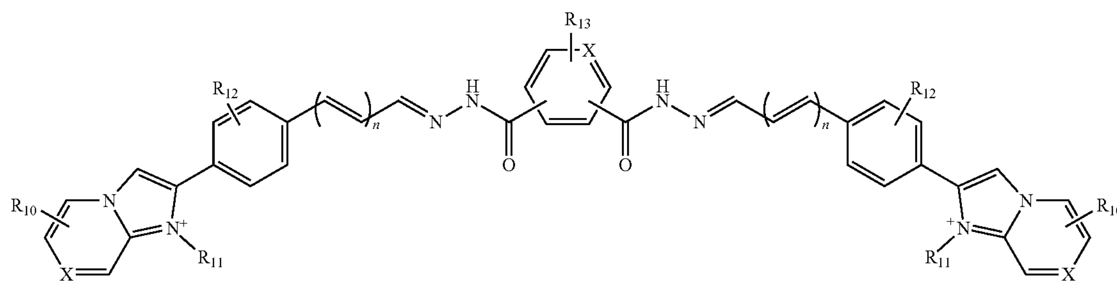

wherein n is 0-5; each X is independently selected from CH, CR and N; R, $R_{10}$ and $R_{12}$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; $R_{11}$ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_{13}$ is selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In one embodiment, the DNA gyrase inhibitor of the subject invention has a general structure of formula (VIII):

(VIII)

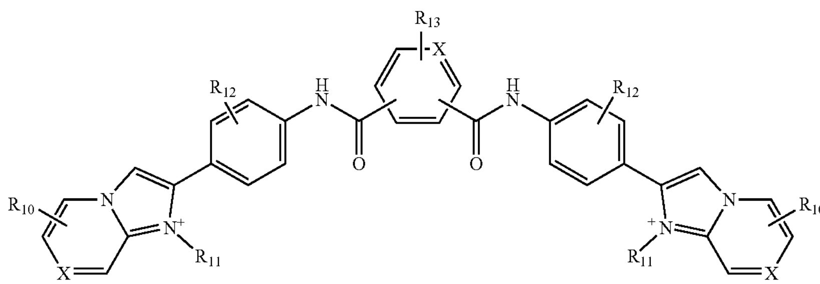

wherein each X is independently selected from CH, CR and N; R, $R_{10}$ and $R_{12}$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; $R_{11}$ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_{13}$ is selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In one embodiment, the DNA gyrase inhibitor of the subject invention has a general structure of formula (IX):

(IX)

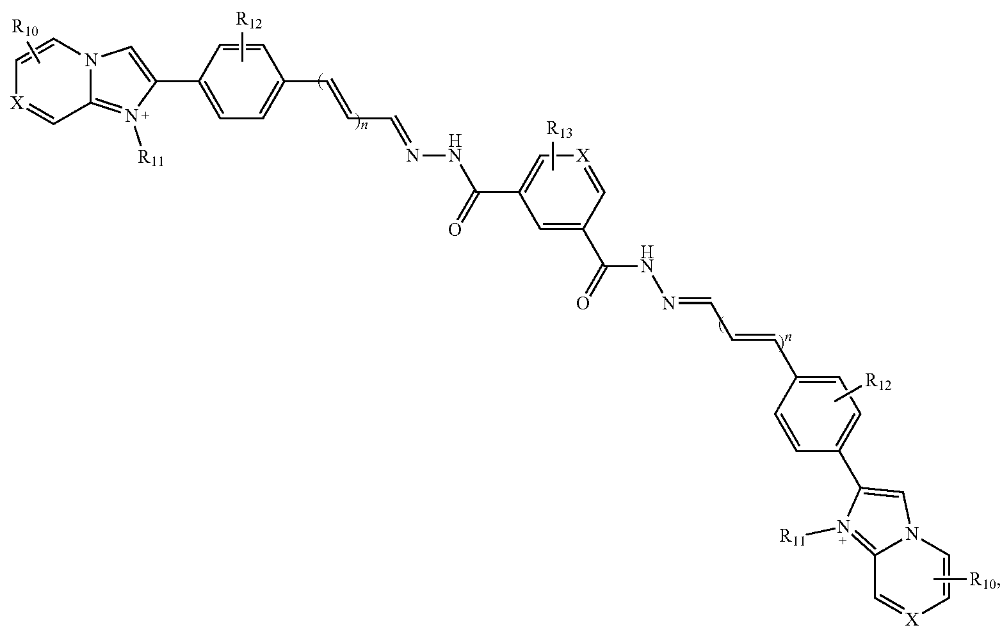

wherein n is 0-5; each X is independently selected from CH, CR and N; R, $R_{10}$ and $R_{12}$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In one embodiment, the DNA gyrase inhibitor of the subject invention has a general structure of formula (X):

(X)

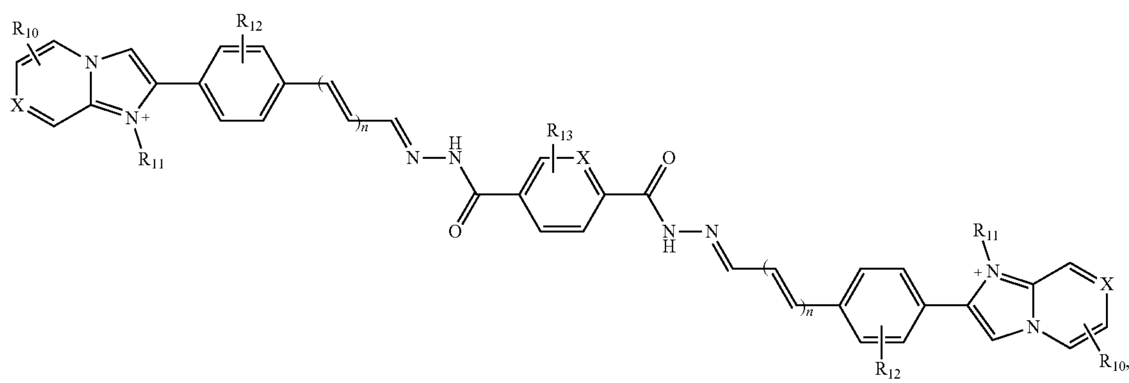

ester, haloalkyl, haloaryl, thiol, thioamide, urea, and thiourea; Rn is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_{13}$ is selected from, for example, halogen, hydrogen, alkyl, substituted alkyl, aryl, substituted aryl, wherein n is 0-5; each X is independently selected from CH, CR and N; R, $R_{10}$ and $R_{12}$ are each independently selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; $R_{11}$ is selected from, for example, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_{13}$ is selected from, for example, halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

In specific embodiments, the DNA gyrase inhibitors are selected from compounds 4, 7, 9, 10, 12, 13, 15, 17, 18, 19, 21, 22, 23, 24, 25, 27, 28, 29, 30, 31, 33, 35, 36, 38, 40, 41, 42, 44, 45, 46, 47, 48, 49, 51, 53, 54, 55, 56, 57, 58, 60, 61, 62, 63, 64, 65, 68, 70, 71, 72, 73, 74, 75, 76, 78, 79, 82, 83, 102, 104, 105, 106, 108, 109, 110, 111, 112, 115, 122, 129, 130, 131, 132, 135, 149, 154, 155, 157, 159, 161, 163, 165, 167, 168, 169, 171, 173, 176, 178, 180, 184, 188, 189, 192, 204, 205, 206, 207, 211, 212, 213, 215, 222, 225, 227, 228, 229, 232, 234, 235, 242, 253, 256, and 259-264.

In specific embodiments, the DNA gyrase inhibitors are selected from compounds 10, 13, 15, 17, 22, 28, 31, 33, 38, 40, 44, 45, 51, 53, 54, 55, 56, 58, 60, 61, 62, 63, 64, 65, 4, 7, 12, 18, 21, 23, 24, 29, 35, 49, 102, 104, 105, 189, 212, 215, 222, 224, 225, 229, 256, 108, 135, 149, 155, 161, 163, 169, 171, 173, 180, 184, 9, 19, 25, 27, 36, 41, 42, 46, 47, 48, 72, 73, 75, 76, 154, 157, 159, 165, 176, 178, 192, 253, and novobiocin.

In specific embodiments, the DNA gyrase inhibitors are selected from compounds chloro-IB-MECA, IB-MECA, AB-MECA, adenosine and metergoline.

In specific embodiments, the DNA gyrase inhibitors are psoralen and derivatives thereof selected from compounds 25, 46, 48, 117, 118, 119, 120, 121, 122, 123, 124, and 125.

In specific embodiments, the DNA gyrase inhibitors are selected from compound 9 and derivatives thereof, for example, compounds 109, 111, 114, 115, 116, 126, 127, 128, and 132.

In specific embodiments, the DNA gyrase inhibitors are selected from dye molecules and natural products, for example, compounds 75, 82, 242, 253, 256, and 225.

In specific embodiments, the DNA gyrase inhibitors are selected from 3a,4,5,9b-Tetrahydro-3H-cyclopenta[c]quinoline-4-carboxylic acid and derivatives, for example, compounds 83, 106, 136, 137, 138, 139, 140, 141, 142, 143, 144, 145, and 146.

In specific embodiments, the DNA gyrase inhibitors are selected from compounds 154, 40, 173, and 232.

In specific embodiments, the DNA gyrase inhibitors are selected from CPD 229 and analogs such as compounds 259-264.

In specific embodiments, the DNA gyrase inhibitors are selected from compounds 67, 69, 81, 101, 103, 107, 113, 114, 116, 117, 119-121, 123-128, 133-134, 141, 147-148, 151-153, 156, 158, 160, 162, 164, 166, 170, 172, 174, 175, 182, 183, 191, 217, 224, 236-241, 243, 245-249, 255, 257, and 258.

In one embodiment, the DNA gyrase inhibitors identified according to the subject invention include, for example, gallic acid and derivatives thereof, such as digallic acid. In specific embodiments, the DNA gyrase inhibitors are selected from digallic acid, butyl gallate, octyl gallate, dodecyl gallate, phenyl gallate and bi-phenyl gallate.

In certain embodiments, the DNA gyrase inhibitors are selected from 1) psoralen derivatives, 2) quinazoline derivatives, 3) dihydroxynaphthalene-2-carboxylate and quinolinedione derivatives, 4) Isatin-phenylhydrazone derivatives, 5) amino-benzothiazole derivatives, 6) thiazolo[3,2-a]benzimidazole derivatives, 7) pyrido-thieno-pyrimidine derivatives, 8) compounds containing a rhodamine moiety, and 9) fluorone derivatives.

In a specific embodiment, the DNA gyrase inhibitor is a quinazoline derivative, such as compound 154, N-(6-chloro-4-phenylquinazolin-2-yl)guanidine.

Advantageously, these bacterial DNA gyrase inhibitors of the subject invention can be used to overcome multidrug resistance and be used as antibiotics to treat bacterial infections, preferably, multidrug resistant bacterial infections.

In one embodiment, the compounds have activity against bacterial pathogens. Bacteria include at least 11 distinct groups as follows: (1) Gram-positive (gram+) bacteria, of which there are two major subdivisions: (i) high G+C group (Actinomycetes, Mycobacteria, *Micrococcus*, others) (ii) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green nonsulfur bacteria (also anaerobic phototrophs); (10) Radioresistant Inicrococci and relatives; and (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium.*

"Gram-positive bacteria" include cocci, nonsporulating rods, and sporulating rods. The genera of Gram-positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces.*

In a further embodiment, the compounds have activity against mycobacteria. In another further embodiment, the compounds have activity against *E. coli, Staphylococcus aureus, Streptococcus pneumoniae, Bacillus subtilis, Bacillus pumilus, Bacillus cereus, Acinetobacter baumanii, Helicobacter pylori, M. smegmatis* and/or *M. tuberculosis*, preferably, *M. tuberculosis.*

In another embodiment, the compounds have activity against drug resistant bacterial pathogens, preferably, *M. tuberculosis* and/or *Staphylococcus aureus*. In another embodiment, the compounds have activity against drug resistant biofilms formed by bacterial pathogens such as NTM.

In one embodiment, the subject invention provides a pharmaceutical composition comprising one or more of the compounds of the subject invention. The composition further comprises a pharmaceutically acceptable carrier, adjuvant, and/or diluent allowing the transport of the compounds to the target within the subject after administration.

The carrier and/or diluent can generally be any suitable medium by which the desired purpose is achieved and that does not affect the conjugates' capability to be directed to the desired target and to transport the active agent to this target for the desired effect. Particularly, the carrier and/or diluent should not deteriorate the pharmacological potency of the active agent and the capability of the complex to be directed to a desired target within, or on, the animal body. Preferably, said carrier and/or diluent is/are selected from water, physiologically acceptable aqueous solutions containing salts and/or buffers and any other solution acceptable for administration to an animal. Such carriers and diluents are well known to a person skilled in this field and can be, for example, distilled water, de-ionized water, pure or ultrapure water, saline, phosphate-buffered saline (PBS), solutions containing usual buffers which are compatible with the other components of the drug targeting system etc.

In one embodiment, the pharmaceutical composition comprising compounds according to the invention, together with a conventional adjuvant, carrier, or diluent, may be placed into the form of solids including tablets, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

In a further embodiment, the composition is in a powder form. The pharmaceutically accepted carrier is a finely divided solid that is in a mixture with the finely divided active compounds. In another embodiment, the composition is in a tablet form. The active component is mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In one embodiment, the subject invention provides a method for treating a subject having a bacterial infection, the method comprising administering the compounds of the subject invention or the composition of the subject invention to the subject in need of such treatment.

In one embodiment, the current invention also provides methods for treating an infection caused by a pathogen in a subject, comprising administering, to a subject in need of such treatment, an effective amount of the pharmaceutical composition comprising a compound according to the subject invention.

In a specific embodiment, the subject invention provides methods for treating a subject with tuberculosis, comprising the administration of the pharmaceutical composition.

In specific embodiments, the compounds may be administered in the range of from 0.01 mg/kg body weight to 1 g/kg body weight, preferably, 1 mg/kg to 500 mg/kg body weight, more preferably, 50 mg/kg to 500 mg/kg body weight.

The effective amount of said pharmaceutical composition can be administered through, for example, oral, rectal, bronchial, nasal, topical, buccal, sub-lingual, transdermal, vaginal, intramuscular, intraperitoneal, intravenous, intraarterial, intracerebral, interocular administration or in a form suitable for administration by inhalation or insufflation, including powders and liquid aerosol administration, or by sustained release systems such as semipermeable matrices of solid hydrophobic polymers containing the compound(s) of the invention. Administration may be also by way of other carriers or vehicles such as patches, micelles, liposomes, vesicles, implants (e.g. microimplants), synthetic polymers, microspheres, nanoparticles, and the like.

In one embodiment, the current invention provides methods for inhibiting a DNA gyrase, in a subject, comprising administering, to a subject in need of such inhibition, an effective amount of the pharmaceutical composition comprising a compound according to the subject invention. In one embodiment, the subject has been diagnosed with an infection caused by a pathogen, e.g., a bacterium, virus, and fungus. In a further embodiment, the DNA gyrase is a bacterial gyrase, such as *M. tuberculosis* DNA gyrase. In another embodiment, the subject is a human. In a preferred embodiment, the compounds of the subject invention do inhibit the DNA gyrase of pathogens without any effect on the subject.

In one embodiment, the composition is formulated for parenteral administration (e.g. by injection, for example bolus injection or continuous infusion). In addition, the composition may be presented in unit dose form in ampoules, pre-filled syringes, and small volume infusion or in multi-dose containers with or without an added preservative. The compositions may be in forms of suspensions, solutions, or emulsions in oily or aqueous vehicles. The composition may further contain formulation agents such as suspending, stabilizing and/or dispersing agents. In a further embodiment, the active ingredient of the composition according to the invention may be in powder form, obtained by aseptic isolation of sterile solid or by lyophilization from solution for constitution with a suitable vehicle, e.g., sterile, pyrogen-free water, before use.

In one embodiment, the composition may be formulated in an aqueous solution for oral administration. The composition may be dissolved in suitable solutions with added suitable colorants, flavors, stabilizing and thickening agents, artificial and natural sweeteners, and the like. In addition, the composition may further be dissolved in solution containing viscous material, such as natural or synthetic gums, resins, methylcellulose, sodium carboxymethylcellulose, or other well-known suspending agents.

In certain embodiments, the composition is applied topically or systemically or via a combination of both. The composition may be formulated in the forms of lotion, cream, gel and the like.

In one embodiment, the composition can be applied directly to the nasal cavity by conventional means, for example with a dropper, pipette or spray. The compositions may be provided in single or multi-dose form. Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin.

Furthermore, the composition may be provided in the form of a dry powder, for example a powder mix of the compound in a suitable powder base such as lactose, starch, starch derivatives such as hydroxypropylmethyl cellulose and polyvinylpyrrolidone (PVP). Conveniently, the powder carrier will form a gel in the nasal cavity. The powder composition may be presented in unit dose form for example in capsules or cartridges of, e.g., gelatin, or blister packs from which the powder may be administered by means of an inhaler.

In one embodiment, the pharmaceutical composition is provided in a unit dosage form, wherein the composition in desired form is divided into unit doses containing appropriate quantities of the active component. The unit dosage form can be a packaged preparation, the package containing discrete quantities such as packaged tablets, capsules, and powders in vials or ampoules. Moreover, the unit dosage form can be a capsule, tablet, cachet, or lozenge itself, or it can be the appropriate number of any of these in packaged form. In a preferred embodiment, tablet or capsule forms are for oral administration and liquid form are for intravenous administration and continuous infusion.

Furthermore, it would be understood by those skilled in the art that the methods described in the present invention would not only apply to treatment in a subject, but could be applied to cell cultures, organs, tissues, or individual cells in vivo or in vitro.

In one embodiment, the subject invention provides a method for inhibiting a DNA gyrase, comprising contacting the DNA gyrase with one or more compound of the subject invention. In specific embodiments, the DNA gyrase is a bacterial DNA gyrase.

In one embodiment, the present invention also provides a method for inhibiting a DNA gyrase in a pathogen, e.g., a bacterium, comprising administering an effective amount of one or more compounds to the pathogen or contacting the pathogen with an effective amount of one or more compounds of the subject invention.

In one embodiment, the subject invention provides a method for inhibiting the growth of a bacterium, the method comprising contacting the bacterium with one or more compounds of the subject invention.

In one embodiment, the subject invention also provides a method for treating a bacterial infection in a subject, comprising administering an effective amount of the compound of the subject invention or the pharmaceutical composition comprising one or more compounds according to the subject invention, to a subject in need of such treatment. In a preferred embodiment, the subject is a human.

In one embodiment, the subject invention provides a method for treating tuberculosis, the method comprising administering a compound of the subject invention or a composition of the subject invention to a subject having tuberculosis. In a preferred embodiment, the tuberculosis is MDR-TB, XDR-TB, TDR-TB, or RR-TB.

In specific embodiments, the compounds for used to treat tuberculosis are selected from compounds 229, and 259-264.

In one embodiment, the method of the subject invention can be used for determining the presence of inhibitors targeting a DNA gyrase in a sample.

Also provided are kits for screening inhibitors of DNA gyrases. The kit can comprise, for example, a circular double-stranded DNA plasmid comprising the fluorophore-quencher nucleic acid on the same strand, a DNA gyrase, wherein the kit is used to detect inhibitors of the DNA gyrase. The kits may further be used in the methods described herein. The kits may also include at least one reagent and/or instructions for their use.

Also, the kits may include one or more containers filled with reagent(s) and/or one or more molecules of the invention. The kits may also comprise a control composition. In certain embodiments, the kits may additionally include reagents and means for detecting the labels provided on the molecules of the invention. The means of allowing detection may be by conjugation of detectable labels or substrates, such as fluorescent compounds, enzymes, radioisotopes, heavy atoms, reporter genes, luminescent compounds, etc. As it would be understood by those skilled in the art, additional detection or labeling methodologies may be used in the kits provided.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

EXAMPLES

Methods

SDFQ HTS Assay

SDFQ HTS primary assay using pAB1_FL905 was performed in 2 μL of (1×DNA gyrase buffer: 20 mM Tris-Acetate pH 7.9, 50 mM KAc, 10 mM $MgCl_2$, 2 mM DTT, 1 mM ATP, 0.1 mg/mL BSA). The following is the procedure: 1) Using the BioRAPTR, dispensed 1 μL of *E. coli* DNA Gyrase (350 ng/μL) with a final conc. in assay 175 ng/μl. 2) Using the BioRAPTR, dispensed 1 μL of DNA pAB1_FL905 (6.425 ng/μL)—final conc in assay is 3.2125 ng/μL in assay. 3) Spun plate at 800 rpm for 30 seconds. 4)

Incubated the plate at 37° C. for 2 hours in the dark and read the plate on the Envision measuring fluorescence (excitation@484 nm, emission@Em520).

SDFQ HTS secondary assay using pAB1_FL924 was performed in 2 μL of (1×DNA gyrase buffer: 20 mM Tris-Acetate pH 7.9, 50 mM KAc, 10 mM $MgCl_2$, 2 mM DTT, 1 mM ATP, 0.1 mg/mL BSA). The following is the procedure: 1) Using the BioRAPTR, dispensed 1 μL of *E. coli* DNA Gyrase (350 ng/μL) with a final conc. in assay 175 ng/μl. 2) Using the BioRAPTR, dispensed 1 μL of DNA pAB1_FL924 (6.425 ng/μL)—final cone in assay is 3.2125 ng/μL in assay. 3) Spun plate at 800 rpm for 30 seconds. 4) Incubated the plate at 37° C. for 2 hours in the dark and read the plate on the Envision measuring fluorescence (excitation@531 nm, emission@Em595).

SDFQ-Based DNA Gyrase Inhibition Assays

SDFQ-based DNA gyrase inhibition assays were performed in 30 μL of 1×gyrase buffer (35 mM Tris-HCl, 24 mM KCl, 4 mM $MgCl_2$, 2 mM DTT, 1.75 mM ATP, 0.1 mg/mL BSA, 6.5% glycerol, pH7.5) containing 400 ng of rx pAB1_FL905 at 37° C. 100 ng of DNA gyrase was used to supercoil the rx pAB1_FL905 in the presence of different concentrations of a gyrase inhibitor. The fluorescence intensity at $\lambda_{em}$=521 nm was monitored with $\lambda_{ex}$=494 nm in a microplate reader. The IC50 values were estimated by nonlinear fitting of the following equation:

$$F = F_{min} + \frac{F_{max} - F_{min}}{1 + 10^{(log(IC50) - x)P}}$$

where F is the fluorescence intensity at the x concentration of an inhibitor. $F_{max}$ and $F_{min}$ are the maximum and minimum fluorescence of the DNA sample, respectively. P is a slope parameter.

Agarose Gel-Based DNA Gyrase Inhibition Assays

Agarose gel-based DNA gyrase inhibition assays were performed in 30 μL of 1×gyrase buffer (35 mM Tris-HCl, 24 mM KCl, 4 mM $MgCl_2$, 2 mM DTT, 1.75 mM ATP, 0.1 mg/mL BSA, 6.5% glycerol, pH7.5) containing 400 ng of rx pAB1 at 37° C. 100 ng of DNA gyrase was used to supercoil the rx pAB1 in the presence of different concentrations of a gyrase inhibitor. After 15 minutes of incubation with the inhibitor at 37° C., all reactions were stopped with 1 μL of stop solution (3% SDS and 250 mM EDTA). Samples were analyzed by electrophoresis in 1% w/v agarose gels followed by ethidium bromide staining and photographed under UV light.

DNA Gyrase Mediated DNA Cleavage Assay.

250 ng of supercoiled pBR322 plasmid were incubated with 50 nM of *E. coli* DNA gyrase in reactions containing 35 mM Tris-HCl, 24 mM KCl, 4 mM MgCl2, 2 mM DTT, 0.1 mg/mL BSA, 6.5% glycerol, and 1.75 mM ATP, in presence of 200 μM of compounds, at 37° C. for 15 min. Then, 0.2% (w/v) of SDS and 0.1 mg/mL proteinase K were added, and samples were incubated at 37° C. for 1 h. Ciprofloxacin (200 μM) was used as a positive control. Samples were examined by electrophoresis in 1% w/v agarose gel containing 0.5 μg/mL ethidium bromide and photographed under UV light.

Minimum Inhibitory Concentrations Assays.

Antibacterial minimum inhibitory concentrations (MICs) were obtained from three independent experiments using broth microdilution methods in 96-well plates according to Clinical and Laboratory Standards Institute guidelines. Cells were culture from singles colonies in MHIIB medium for 24 h at 37° C. in agitation (200 RPM). The cultures were then diluted using the same media to reach an $OD_{600}$ of 0.1. Then, 50 μL of the diluted cultures were added to the plates holding 50 μL of serially diluted compounds in MHIIB. The plates were incubated at 37° C. for 20 h. The starting inoculum was fixated to $10^5$ colony-forming units per ml. The MIC was the lowest dilution of compounds, with no differences in $OD_{600}$ values compared to the wells without cells. Strains *S. aureus* (ATCC 14775), MRSA (ATCC BAA44), *B. subtilis* (ATCC 6633), *E. coli* (ATCC 25922) and *E. coli* imp were used to determine the MICs.

*E. coli* DNA Gyrase ATPase Assays

*E. coli* DNA gyrase ATPase assays were performed in 60 μL of 1×gyrase ATPase buffer (10 mM Tris·HCl (pH 7.5), 0.2 mM EDTA, 1 mM magnesium chloride, 1 mM DTT, and 2% (w/v) glycerol) containing 50 nM *E. coli* DNA gyrase, 200 ng rx pAB1, 0.8 mM Phosphoenol pyruvate, 1.2 units of Pyruvate kinase, 1.7 units of lactate dehydrogenase, and 0.4 mM of NADH at 37° C. After the reaction mixtures are incubated on ice for 5 minutes, 2 mM of ATP is added to initiate the reaction. Absorbance at OD340 nm is monitored for up to 30 minutes at 37° C. in a spectrophotometer.

Example 1. Establish the SDFQ HTS Assay and Screen the LOPAC Library

Figure 3B:
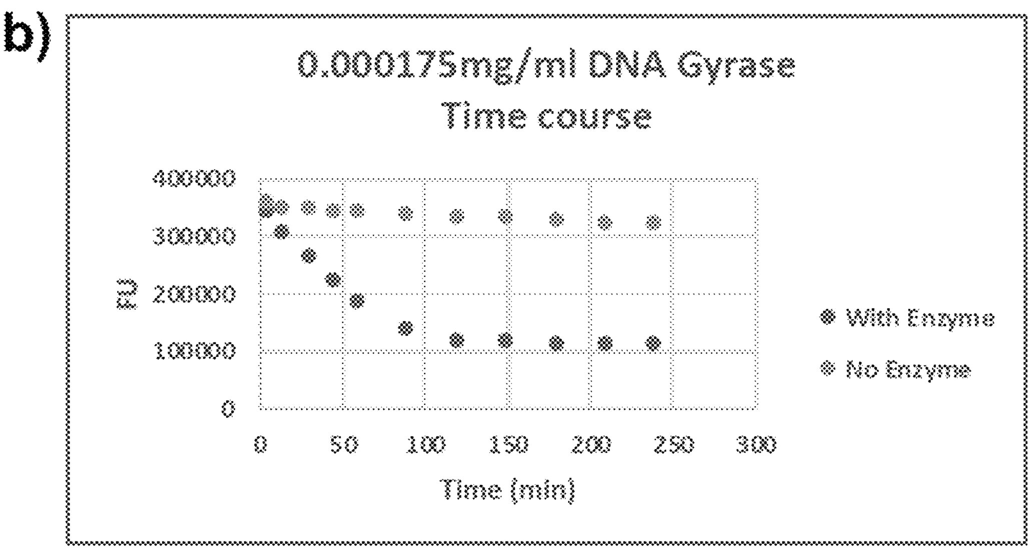
Figure 3C:
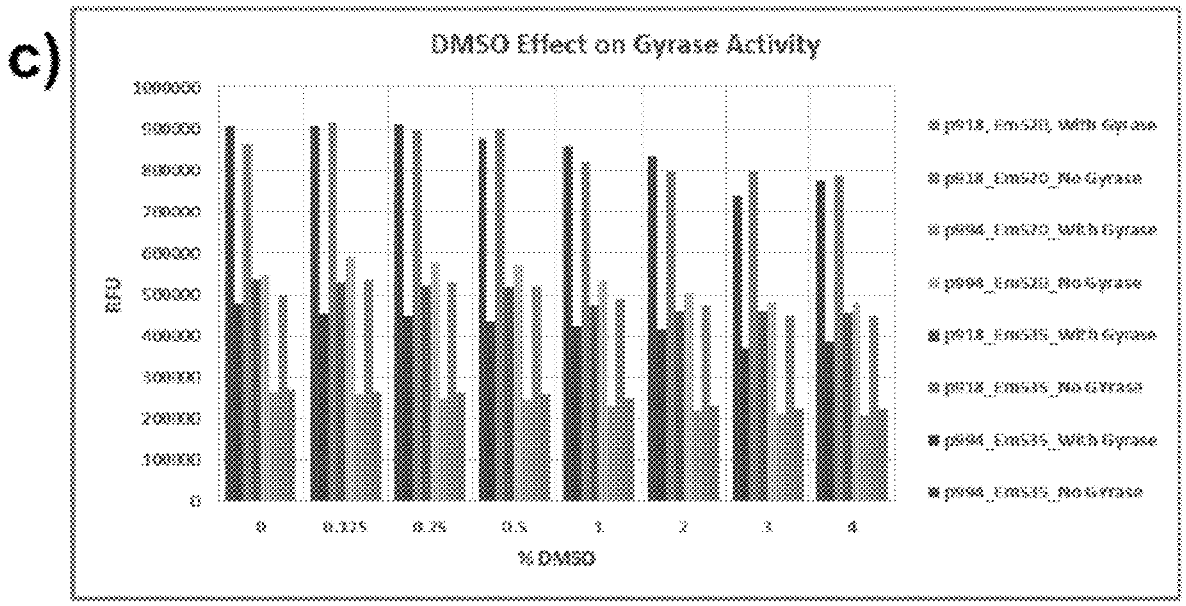
Figure 4:
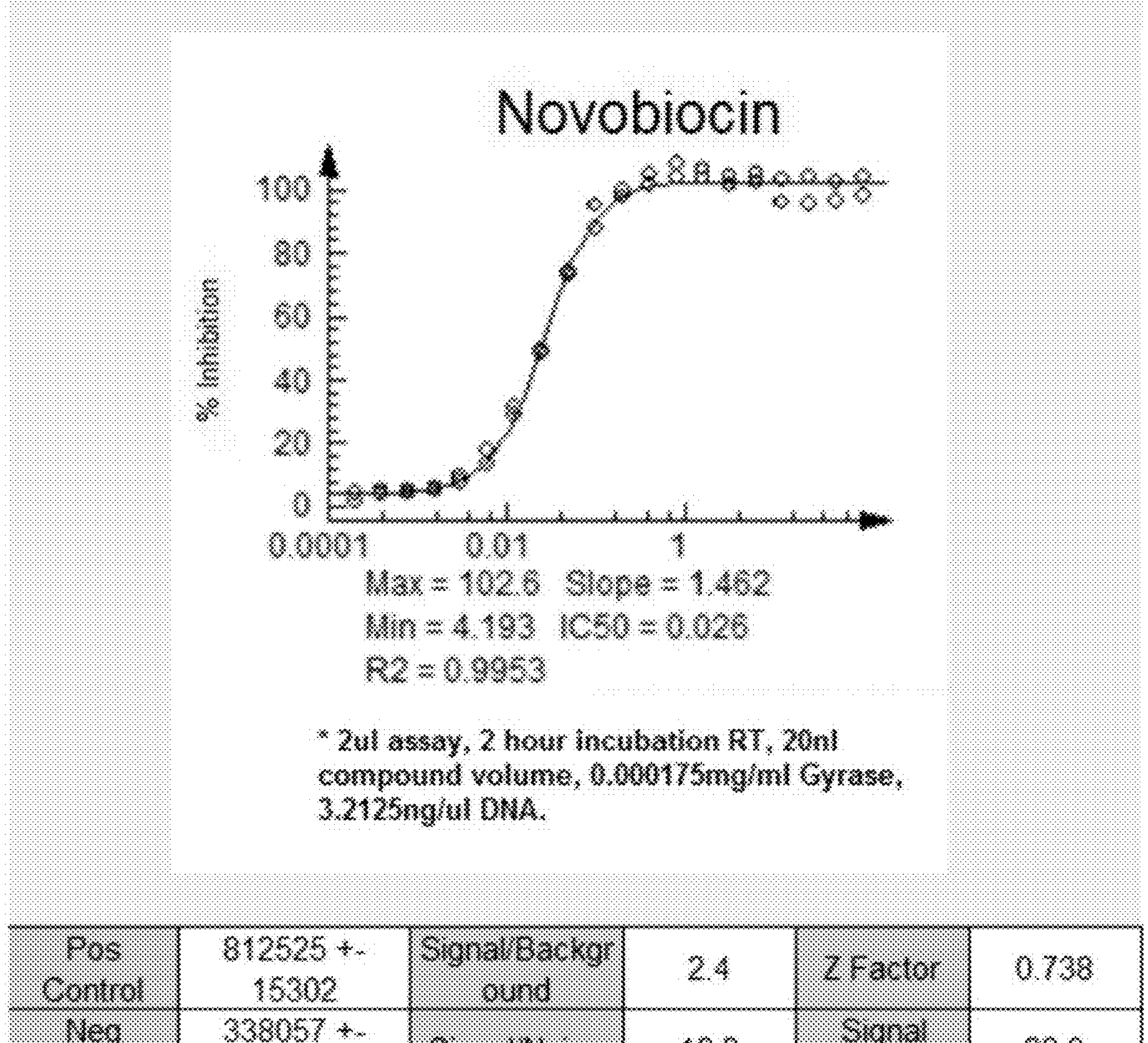
FIG. 4 shows that Novobiocin potently inhibited *E. coli* DNA gyrase activities determined by SDFQ gyrase assays in 1×gyrase buffer (2 μL) using 3.21 ng/μL of pAB1_FL905 and 175 ng/μL of *E. coli* DNA gyrase. Fluorescence was measured using λex=484 nm and λe=520 nm. The inhibition $IC_{50}$ was determined to be 26 nM.

Optimal conditions were determined for the miniaturized, automated SDFQ HTS primary assay of *E. coli* DNA gyrase in the 1536-well plate format using rx plasmid pAB1_FL905 in 1×DNA gyrase buffer (20 mM Tris-Acetate pH 7.9, 50 mM KAc, 10 mM $MgCl_2$, 2 mM DTT, 1 mM ATP, 0.1 mg/mL BSA) (FIGS. 2 and 3). After a series of experiments, 2 μL of a total of volume, 120 min incubation time, 175 ng/μl of *E. coli* DNA gyrase, and 3.21 ng/μL of pAB1_FL905 were chosen for the assay. The fluorescence intensity was measured using excitation wavelength of 484 nm and emission wavelength of 520 nm. The assay tolerated up to 4% DMSO without any significant change in signal. A known bacterial DNA gyrase inhibitor, novobiocin, was used for the positive control. Results in FIG. 4 clearly demonstrate that novobiocin is a strong inhibitor of *E. coli* DNA gyrase with an $IC_{50}$ of 26 nM. Similar conditions were also obtained for the secondary SDFQ assay by which pAB1_FL924 was used as the DNA substrate (FIG. 5). The fluorescence intensity was measured using excitation wavelength of 531 nm and emission wavelength of 595 nm.

Figure 6:
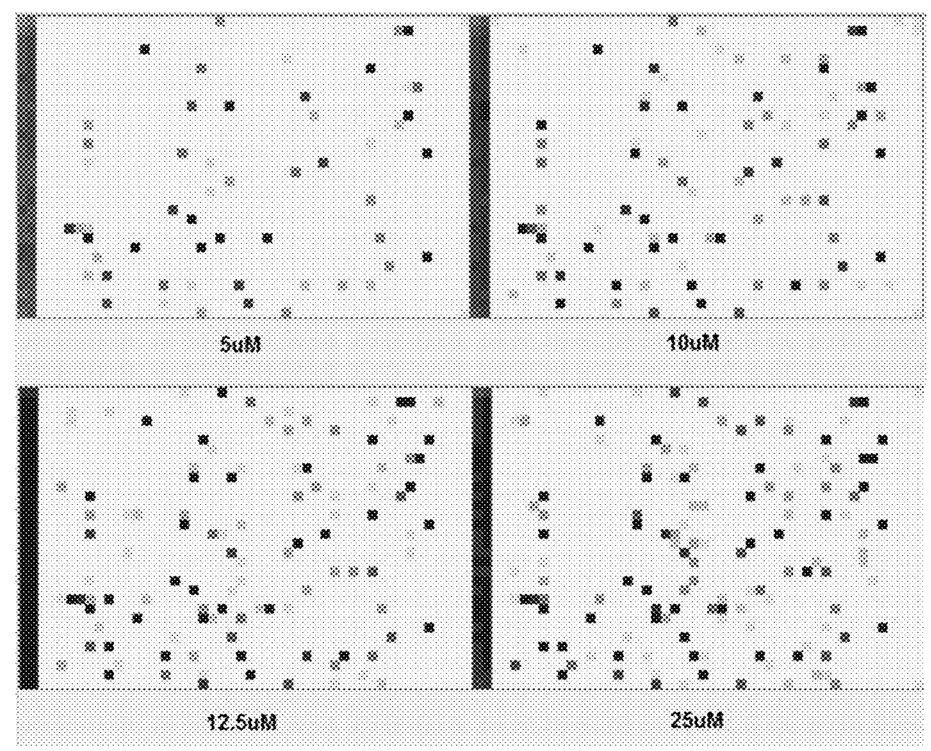
FIG. 6 shows the visualization of the SDFQ assays screening the LOPAC library using different concentrations of compounds. The images were taken using the CCD camera in the instrument.
Figure 7A:
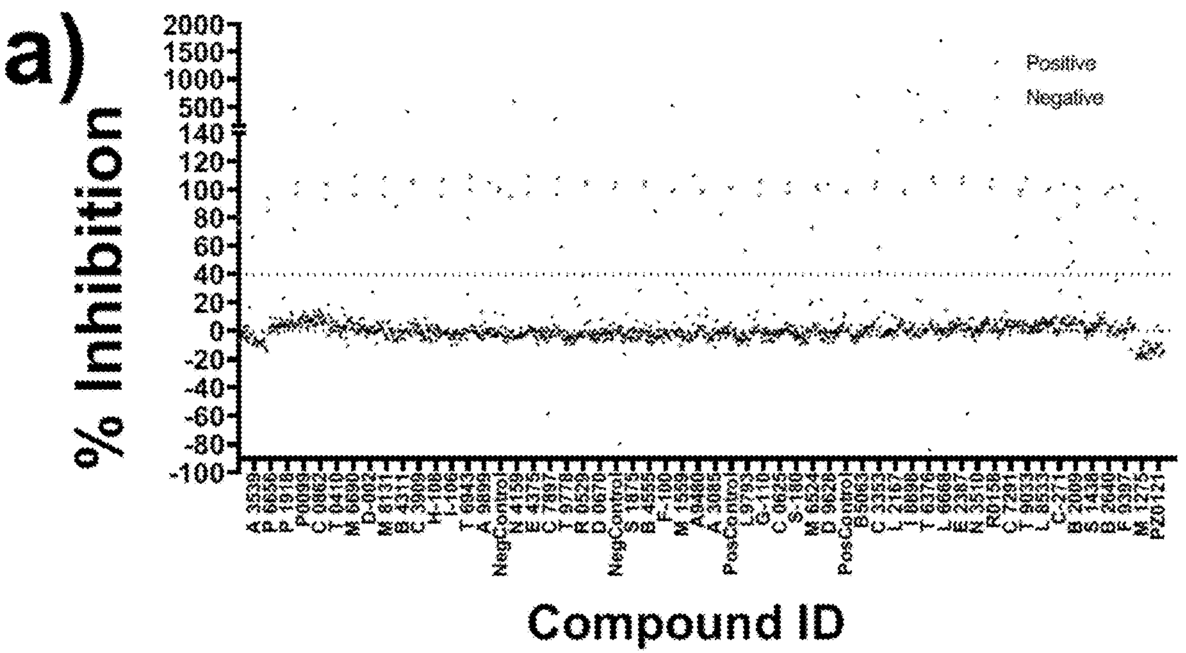
FIGS. 7A-7B show the screening of the LOPAC library. (A) The pilot screening of the LOPAC library for *E. coli* DNA gyrase inhibitors using the miniaturized, automated SDFQ HTS primary assay in the 1536-well plate format. DMSO and novobiocin were used as negative and positive controls, respectively. The dotted line represents the 40% inhibition. (B) 41 compounds have >40% inhibition activities against *E. coli* DNA gyrase.
Figure 7B:
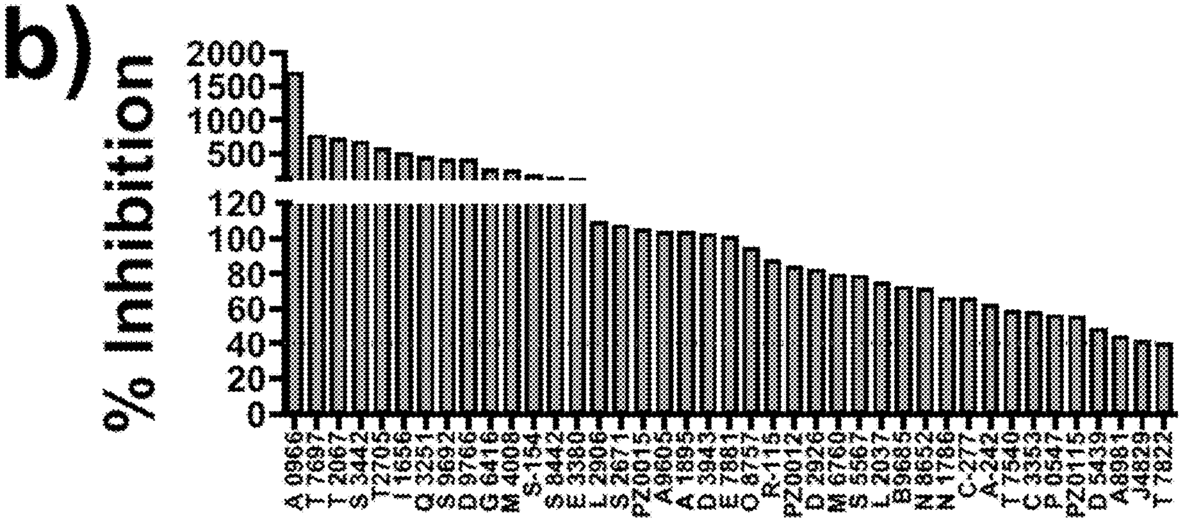

To validate HTS readiness, the Sigma LOPAC1280 library of 1,280 pharmacologically active compounds were screened. FIGS. 6 and 7 show the results at 5 μM with the following statistics: Z'=0.70, S/B=2.5, and 41 hits/compounds with more than 40% inhibition activities and a hit rate of ~3.2% (FIG. 7). The hits include 3 known gyrase inhibitors (lomefloxacin, ofloxacin, and trovafloxacin) and several DNA topoisomerase II inhibitors such as suramin, aurintricarboxylic acid, and emodin.

Although the Sigma LOPAC1280 library carries two additional DNA gyrase inhibitors, nalidixic acid and oxolinic acid, their inhibition $IC_{50}$ against *E. coli* DNA gyrase is more than 30 μM, it is not surprising that they are not included in the hit list. Some compounds per se have very strong fluorescence, which results in more than 100% inhibition against *E. coli* DNA gyrase (FIG. 7). They are false positives and should be excluded from the hit list.

Unexpectedly, two new *E. coli* gyrase inhibitors were found from the pilot screen: chloro-IB-MECA and metergoline. Their inhibition against *E. coli* DNA gyrase were confirmed by agarose gel-based DNA gyrase assays (FIG.

Figure 8A:
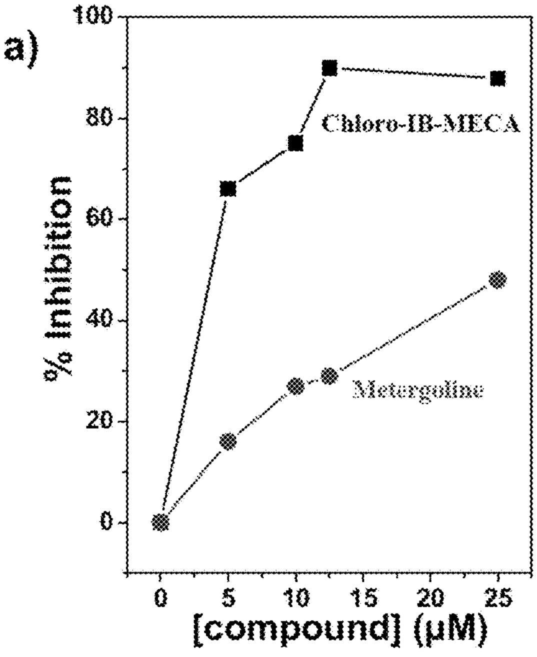
Figure 10A:
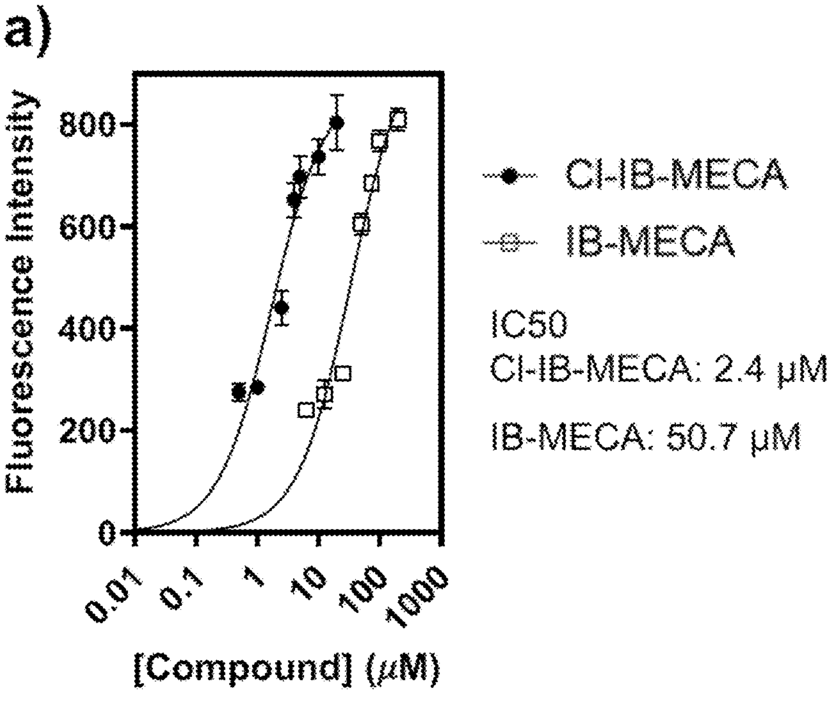
FIGS. 10A-10B show the inhibition of *E. coli* DNA gyrase activities by chloro-IB-MECA, IB-MECA, and AB-MECA. (A) The SDFQ-based DNA gyrase assays. (B) the agarose gel-based DNA gyrase assays. Rx and Sc represent relaxed and supercoiled pABL.
Figure 10B:
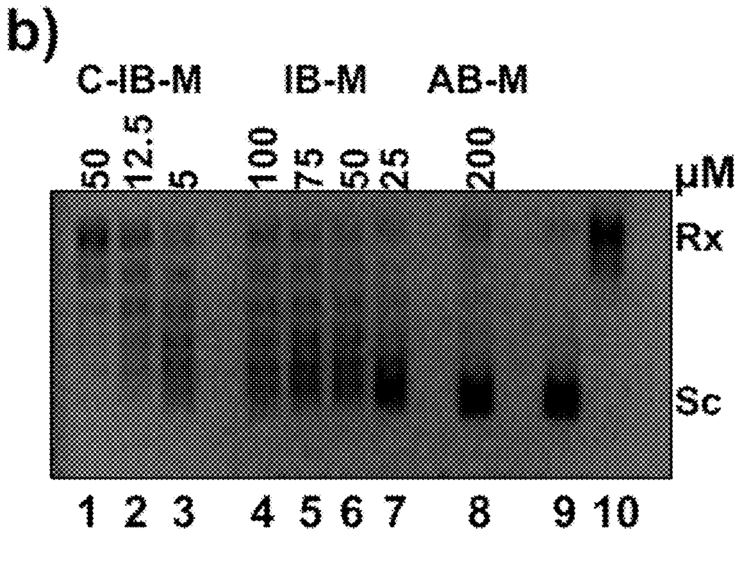

8). Metergoline (FIG. 9) is a dopamine agonist and serotonin antagonist, and inhibits gyrase activities at 100 and 200 μM (FIG. 8). Chloro-IB-MECA (FIG. 9) is an adenosine analogue and an antagonist of adenosine A3 receptors. It potently inhibits *E. coli* DNA gyrase activities with an $IC_{50}$ of 2.4 μM (FIG. 10).

Figure 12C:
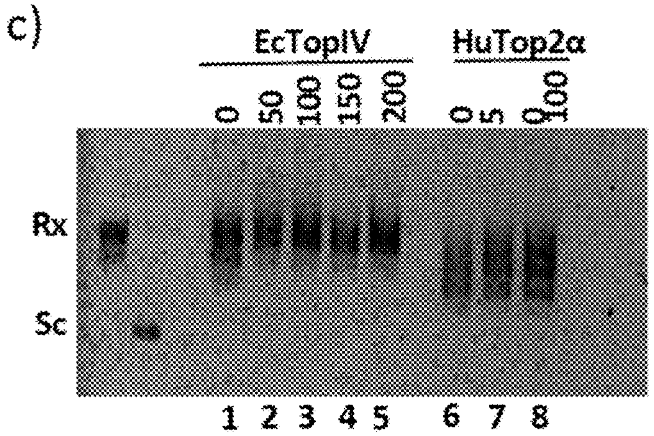
Figure 12D:
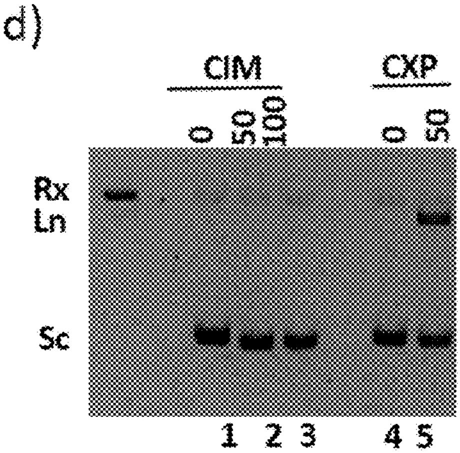

The LOPAC library also contains two similar adenosine analogues: IB-MECA and AB-MECA (FIG. 9). IB-MECA also inhibits *E. coli* DNA gyrase activities with an $IC_{50}$ of 50.7 μM (FIG. 10). AB-MECA does not inhibit *E. coli* gyrase activities (FIG. 10). The ATPase assays of *E. coli* DNA gyrase show that chloro-IB-MECA and IB-MECA are the ATP competitive inhibitors of *E. coli* DNA gyrase (FIG. 11). Interestingly, chloro-IB-MECA, IB-MECA, and AB-MECA did not inhibit Mtb DNA gyrase activities. They also did not inhibit *E. coli* DNA topoisomerase I, *E. coli* DNA topoisomerase IV, human DNA topoisomerase I, and human DNA topoisomerase IIα (FIG. 12). The experimental results from the pilot screen of the LOPAC1280 library and the assay statistics demonstrate that our SDFQ-based assay is HTS-ready for an HTS campaign to identify bacterial DNA gyrase inhibitors.

Example 2. Screen the NCATS Compound LIBRARY

Figure 13:
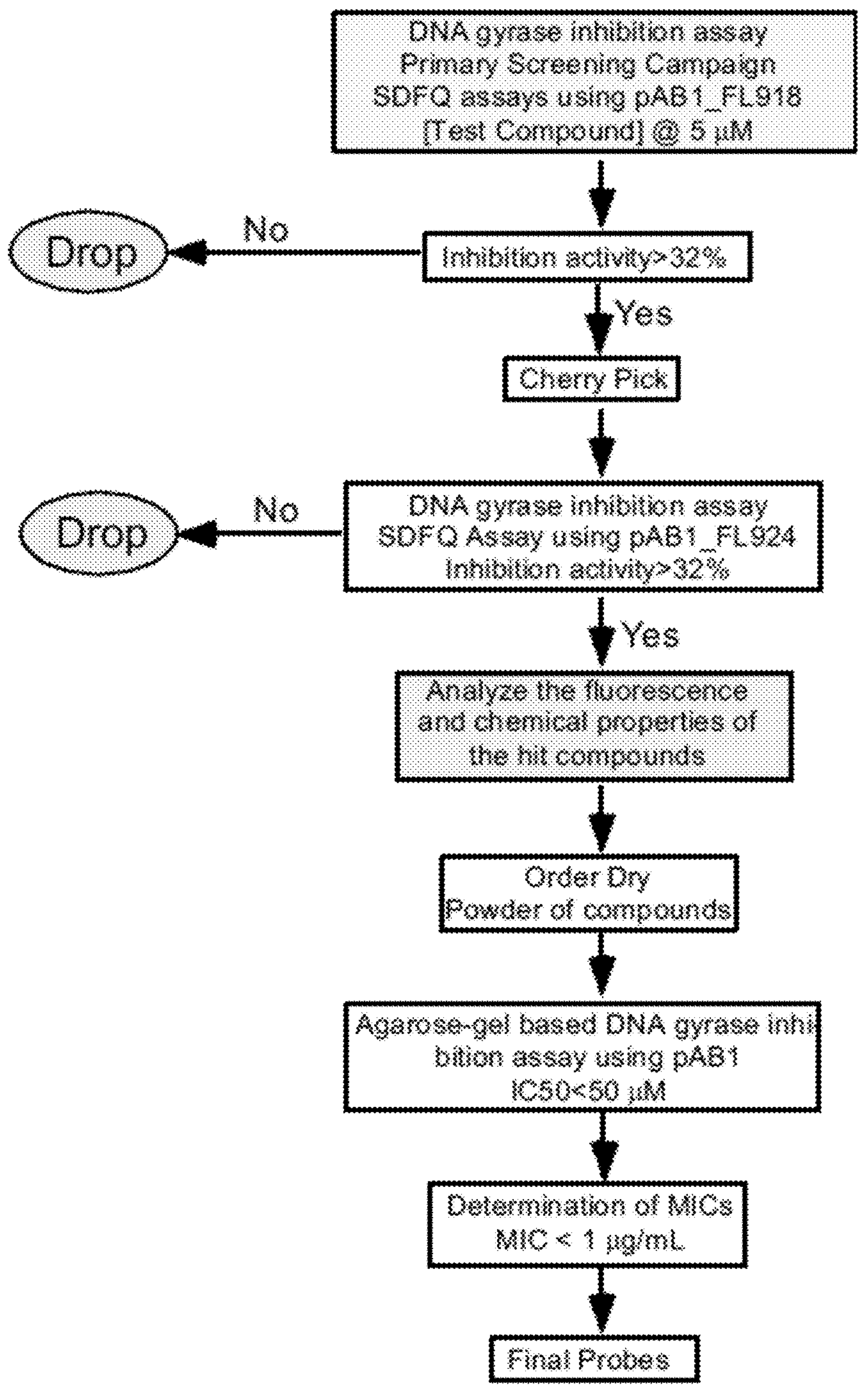
FIG. 13 shows the screen funnel to identify new bacterial DNA gyrase inhibitors.
Figure 14A:
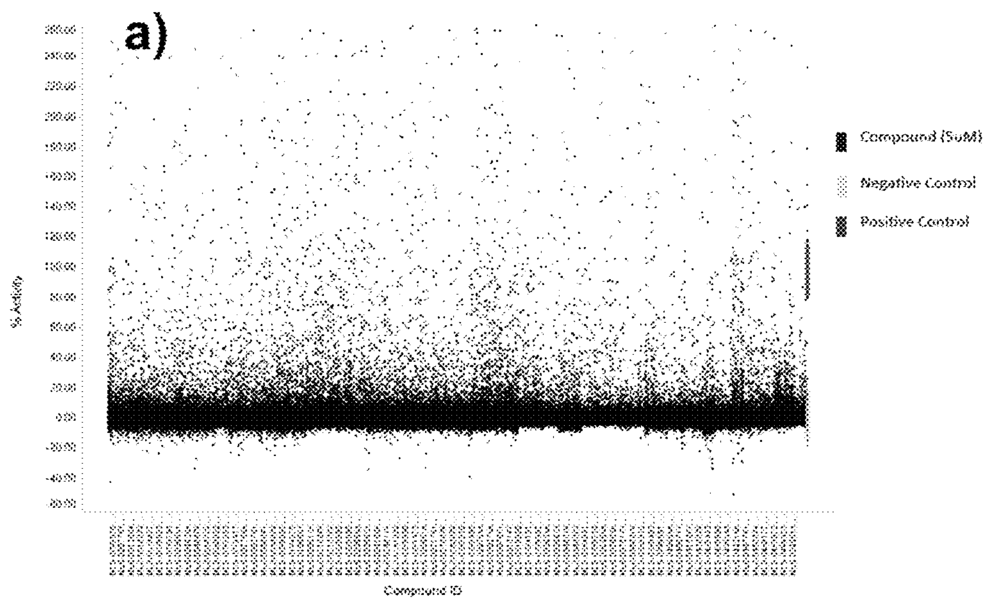
FIGS. 14A-14B show the screening of the NCATS compound library for *E. coli* DNA gyrase inhibitors. DMSO and novobiocin were used as negative and positive controls, respectively. The data is corrected and zoomed. 531 compounds >250% activities not shown. (A) and (B) are 2- and 3-dimensional views, respectively.
Figure 14B:
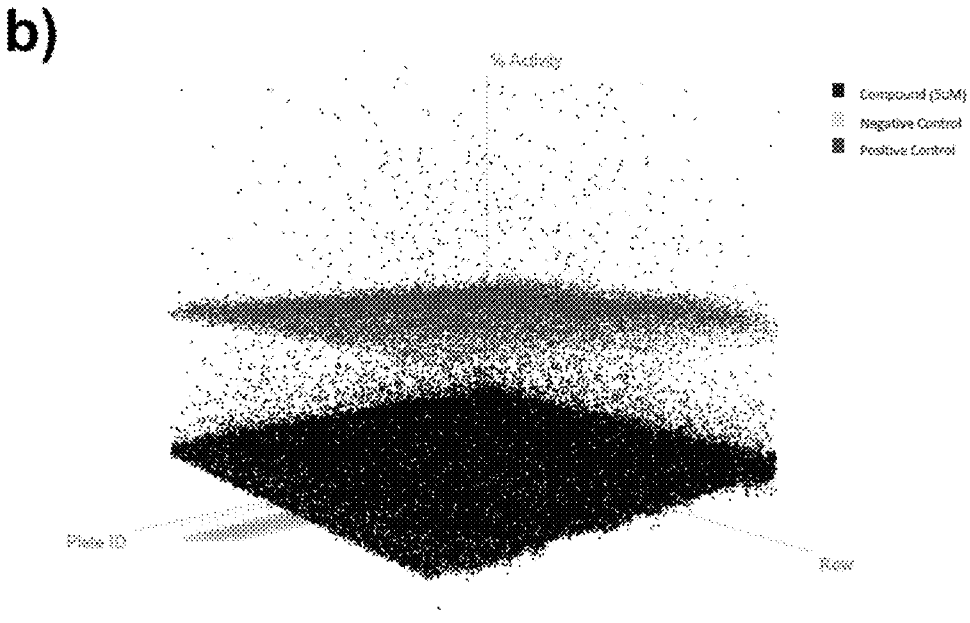

The NCATS compound library was screened using the established SDFQ HTS assay (FIG. 13). The following are the statistics after screening 370,620 compounds in 282 plates at 5 μM: Z'≈0.81, RZ'≈0.83, and S/B≈2.7. The screening results are shown in FIG. 14. 2,891 compounds have more than 40% inhibition activities against *E. coli* DNA gyrase with a hit rate of 0.78. After retesting the 2,891 compounds in the primary and secondary assays, 2,244 compounds have more than 32% inhibition activities against *E. coli* DNA gyrase in both the primary and secondary HTS assays. The fluorescence results show that some compounds have high fluorescence at the wavelengths used for the signal detection which gives more than 100% inhibition activities (FIG. 14). Apparently, these high fluorescent compounds are false positives and should be excluded from the potential DNA gyrase inhibitors.

Figure 15:
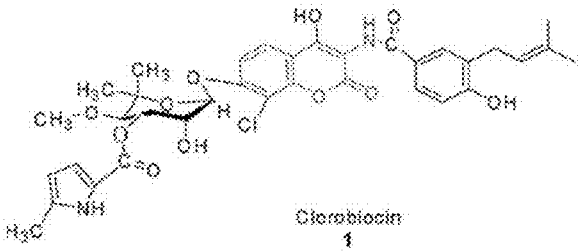
FIG. 15 shows chemical structures of novobiocin, chlorobiocin, bithiazoles, and ciprofloxacin.
Figure 15:
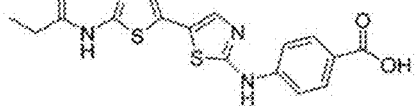
Figure 15:
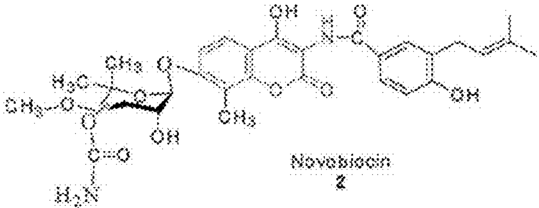
Figure 15:
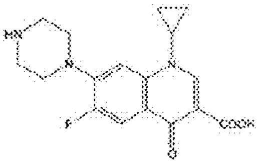
Figure 16:
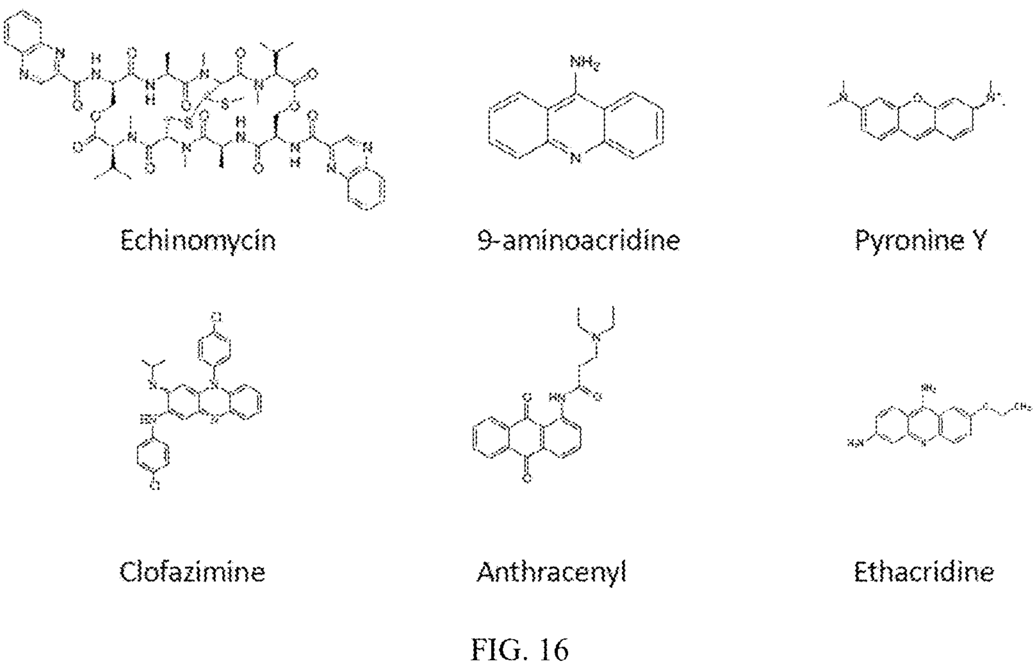
FIG. 16 shows chemical structures of six DNA intercalators.
Figure 17:
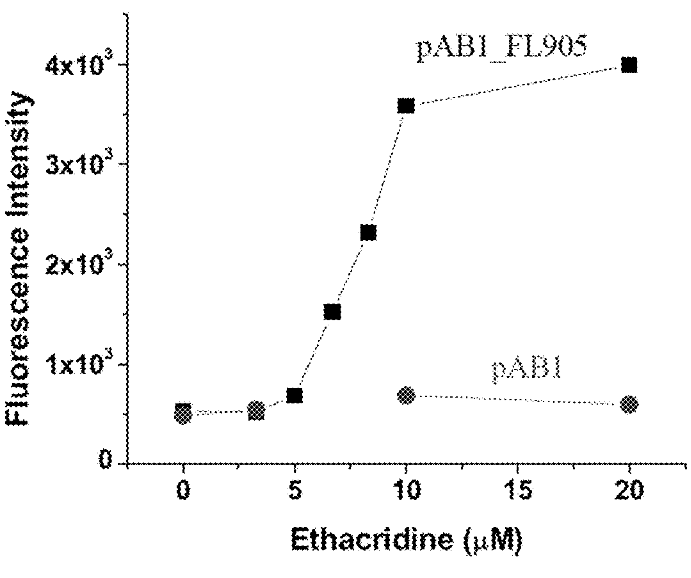
FIG. 17 shows that the fluorescence intensity was significantly increased after DNA intercalator ethacridine intercalated and unwound the se pAB1_FL905 (black squares). In contrast, ethacridine does not have fluorescence in the presence plasmid pAB1 at the concentrations used in this experiment.
Figure 18A:
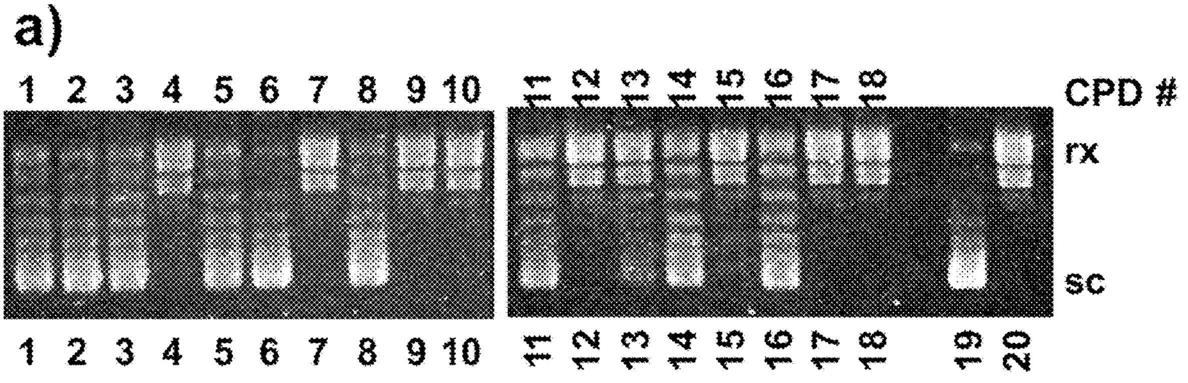
FIGS. 18A-18E show the screening of compounds 1-87 using agarose gel-based DNA gyrase assays in 1×gyrase buffer. 200 μM of compounds were used. Compounds 4, 7, 9, 10, 12, 15, 17, 18, 19, 21, 22, 23, 24, 25, 27, 29, 31, 33, 35, 36, 38, 40, 41, 42, 44, 46, 47, 48, 49, 53, 58, 60, 62, 63, 64, 70, 79, and 83 completely inhibited *E. coli* DNA gyrase activities. Compounds 13, 28, 45, 51, 54, 55, 56, 57, 61, 65, 68, and 82 almost completely inhibited *E. coli* DNA gyrase activities.
Figure 18B:
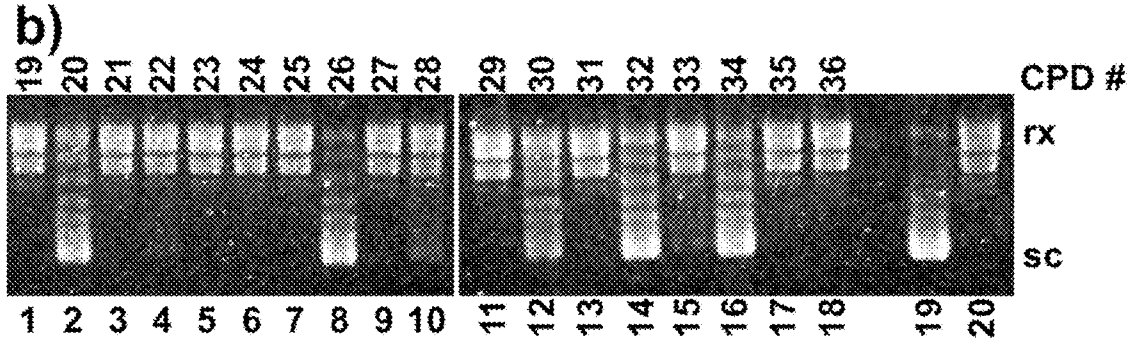
Figure 18C:
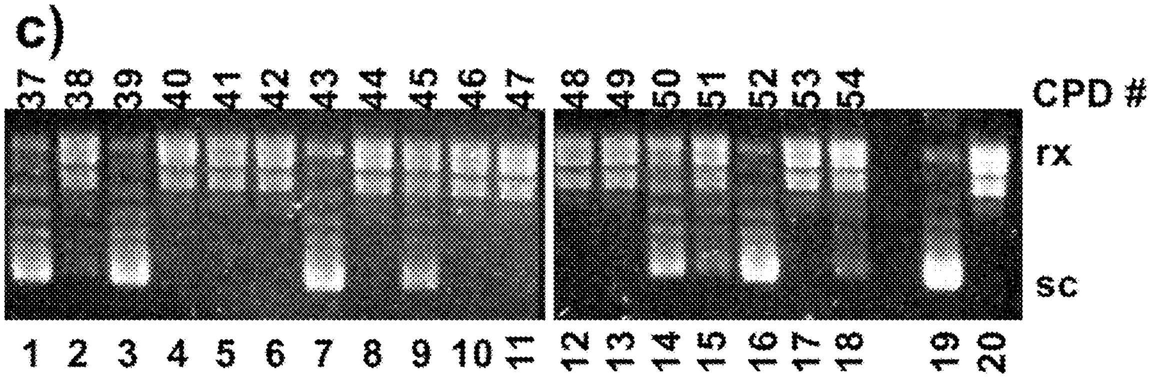
Figure 18D:
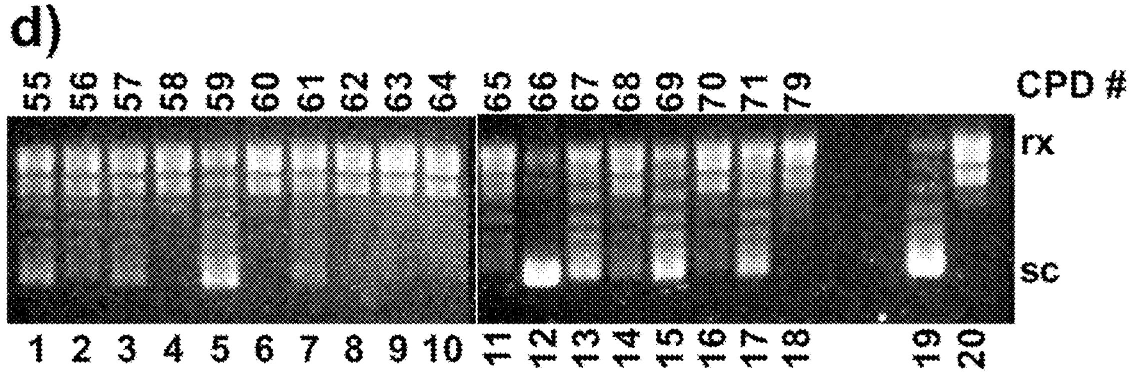
Figure 18E:
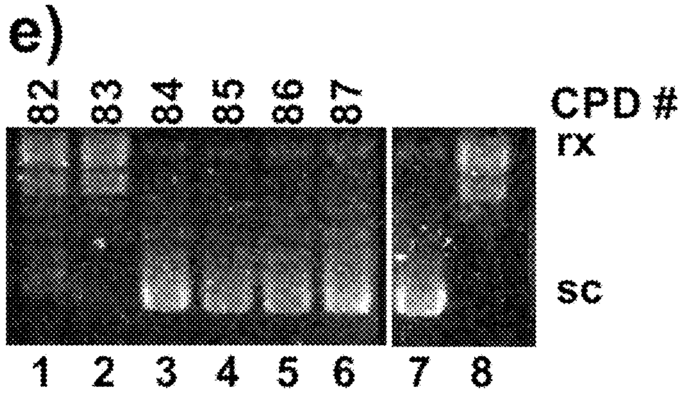
Figure 19A:
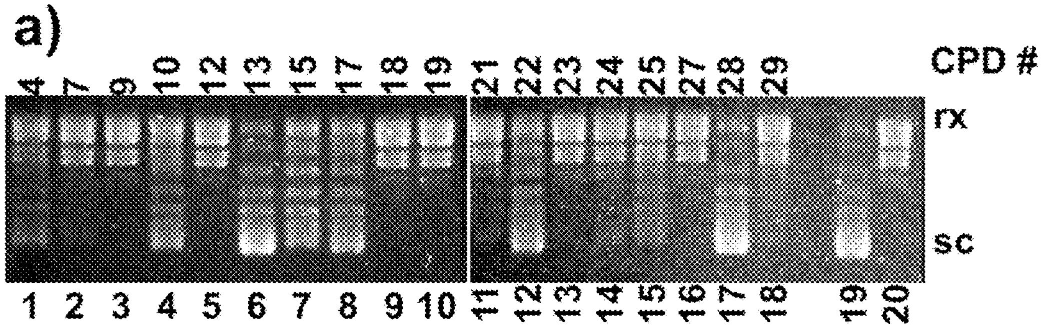
FIGS. 19A-19C show the screening of compounds 1-87 using agarose gel-based DNA gyrase assays in 1×gyrase buffer. 50 μM of compounds were used. Compounds 7, 9, 12, 18, 19, 21, 23, 24, 27, 29, 35, 36, 41, 42, 47, and 48 completely inhibited *E. coli* DNA gyrase activities. Compounds 14, 25, 49, 53, 62, and 83 almost completely inhibited *E. coli* DNA gyrase activities.
Figure 19B:
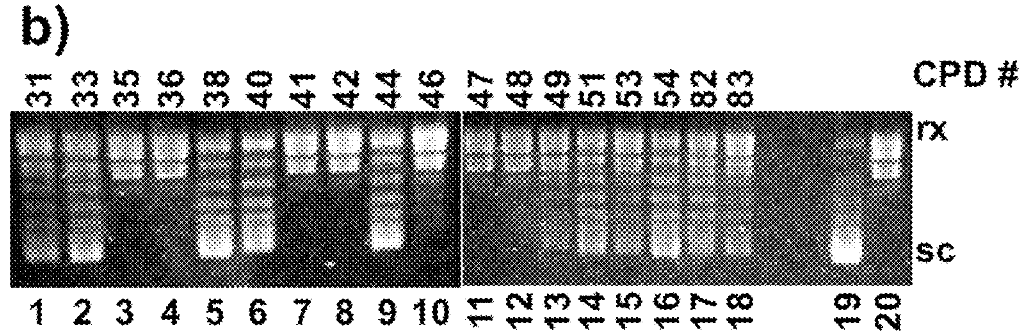
Figure 19C:
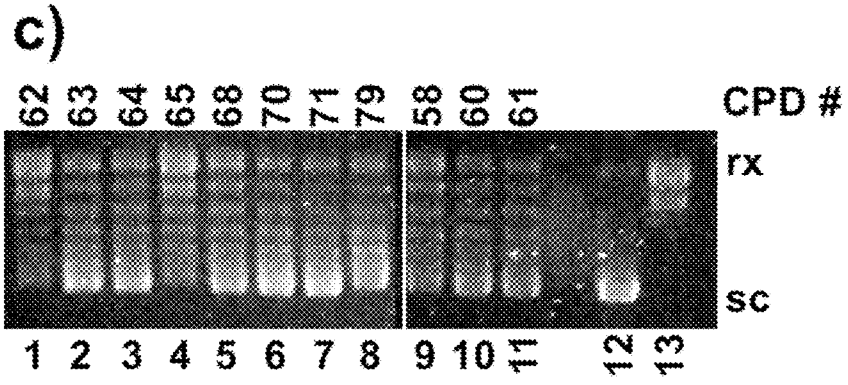
Figure 20A:
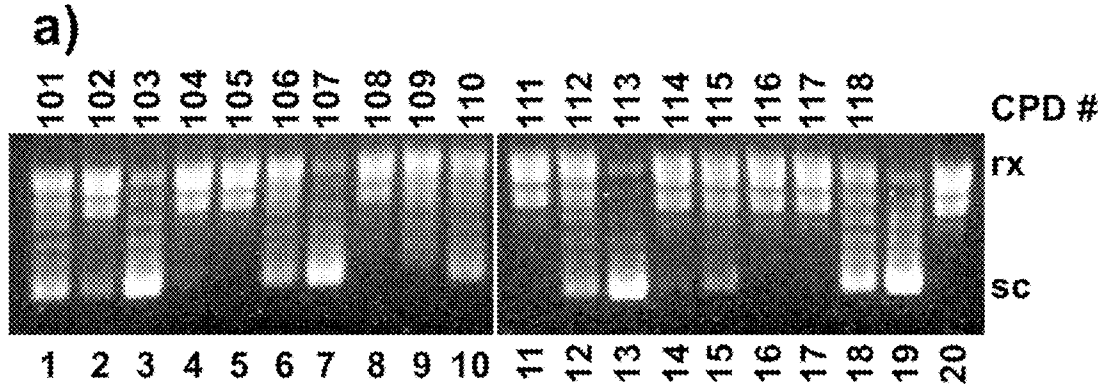
FIGS. 20A-20F show the screening of compounds 101-192 using agarose gel-based DNA gyrase assays in 1×gyrase buffer. 50 μM of compounds were used. Compounds 102, 104, 105, 108, 109, 111, 114, 116, 117, 119, 120, 121, 123, 124, 125, 126, 127, 128, 132, 135, 149, 154, 155, 157, 159, 161, 163, 165, 169, 171, 173, 176, 178, 180, 189, and 192 completely inhibited *E. coli* DNA gyrase activities. Compounds 106, 110, 112, 122, 129, 130, 131, 141, 144, 167, 168, and 184 potently inhibited *E. coli* DNA gyrase activities.
Figure 20B:
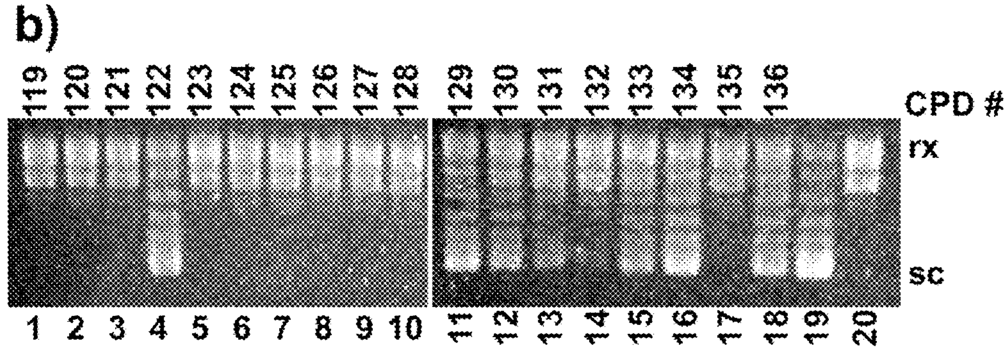
Figure 20C:
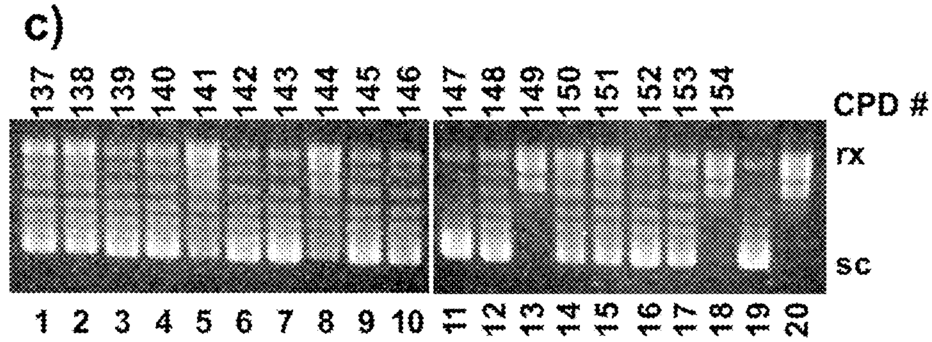
Figure 20D:
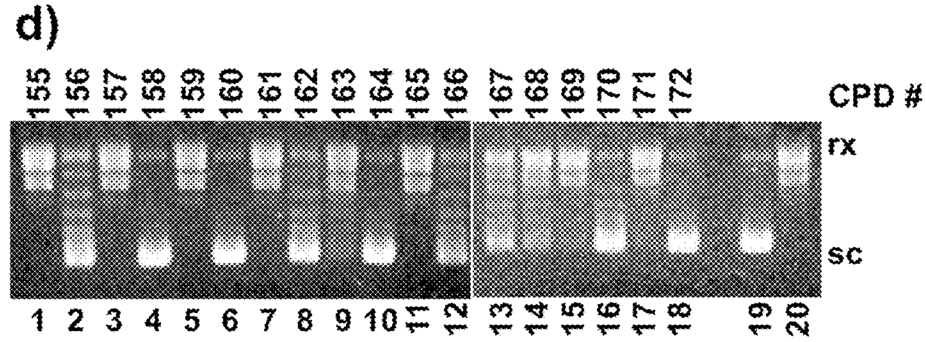
Figure 20E:
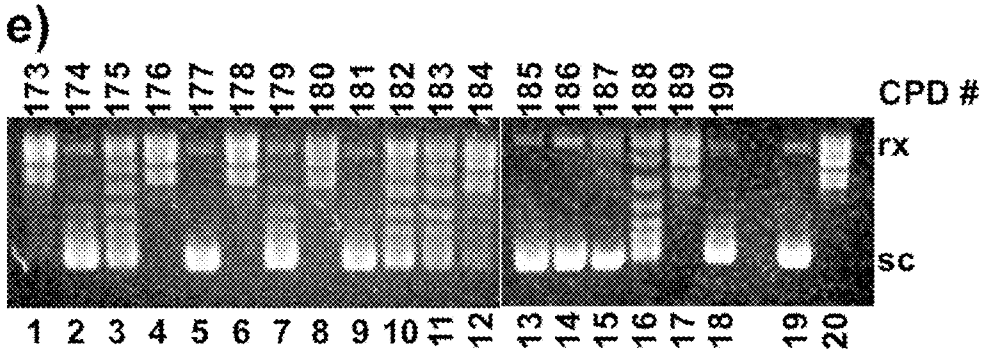
Figure 20F:
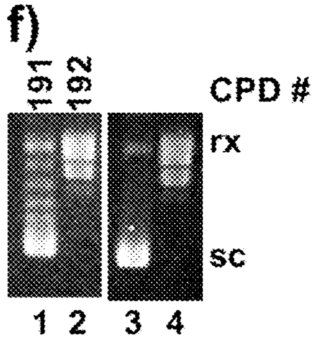
Figure 21A:
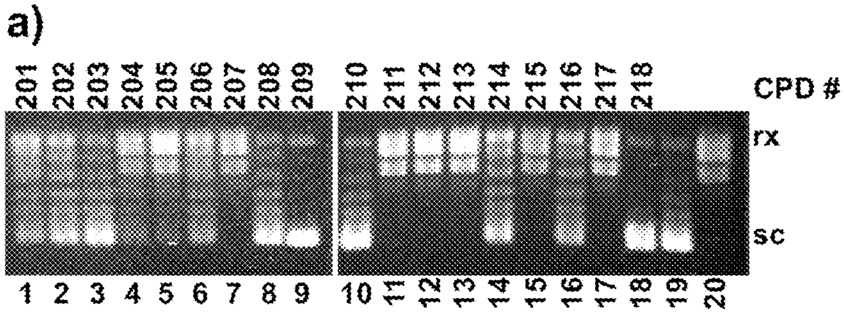
FIGS. 21A-21D show the screening of compounds 201-258 using agarose gel-based DNA gyrase assays in 1×gyrase buffer. 200 μM of compounds were used. Compounds 207, 211, 212, 213, 215, 217, 222, 224, 225, 229, 232, 236, 237, 238, 239, 240, 241, 242, 246, 247, 248, 249, 250, 253, 255, 256, 257, and 258 completely inhibited *E. coli* DNA gyrase activities. Compounds 217, 236, 237, 238, 239, 240, 241, 246, 247, 248, 249, 255, 257 and 258 are DNA intercalators. Compounds 204, 205, 206, 227, and 228 potently inhibited *E. coli* DNA gyrase activities.
Figure 21B:
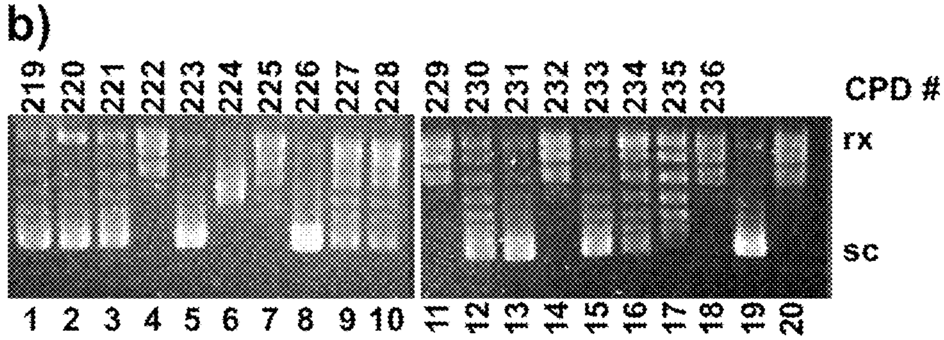
Figure 21C:
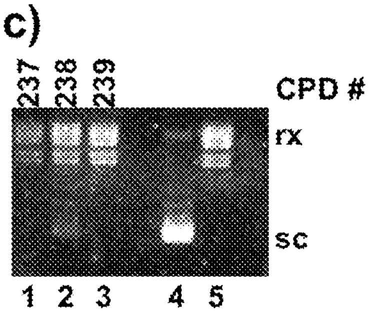
Figure 21D:
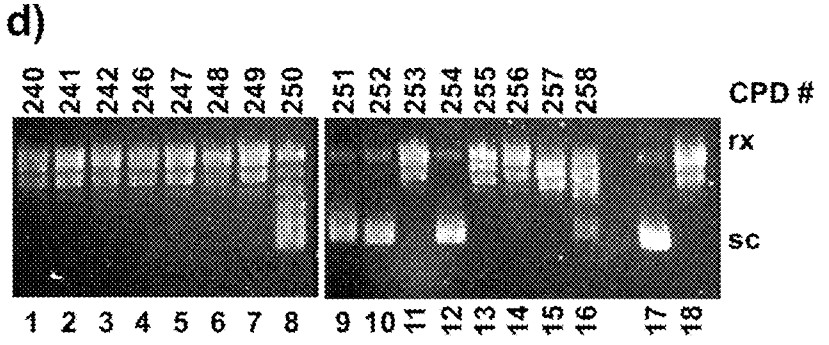
Figure 22A:
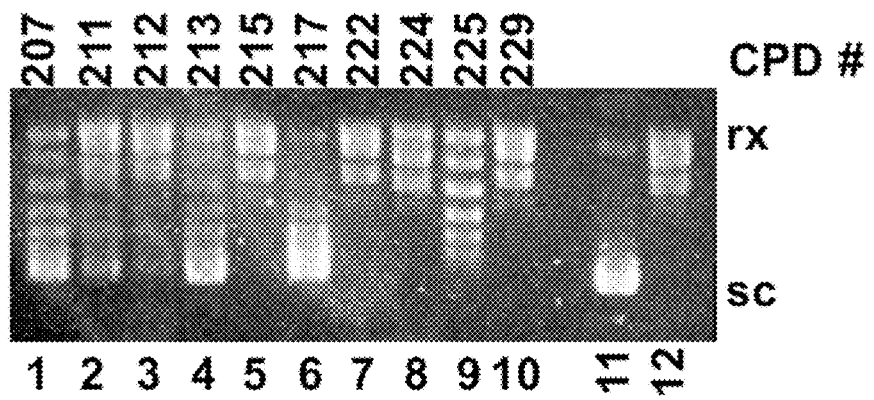
FIGS. 22A-22B show the screening of compounds 201-258 using agarose gel-based DNA gyrase assays in 1×gyrase buffer. 50 μM of compounds were used. Compounds 212, 215, 222, 224, 225, 229, and 236 completely inhibited *E. coli* DNA gyrase activities. Compound 225 is a known antibiotic mithramycin or variamycin or Plicamycin. Compounds 236 is a DNA intercalator. Compound 207, 211, and 232 inhibited *E. coli* DNA gyrase activities.
Figure 22B:
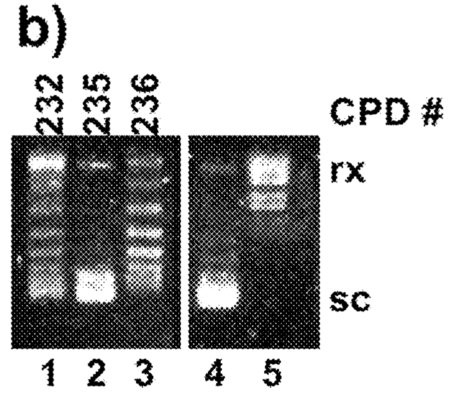

The initial analysis focuses on the 218 compounds that have the gyrase inhibition activities of less than 120% and more than 50% in both the primary and secondary assays. These compounds include 25 known DNA gyrase inhibitors, such as novobiocin and ciprofloxacin (11.5%; FIG. 15) and 81 DNA intercalators or potential DNA intercalators, such as 9-aminoacridine, echinomycin, and several anthracyclines (37.2%; FIG. 16). DNA intercalation significantly unwinds and relaxes pAB1_FL905 which results in the high fluorescence output even after pAB1_FL905 is supercoiled by *E. coli* DNA gyrase (FIG. 17). These DNA intercalators are also false positives and should be excluded from the potential DNA gyrase inhibitors. 25 known gyrase inhibitors among the 218 top hits demonstrate that the SDFQ HTS campaign was successful.

Figure 23:
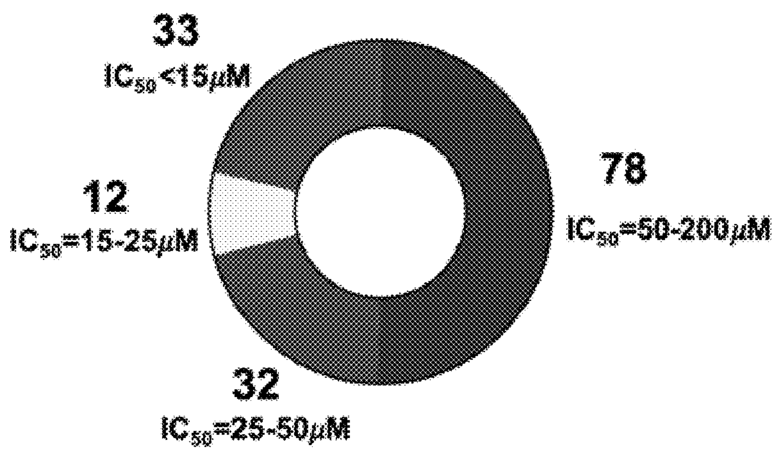
FIG. 23 shows 155 new DNA gyrase inhibitors with an inhibition $IC_{50}$ value against *E. coli* DNA gyrase less than 200 μM. Among the 155 gyrase inhibitors, 33 compounds have $IC_{50}$ values less than 15 μM; 12 compounds have $IC_{50}$ values between 15 and 25 μM; 25 compounds have $IC_{50}$ values between 25 and 50 μM; and 78 compounds have $IC_{50}$ values between 50 and 200 μM.

After the analysis of all 2891 compounds, a total of 208 compounds were obtained from MolPort and NCI DTP program. The selection is based on their chemical structures and the screening results. Most of these compounds have similar activities for both the primary and secondary assays. The identities of these compounds were confirmed using mass spectrometry (data not shown). These compounds were then screened for their *E. coli* gyrase inhibition activities using agarose gel-based DNA gyrase assays (FIGS. 18-22). The results showed that 155 compounds are *E. coli* DNA gyrase inhibitors with the $IC_{50}$ values less than 200 μM (FIG. 23). 102 gyrase inhibitors with $IC_{50}$ values less than 200 μM are shown in Table 1a.

TABLE 1a

| Compounds as *E. coli* DNA gyrase inhibitors. | |
|---|---|
| Compounds # | Structure |
| 4 | 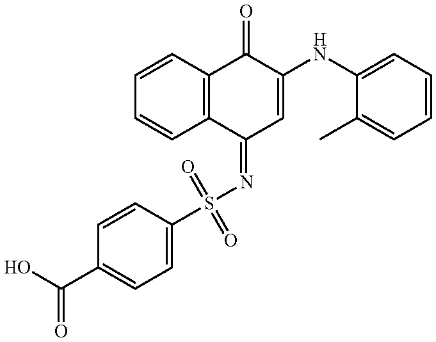 [SMILES: Cc1ccccc1NC1=C/C(=N/S(=O)(=O)c2ccc(C(=O)O)cc2)c2ccccc2C1=O] |
| 7 | 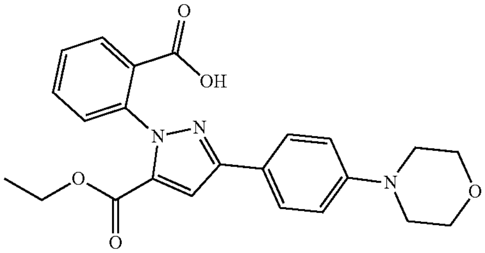 [SMILES: CCOC(=O)c1cc(-c2ccc(N3CCOCC3)cc2)nn1-c1ccccc1C(=O)O] |

TABLE la-continued
| Compounds as *E. coli* DNA gyrase inhibitors. | |
|---|---|
| Compounds # | Structure |
| 9 | 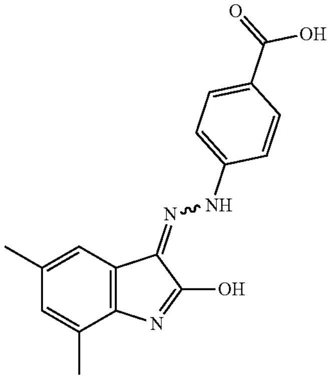 [SMILES: Cc1cc(C)c2c(c1)C(=NNc1ccc(C(=O)O)cc1)C(O)=N2] |
| 10 | 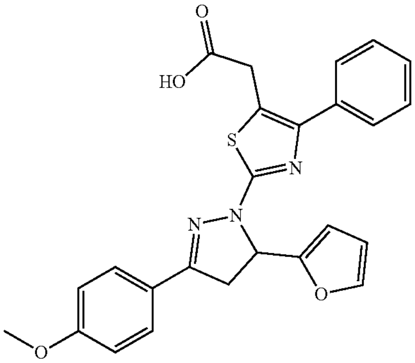 [SMILES: COc1ccc(C2=NN(c3nc(-c4ccccc4)c(CC(=O)O)s3)C(c3ccco3)C2)cc1] |
| 12 | 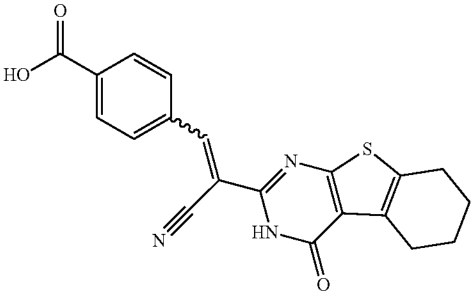 [SMILES: N#CC(=Cc1ccc(C(=O)O)cc1)c1nc2sc3c(c2c(=O)[nH]1)CCCC3] |
| 13 | 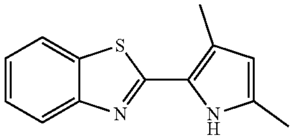 [SMILES: Cc1cc(C)c(-c2nc3ccccc3s2)[nH]1] |
| 15 | 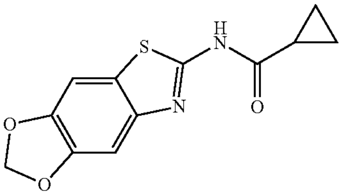 [SMILES: O=C(Nc1nc2cc3c(cc2s1)OCO3)C1CC1] |

TABLE la-continued
| Compounds as *E. coli* DNA gyrase inhibitors. | |
|---|---|
| Compounds # | Structure |
| 17 | 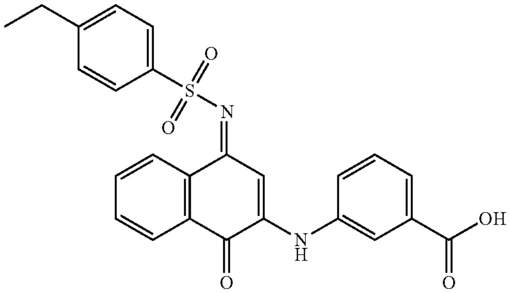 [SMILES: CCc1ccc(S(=O)(=O)/N=C2/C=C(Nc3cccc(C(=O)O)c3)C(=O)c3ccccc32)cc1] |
| 18 | 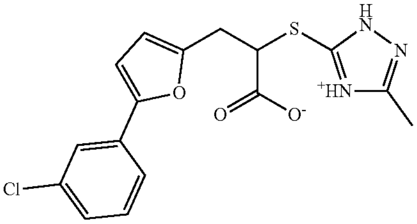 [SMILES: Cc1n[nH]c(SC(Cc2ccc(-c3cccc(Cl)c3)o2)C(=O)[O-])[nH+]1] |
| 19 | 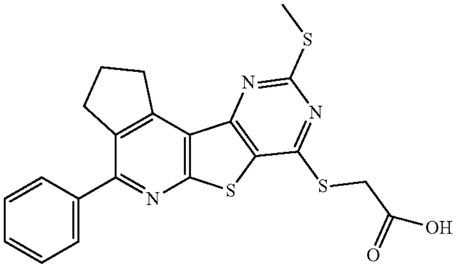 [SMILES: CSc1nc(SCC(=O)O)c2sc3nc(-c4ccccc4)c4c(c3c2n1)CCC4] |
| 21 | 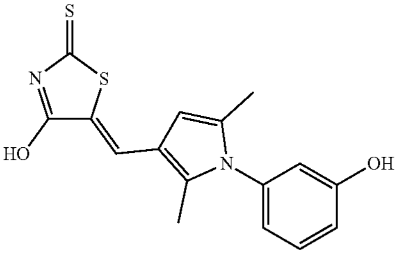 [SMILES: Cc1cc(/C=C2\SC(=S)N=C2O)c(C)n1-c1cccc(O)c1] |
| 22 | 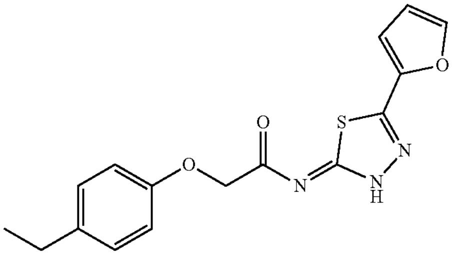 [SMILES: CCc1ccc(OCC(=O)/N=c2/[nH]nc(-c3ccco3)s2)cc1] |

TABLE la-continued
| Compounds as *E. coli* DNA gyrase inhibitors. | |
|---|---|
| Compounds # | Structure |
| 23 | 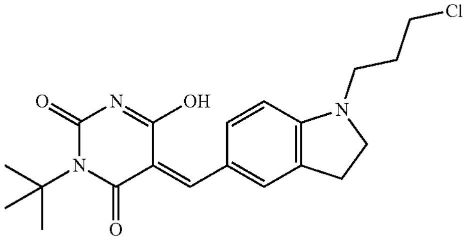 [SMILES: CC(C)(C)N1C(=O)N=C(O)/C(=C\c2ccc3c(c2)CCN3CCCCl)C1=O] |
| 24 | 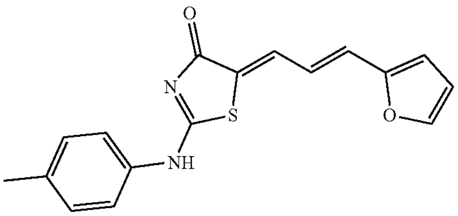 [SMILES: Cc1ccc(NC2=NC(=O)/C(=C/C=C/c3ccco3)S2)cc1] |
| 25 | 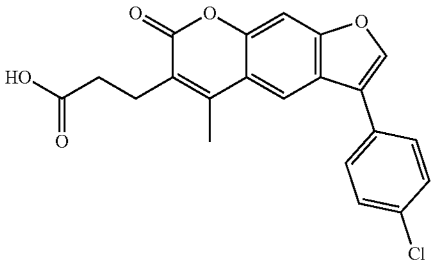 [SMILES: Cc1c(CCC(=O)O)c(=O)oc2cc3occ(-c4ccc(Cl)cc4)c3cc12] |
| 27 | 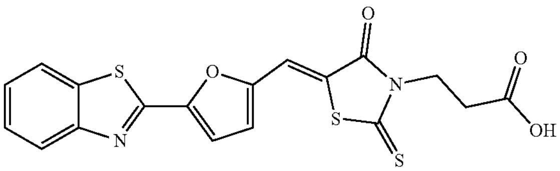 [SMILES: O=C(O)CCN1C(=O)/C(=C/c2ccc(-c3nc4ccccc4s3)o2)SC1=S] |
| 28 | 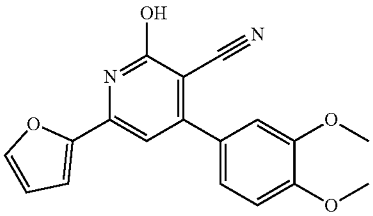 [SMILES: COc1ccc(-c2cc(-c3ccco3)nc(O)c2C#N)cc1OC] |
| 29 | 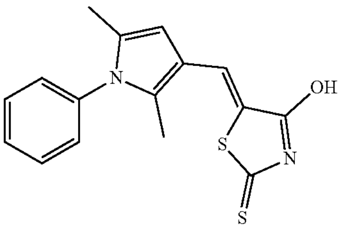 [SMILES: Cc1cc(/C=C2\SC(=S)N=C2O)c(C)n1-c1ccccc1] |

TABLE Ia-continued
| Compounds as *E. coli* DNA gyrase inhibitors. | |
|---|---|
| Compounds # | Structure |
| 30 | 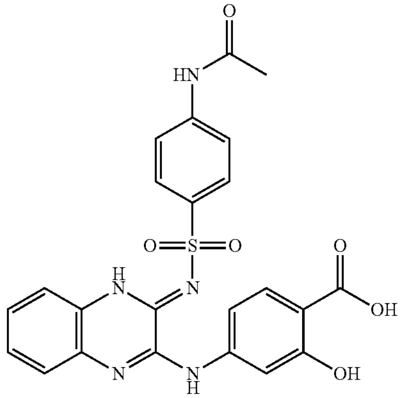 [SMILES: CC(=O)Nc1ccc(S(=O)(=O)/N=c2\[nH]c3ccccc3nc2Nc2ccc(C(=O)O)c(O)c2)cc1] |
| 31 | 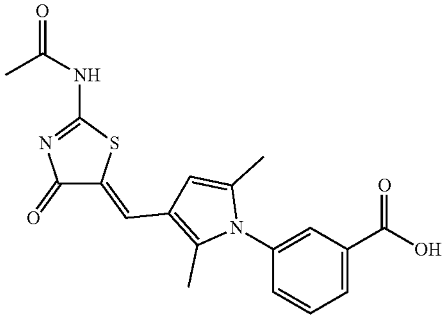 [SMILES: CC(=O)NC1=NC(=O)/C(=C/c2cc(C)n(-c3cccc(C(=O)O)c3)c2C)S1] |
| 33 | 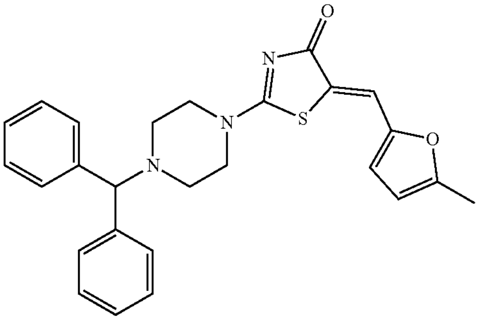 [SMILES: Cc1ccc(/C=C2\SC(N3CCN(C(c4ccccc4)c4ccccc4)CC3)=NC2=O)o1] |
| 35 | 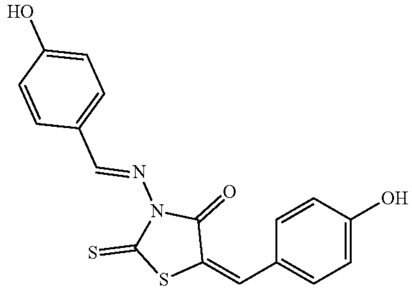 [SMILES: O=C1/C(=C\c2ccc(O)cc2)SC(=S)N1/N=C/c1ccc(O)cc1] |

TABLE la-continued
| Compounds as *E. coli* DNA gyrase inhibitors. | |
|---|---|
| Compounds # | Structure |
| 36 | 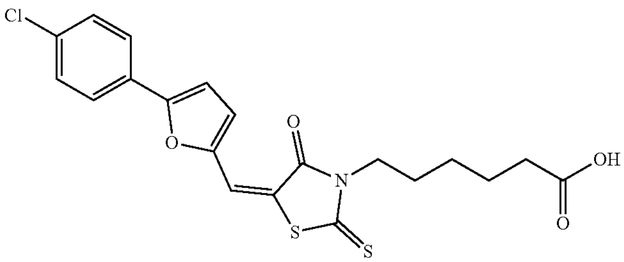 [SMILES: O=C(O)CCCCCN1C(=O)/C(=C\c2ccc(-c3ccc(Cl)cc3)o2)SC1=S] |
| 38 | 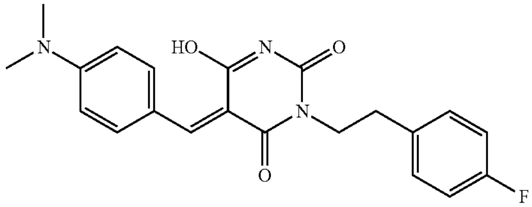 [SMILES: CN(C)c1ccc(/C=C2/C(=O)N(CCc3ccc(F)cc3)C(=O)N=C2O)cc1] |
| 40 | 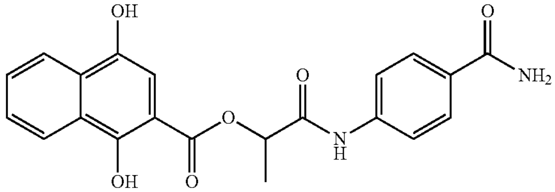 [SMILES: CC(OC(=O)c1cc(O)c2ccccc2c1O)C(=O)Nc1ccc(C(N)=O)cc1] |
| 41 | 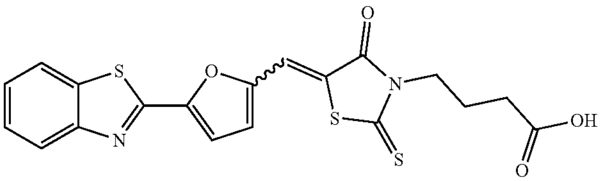 [SMILES: O=C(O)CCCN1C(=O)C(=Cc2ccc(-c3nc4ccccc4s3)o2)SC1=S] |
| 42 | 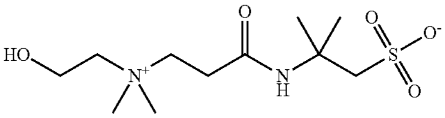 [SMILES: CC(C)(CS(=O)(=O)[O-])NC(=O)CC[N+](C)(C)CCO] |
| 44 | 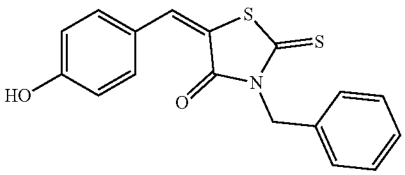 [SMILES: O=C1/C(=C\c2ccc(O)cc2)SC(=S)N1Cc1ccccc1] |

TABLE la-continued
| Compounds as *E. coli* DNA gyrase inhibitors. | |
|---|---|
| Compounds # | Structure |
| 45 | 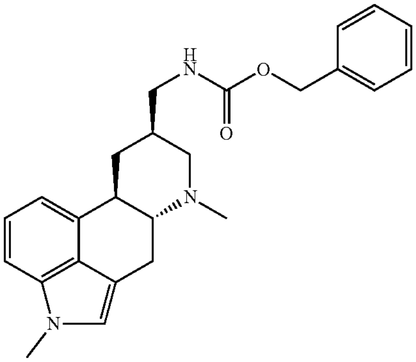 [SMILES: CN1C[C@H](CNC(=O)OCc2ccccc2)C[C@@H]2c3cccc4c3c(cn4C)C[C@H]21] |
| 46 | 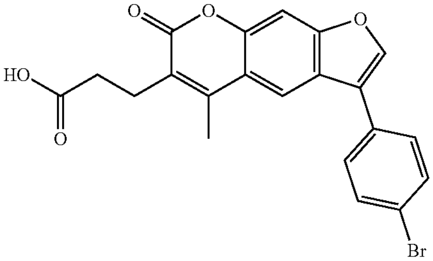 |
| 47 | 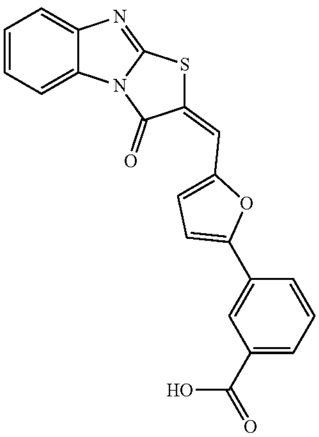 [SMILES: O=C(O)c1cccc(-c2ccc(/C=c3/sc4nc5ccccc5n4c3=O)o2)c1] |
| 48 | 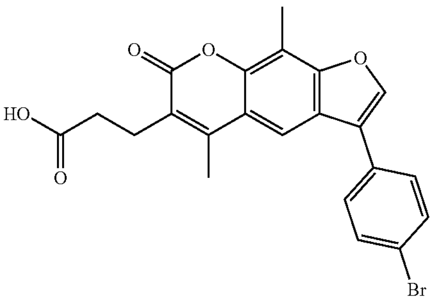 [SMILES: Cc1c(CCC(=O)O)c(=O)oc2c(C)c3occ(-c4ccc(Br)cc4)c3cc12] |

TABLE la-continued
| Compounds as *E. coli* DNA gyrase inhibitors. | |
|---|---|
| Compounds # | Structure |
| 49 | 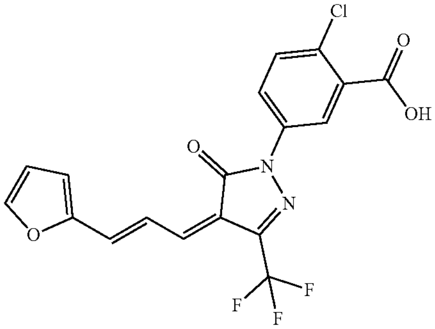 [SMILES: O=C(O)c1cc(N2N=C(C(F)(F)F)/C(=C/C=C/c3ccco3)C2=O)ccc1Cl] |
| 51 | 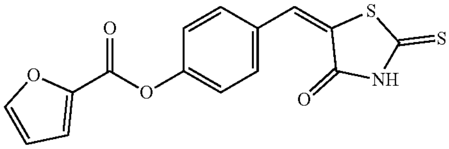 [SMILES: O=C1NC(=S)S/C1=C/c1ccc(OC(=O)c2ccco2)cc1] |
| 53 | 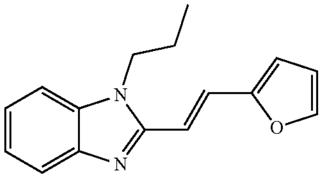 [SMILES: CCCn1c(/C=C/c2ccco2)nc2ccccc21] |
| 54 | 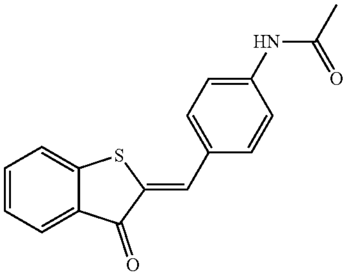 [SMILES: CC(=O)Nc1ccc(/C=C2\Sc3ccccc3C2=O)cc1] |
| 55 | 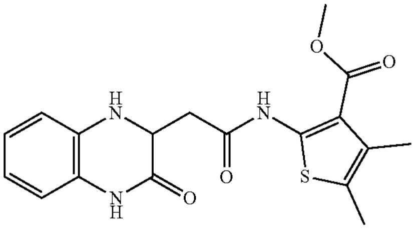 [SMILES: COC(=O)c1c(NC(=O)CC2Nc3ccccc3NC2=O)sc(C)c1C] |
| 56 | 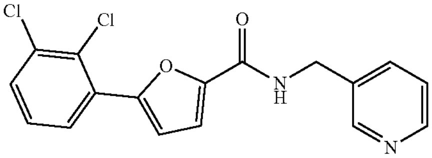 [SMILES: O=C(NCc1cccnc1)c1ccc(-c2cccc(Cl)c2Cl)o1] |

TABLE Ia-continued
| Compounds # | Structure |
|---|---|
| | Compounds as *E. coli* DNA gyrase inhibitors. |
| 57 | 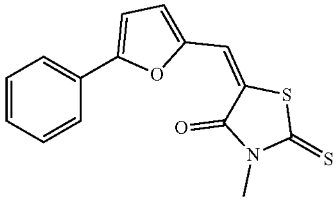 [SMILES: CN1C(=O)/C(=C\c2ccc(-c3ccccc3)o2)SC1=S] |
| 58 | 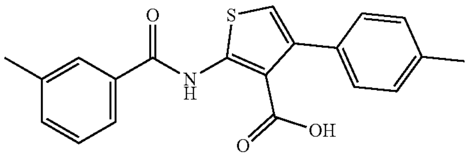 |
| 60 | 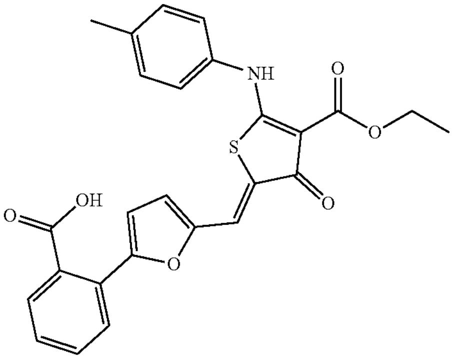 [SMILES: CCOC(=O)C1=C(Nc2ccc(C)cc2)S/C(=C\c2ccc(-c3ccccc3C(=O)O)o2)C1=O] |
| 61 | 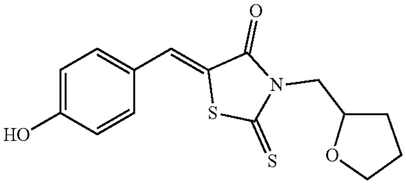 [SMILES: O=C1/C(=C/c2ccc(O)cc2)SC(=S)N1CC1CCCO1] |
| 62 | 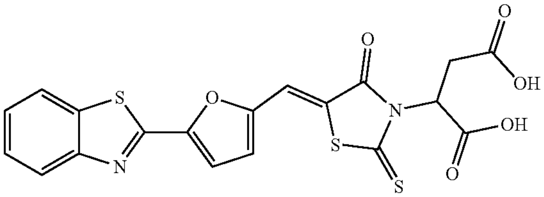 [SMILES: O=C(O)CC(C(=O)O)N1C(=O)/C(=C/c2ccc(-c3nc4ccccc4s3)o2)SC1=S] |

TABLE Ia-continued
| Compounds as *E. coli* DNA gyrase inhibitors. | |
|---|---|
| Compounds # | Structure |
| 63 | 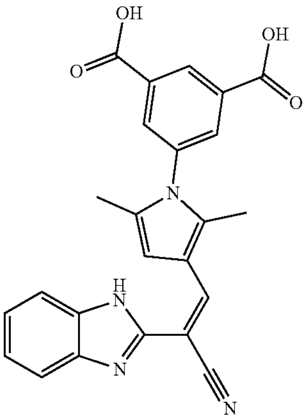 [SMILES: Cc1cc(/C=C(/C#N)c2nc3ccccc3[nH]2)c(C)n1-c1cc(C(=O)O)cc(C(=O)O)c1] |
| 64 | 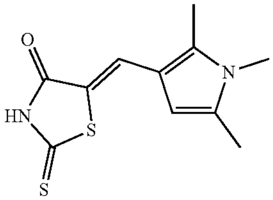 [SMILES: Cc1cc(/C=C2\SC(=S)NC2=O)c(C)n1C] |
| 65 | 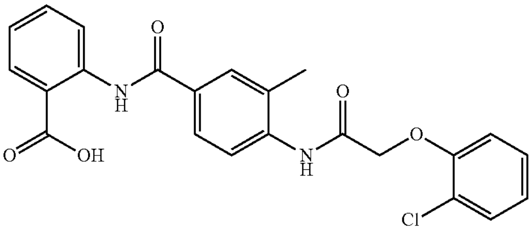 [SMILES: Cc1cc(C(=O)Nc2ccccc2C(=O)O)ccc1NC(=O)COc1ccccc1Cl] |
| 68 | 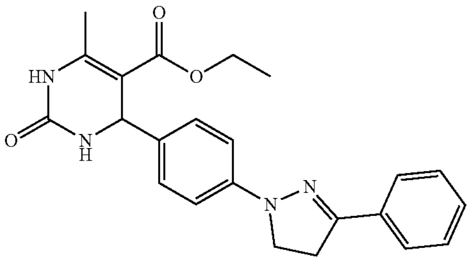 [SMILES: CCOC(=O)C1=C(C)NC(=O)NC1c1ccc(N2CCC(c3ccccc3)=N2)cc1] |
| 70 | 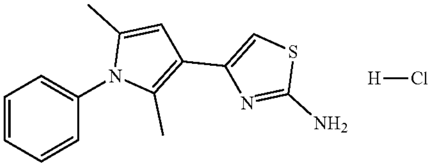 [SMILES: Cc1cc(-c2csc(N)n2)c(C)n1-c1ccccc1 ; Cl] |
| 71 | 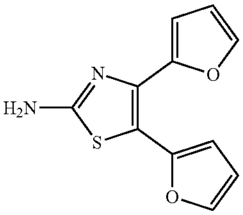 [SMILES: Nc1nc(-c2ccco2)c(-c2ccco2)s1] |

TABLE la-continued
| Compounds as *E. coli* DNA gyrase inhibitors. | |
|---|---|
| Compounds # | Structure |
| 72 | 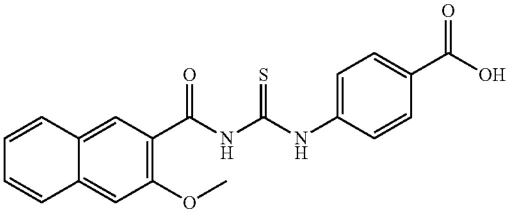 [SMILES: COc1cc2ccccc2cc1C(=O)NC(=S)Nc1ccc(C(=O)O)cc1] |
| 73 | 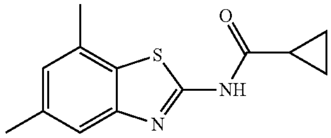 [SMILES: Cc1cc(C)c2sc(NC(=O)C3CC3)nc2c1] |
| 74 | 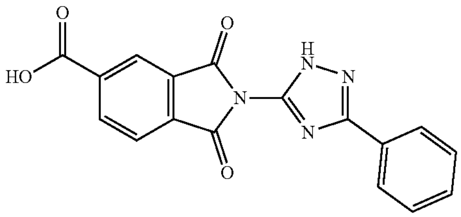 [SMILES: O=C(O)c1ccc2c(c1)C(=O)N(c1nc(-c3ccccc3)n[nH]1)C2=O] |
| 75 | 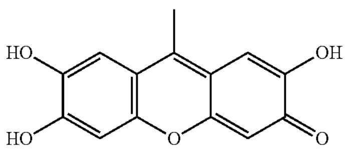 [SMILES: Cc1c2cc(O)c(=O)cc-2oc2cc(O)c(O)cc12] |
| 76 | 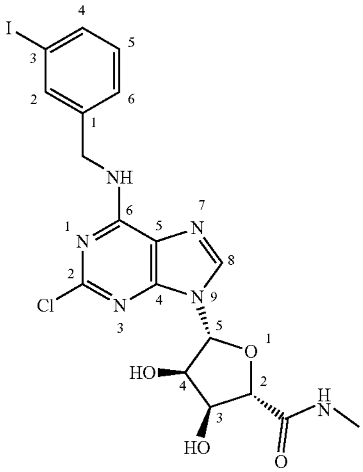 2-Cl-IB-Meca |

TABLE Ia-continued
| Compounds as *E. coli* DNA gyrase inhibitors. | |
|---|---|
| Compounds # | Structure |
| 78 | 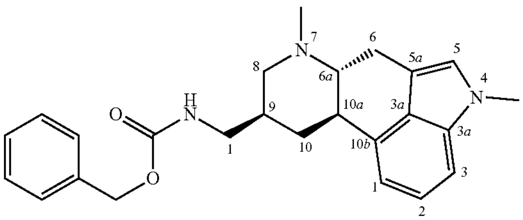 Metergolin |
| 79 | 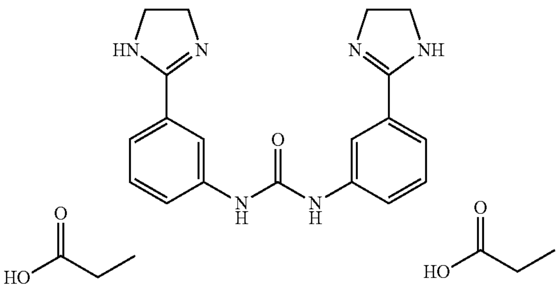 Imidocarb Dipropionate |
| 82 | 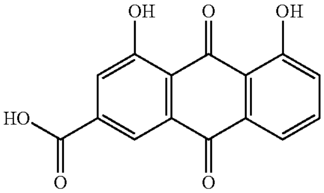 Rhein |
| 83 | 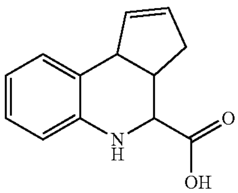 CBR00557 |
| 102 | 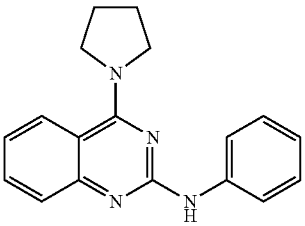 [SMILES: c1ccc(Nc2nc(N3CCCC3)c3ccccc3n2)cc1] |

TABLE Ia-continued
| Compounds as *E. coli* DNA gyrase inhibitors. | |
|---|---|
| Compounds # | Structure |
| 104 | 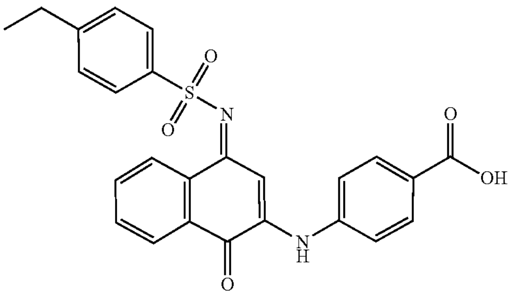 [SMILES: CCc1ccc(S(=O)(=O)/N=C2/C=C(Nc3ccc(C(=O)O)cc3)C(=O)c3ccccc32)cc1] |
| 105 | 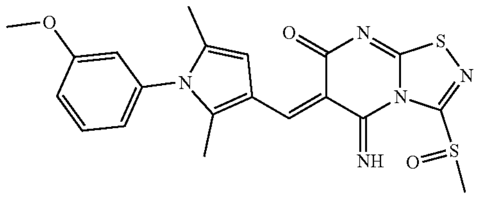 [SMILES: COc1cccc(-n2c(C)cc(/C=C3/C(=N)N4C(=NC3=O)SN=C4S(C)=O)c2C)c1] |
| 106 | 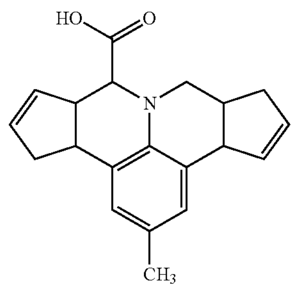 [SMILES: Cc1cc2c3c(c1)C1CC=CC1C(C(=O)O)N3CC1CC=CC21] |
| 108 | 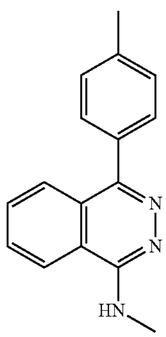 [SMILES: CNc1nnc(-c2ccc(C)cc2)c2ccccc12] |
| 109 | 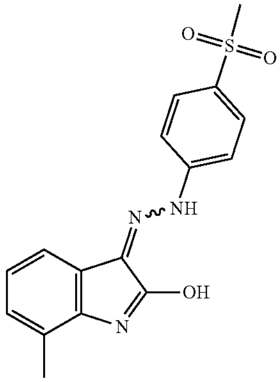 [SMILES: Cc1cccc2c1N=C(O)C2=NNc1ccc(S(C)(=O)=O)cc1] |

TABLE Ia-continued
| Compounds as *E. coli* DNA gyrase inhibitors. | |
|---|---|
| Compounds # | Structure |
| 110 | 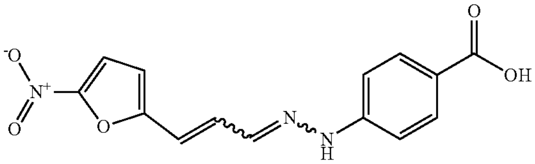 |
| 111 | 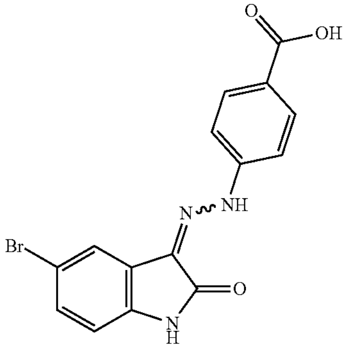 [SMILES: O=C1Nc2ccc(Br)cc2C1=NNc1ccc(C(=O)O)cc1] |
| 112 | 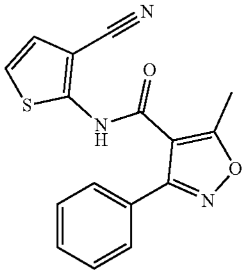 N-(3-cyanothiophen-2-yl)-5-methyl-3-phenyl-1,2-oxazole-4-carboxamide |
| 115 | 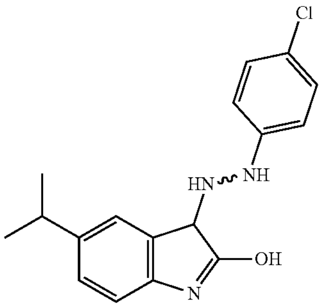 3-[2-(4-chlorophenyl)hydrazin-1-ylidene]-5-(propan-2-yl)-3H-indol-2-ol |
| 122 | 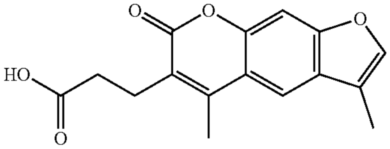 3-[3,5-dimethyl-7-oxo-7H-furo[3,2-g]chromen-6-yl]propanoic acid |

TABLE Ia-continued
| Compounds as *E. coli* DNA gyrase inhibitors. | |
|---|---|
| Compounds # | Structure |
| 129 | 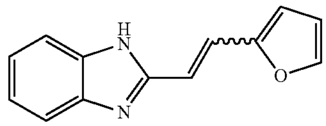<br>2-[2-(furan-2-yl)ethenyl]-1H-1,3-benzodiazole |
| 130 | 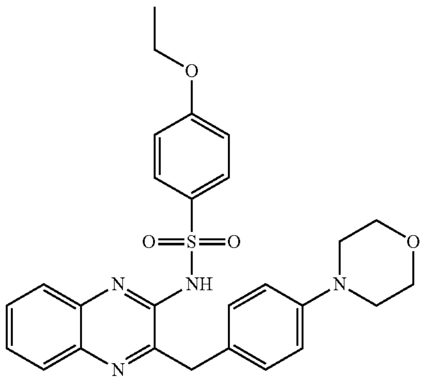<br>4-ethoxy-N-(3-{[4-(morpholin-4-yl)phenyl]amino}quinoxalin-2-yl)benzene-1-sulfonamide |
| 131 | 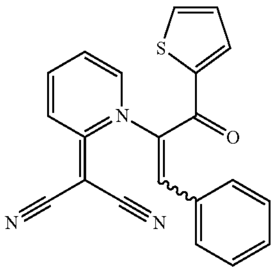<br>1-[3-oxo-1-phenyl-3-(thiophen-2-yl)prop-1-en-2-yl]-1,2,dihydropyridin-2-ylidene)propanedinitrile |
| 132 | 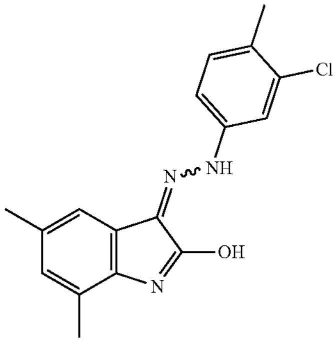<br>3-[2-(3-chloro-4-methylphenyl)hydrazin-1-ylidene]-5,7-dimethyl-3H-indol-2-ol |
| 135 | 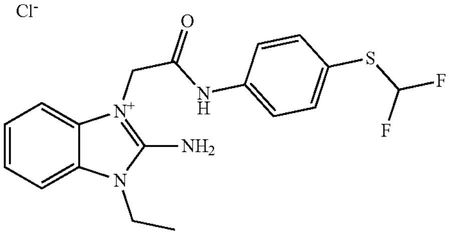 [SMILES: [Cl-] ; CCn1c(N)[n+](CC(=O)Nc2ccc(SC(F)F)cc2)c2ccccc21] |

TABLE la-continued
| Compounds as *E. coli* DNA gyrase inhibitors. | |
|---|---|
| Compounds # | Structure |
| 149 | 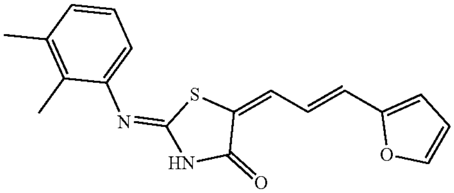 [SMILES: Cc1cccc(/N=C2/NC(=O)/C(=C\C=C\c3ccco3)S2)c1C] |
| 154 | 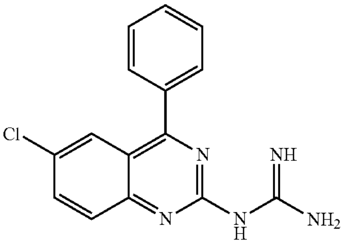 [SMILES: N=C(N)Nc1nc(-c2ccccc2)c2cc(Cl)ccc2n1] |
| 155 | 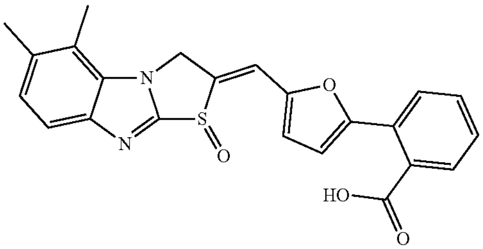 [SMILES: Cc1ccc2nc3n(c2c1C)C/C(=C/c1ccc(-c2ccccc2C(=O)O)o1)S3=O] |
| 157 | 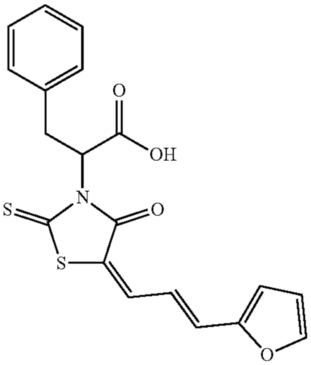 [SMILES: O=C(O)C(Cc1ccccc1)N1C(=O)/C(=C\C=C\c2ccco2)SC1=S] |
| 159 | 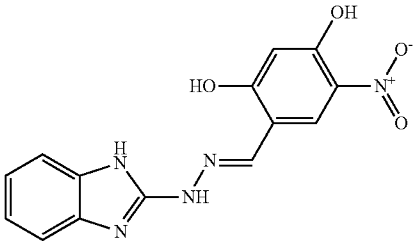 [SMILES: O=[N+]([O-])c1cc(/C=N/Nc2nc3ccccc3[nH]2)c(O)cc1O] |

TABLE la-continued
Compounds as *E. coli* DNA gyrase inhibitors.
| Compounds # | Structure |
|---|---|
| 161 | 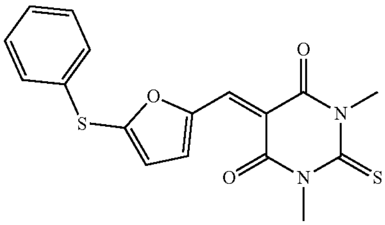 [SMILES: CN1C(=O)C(=Cc2ccc(Sc3ccccc3)o2)C(=O)N(C)C1=S] |
| 163 | 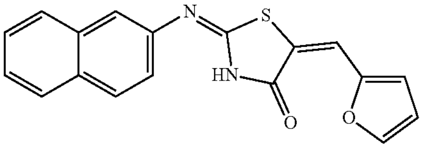 [SMILES: O=C1N/C(=N\c2ccc3ccccc3c2)S/C1=C/c1ccco1] |
| 165 | 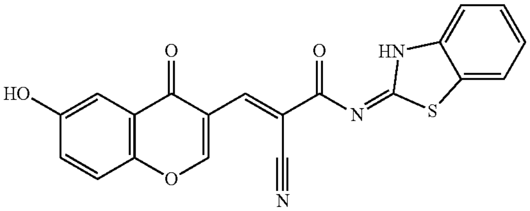 [SMILES: N#C/C(=C\c1coc2ccc(O)cc2c1=O)C(=O)/N=c1\[nH]c2ccccc2s1] |
| 167 | 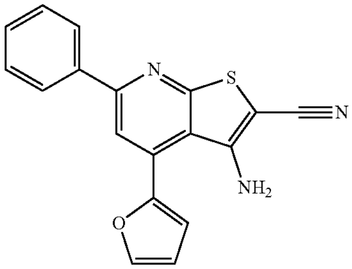 [SMILES: N#Cc1sc2nc(-c3ccccc3)cc(-c3ccco3)c2c1N] |
| 168 | 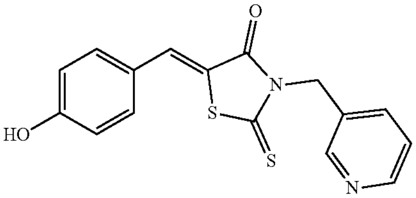 [SMILES: O=C1/C(=C/c2ccc(O)cc2)SC(=S)N1Cc1cccnc1] |
| 169 | 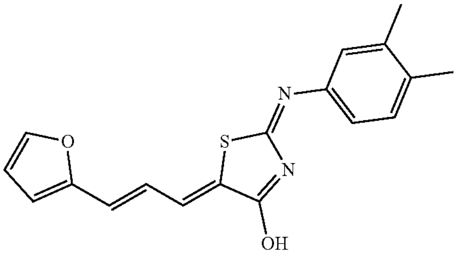 [SMILES: Cc1ccc(/N=C2N=C(O)/C(=C/C=C/c3ccco3)S\2)cc1C] |

TABLE Ia-continued
| Compounds as *E. coli* DNA gyrase inhibitors. | |
|---|---|
| Compounds # | Structure |
| 171 | 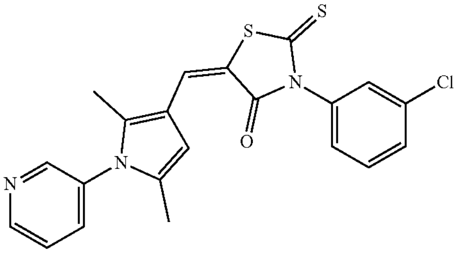 [SMILES: Cc1cc(/C=C2/SC(=S)N(c3cccc(Cl)c3)C2=O)c(C)n1-c1cccnc1] |
| 173 | 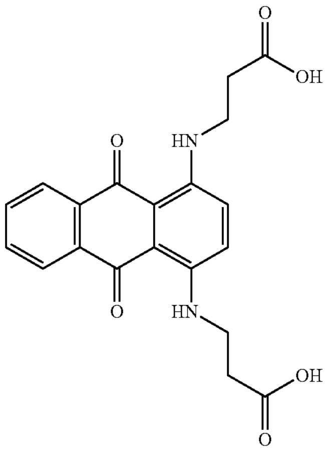 [SMILES: O=C(O)CCNc1ccc(NCCC(=O)O)c2c1C(=O)c1ccccc1C2=O] |
| 176 | 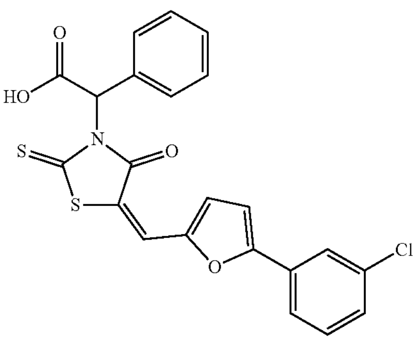 [SMILES: O=C(O)C(c1ccccc1)N1C(=O)/C(=C\c2ccc(-c3cccc(Cl)c3)o2)SC1=S] |
| 178 | 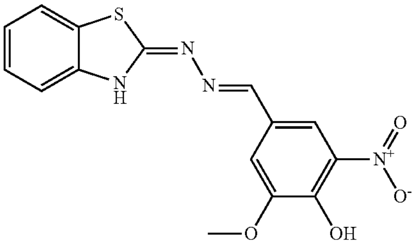 [SMILES: COc1cc(/C=N/N=c2\[nH]c3ccccc3s2)cc([N+](=O)[O-])c1O] |
| 180 | 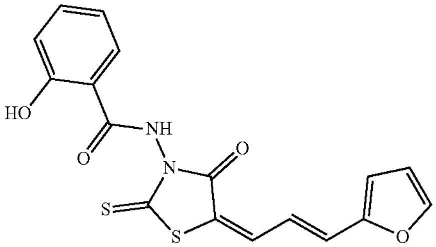 [SMILES: O=C(NN1C(=O)/C(=C\C=C\c2ccco2)SC1=S)c1ccccc1O] |

TABLE Ia-continued
| Compounds as *E. coli* DNA gyrase inhibitors. | |
|---|---|
| Compounds # | Structure |
| 184 | 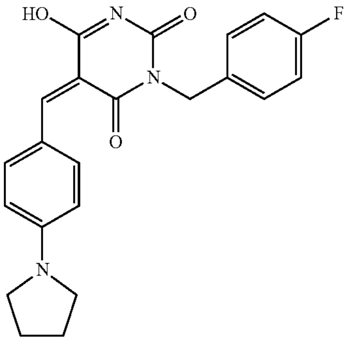 [SMILES: O=C1N=C(O)/C(=C/c2ccc(N3CCCC3)cc2)C(=O)N1Cc1ccc(F)cc1] |
| 188 | 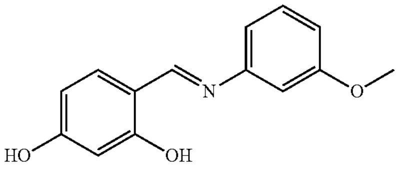 [SMILES: COc1cccc(/N=C/c2ccc(O)cc2O)c1] |
| 189 | 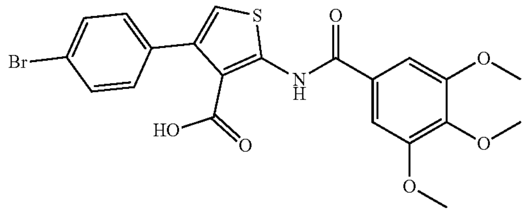 [SMILES: COc1cc(C(=O)Nc2scc(-c3ccc(Br)cc3)c2C(=O)O)cc(OC)c1OC] |
| 192 | 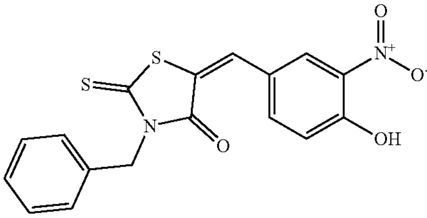 [SMILES: O=C1/C(=C\c2ccc(O)c([N+](=O)[O-])c2)SC(=S)N1Cc1ccccc1] |
| 204 | 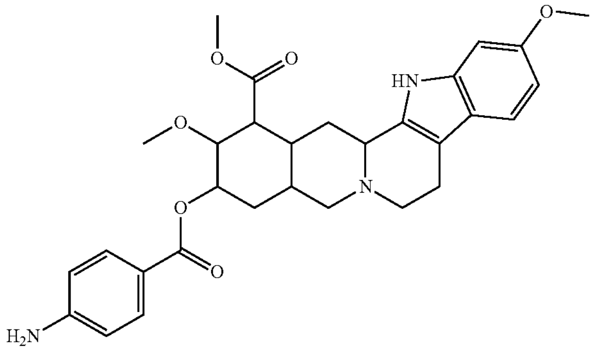 [SMILES: COC(=O)C1C2CC3c4[nH]c5cc(OC)ccc5c4CCN3CC2CC(OC(=O)c2ccc(N)cc2)C1OC]<br>MSC29858 |

TABLE la-continued
| Compounds as *E. coli* DNA gyrase inhibitors. | |
|---|---|
| Compounds # | Structure |
| 205 | 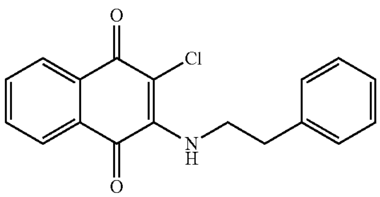 [SMILES: O=C1C(Cl)=C(NCCc2ccccc2)C(=O)c2ccccc21] 2-Chloro-3-(phenethylamino)naphthalene-1,4-dione NSC41098 |
| 206 | 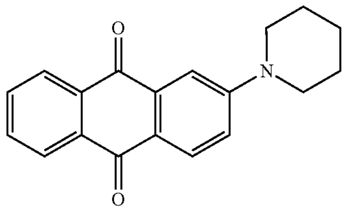 [SMILES: O=C1c2ccccc2C(=O)c2cc(N3CCCCC3)ccc21] 2-Piperidinoanthraquinone NSC43585 |
| 207 | 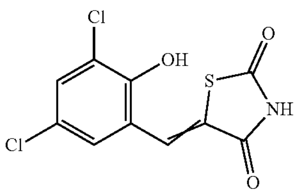 [SMILES: O=C1NC(=O)C(=Cc2cc(Cl)cc(Cl)c2O)S1] 5-(3,5-Dichloro-2-hydroxybenzylidene)-2-thioxo-1,3-thiazolan-4-one NSC44156 |
| 211 | 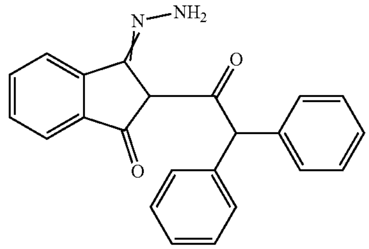 2-Diphenylacetyl-1.3-indandione-1-hydrazone NSC83445 |
| 212 | 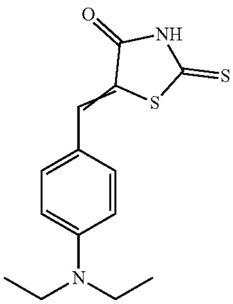 [SMILES: CCN(CC)c1ccc(C=C2SC(=S)NC2=O)cc1] 2-Phenyl-1-(pyridin-2-yl)ethanone NSC111851 |

TABLE Ia-continued
| Compounds as *E. coli* DNA gyrase inhibitors. | |
|---|---|
| Compounds # | Structure |
| 213 | 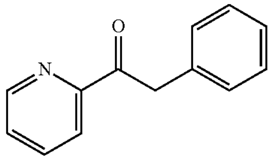 2-Phenyl-1-(pyridin-2-yl)ethanone NSC111851 |
| 215 | 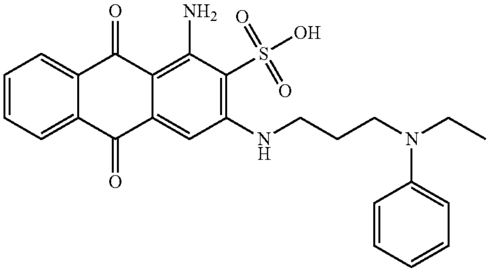 [SMILES: CCN(CCCNc1cc2c(c(N)c1S(=O)(=O)O)C(=O)c1ccccc1C2=O)c1ccccc1] |
| 222 | 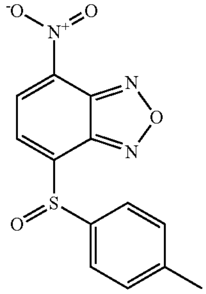 |
| 225 | 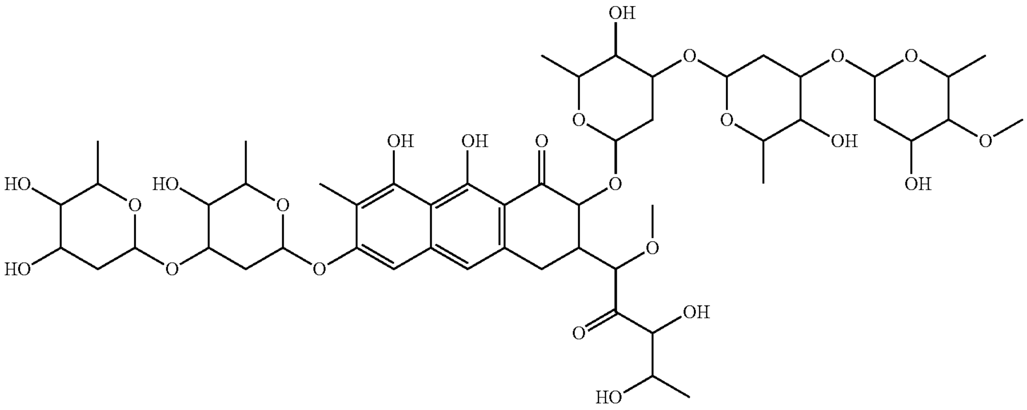 [SMILES: COC(C(=O)C(O)C(C)O)C1Cc2cc3cc(OC4CC(OC5CC(O)C(O)C(C)O5)C(O)C(C)O4)c(C)c(O)c3c(O)c2C(=O)C1OC1CC(OC2CC(OC3CC(O)C(OC)C(C)O3)C(O)C(C)O2)C(O)C(C)O1] |
| 227 | 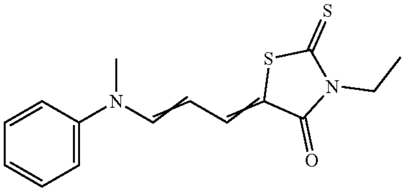 [SMILES: CCN1C(=O)C(=CC=CN(C)c2ccccc2)SC1=S] |

TABLE la-continued
| Compounds as *E. coli* DNA gyrase inhibitors. | |
|---|---|
| Compounds # | Structure |
| 228 | 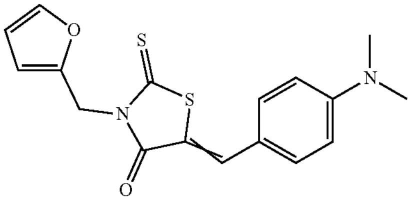 (5Z)-5-[4-(Dimethylamino)benzylidene]-3-(furan-2-ylmethyl)-2-thioxo-1,3-thiazolidin-4-one NSC320207 |
| 229 | 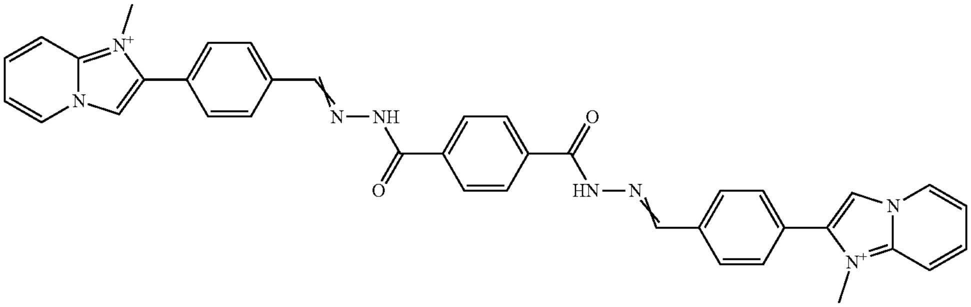 [SMILES: C[n+]1c(-c2ccc(C=NNC(=O)c3ccc(C(=O)NN=Cc4ccc(-c5cn6ccccc6[n+]5C)cc4)cc3)cc2)cn2ccccc21] |
| 232 | 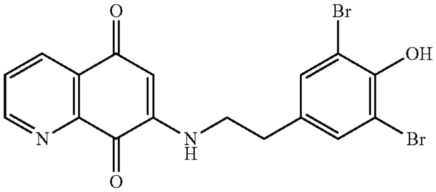 [SMILES: O=C1C=C(NCCc2cc(Br)c(O)c(Br)c2)C(=O)c2ncccc21] |
| 234 | 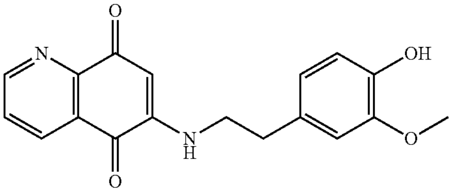 [SMILES: COc1cc(CCNC2=CC(=O)c3ncccc3C2=O)ccc1O] |
| 235 | 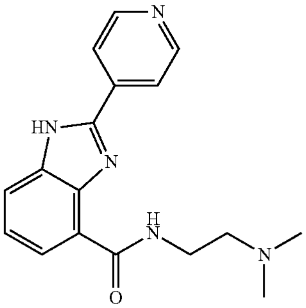 |

TABLE Ia-continued

| Compounds as *E. coli* DNA gyrase inhibitors. | |
|---|---|
| Compounds # | Structure |
| 242 | 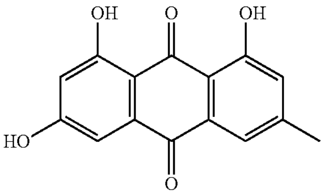 Emodin |
| 253 | 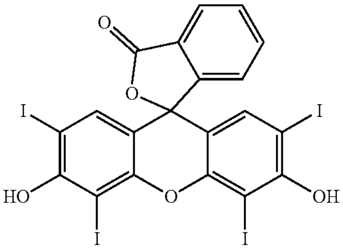 Erythrosin B |
| 256 | 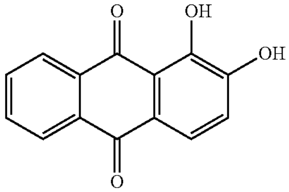 Alizarin |

Among these 102 new gyrase inhibitors, 54 have an inhibition $IC_{50}$ against *E. coli* DNA gyrase less than 50 μM; 33 have an inhibition $IC_{50}$ less than 25 μM; and 22 have an inhibition $IC_{50}$ less than 10 μM (Table 2).

TABLE 2

Compounds as gyrase inhibitors.

| IC50 (50-200 μM) | | | | IC50 (25-50 μM) | | IC50 (15-25 μM) | | IC50 (≤15 μM) | | |
|---|---|---|---|---|---|---|---|---|---|---|
| Cpd # | Set | Cpd # | Set | Cpd # | Set | Cpd # | Set | Cpd # | IC50 | Set |
| 10 | 1 | 68 | 1 | 4 | 1 | 108 | 2 | 9 | 1.69 | 1 |
| 13 | 1 | 70 | 1 | 7 | 1 | 135 | 2 | 19 | 3.55 | 1 |
| 15 | 1 | 74 | 1 | 12 | 1 | 149 | 2 | 25 | 10.62 | 1 |
| 17 | 1 | 79 | 1 | 18 | 1 | 155 | 2 | 27 | 1.74 | 1 |
| 22 | 1 | 82 | 1 | 21 | 1 | 161 | 2 | 36 | 7.421 | 1 |
| 28 | 1 | 83 | 1 | 23 | 1 | 163 | 2 | 41 | 1.48 | 1 |
| 31 | 1 | 106 | 2 | 24 | 1 | 169 | 2 | 42 | 2.18 | 1 |
| 33 | 1 | 110 | 2 | 29 | 1 | 171 | 2 | 46 | 11.23 | 1 |
| 38 | 1 | 112 | 2 | 35 | 1 | 173 | 2 | 47 | 1.87 | 1 |
| 40 | 1 | 129 | 2 | 49 | 1 | 180 | 2 | 48 | 4.28 | 1 |
| 44 | 1 | 130 | 2 | 102 | 2 | 184 | 2 | 72 | 12.4 | 1 |
| 45 | 1 | 131 | 2 | 104 | 2 | | | 73 | 7.86 | 1 |
| 51 | 1 | 167 | 2 | 105 | 2 | | | 75 | 5.28 | 1 |
| 53 | 1 | 168 | 2 | 189 | 2 | | | 76 | 2.53 | 1 |
| 54 | 1 | 204 | NSC29858 | 212 | NSC97270 | | | 154 | 3.125 | 2 |
| 55 | 1 | 205 | NSC41098 | 215 | NSC128440 | | | 157 | 10 | 2 |
| 56 | 1 | 206 | NSC43585 | 222 | NSC228150 | | | 159 | 6.25 | 2 |
| 58 | 1 | 207 | NSC44156 | 224 | NSC265450 | | | 165 | 6.25 | 2 |
| 60 | 1 | 211 | NSC83445 | 225 | NSC269146 | | | 176 | 2 | 2 |
| 61 | 1 | 213 | NSC111851 | 229 | NSC375161 | | | 178 | 1.56 | 2 |
| 62 | 1 | 227 | NSC302964 | 256 | Alizarin | | | 192 | 8 | 2 |

TABLE 2-continued
| Compounds as gyrase inhibitors. | | | | | | | | | | | |
|---|---|---|---|---|---|---|---|---|---|---|---|
| IC50 (50-200 μM) | | | | IC50 (25-50 μM) | | IC50 (15-25 μM) | | IC50 (≤15 μM) | | |
| Cpd # | Set | Cpd # | Set | Cpd # | Set | Cpd # | Set | Cpd # | IC50 | Set |
| 63 | 1 | 228 | NSC320207 | | | | | 253 | 3.125 | Erythrosin B |
| 64 | 1 | 232 | NSC668394 | | | | | Novobiocin | 1.85 | |
| 65 | 1 | 242 | Emodin | | | | | | | |
Additional compounds as *E. coli* DNA gyrase inhibitors with $IC_{50}$ values less than 200 μM are shown in Table 1b.
TABLE 1b
| Additonal compound as *E. Coli* DNA gyrase inhibitors. | |
|---|---|
| Compound # | Structure |
| 67 | 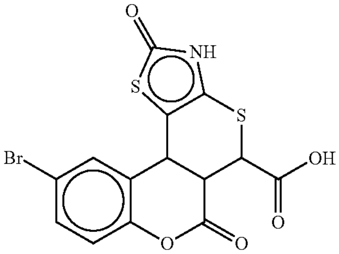 |
| 69 | 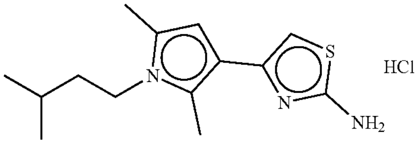 |
| 81 | 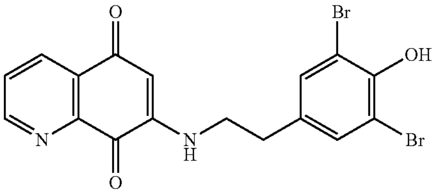 [SMILES: O=C1C=C(NCCc2cc(Br)c(O)c(Br)c2)C(=O)c2ncccc21] |
| 101 | 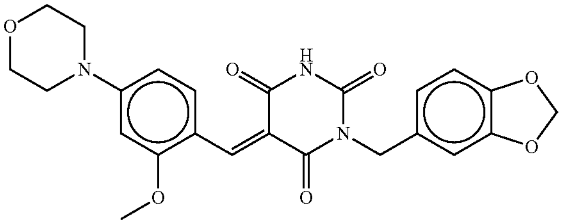 |
| 103 | 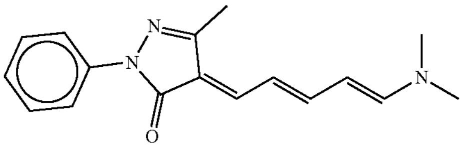 |
| 107 | 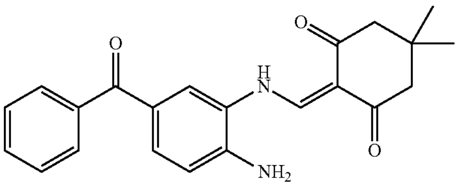 [SMILES: CC1(C)CC(=O)C(=CNc2cc(C(=O)c3ccccc3)ccc2N)C(=O)C1] |

TABLE 1b-continued
| Additonal compound as *E. Coli* DNA gyrase inhibitors. |
|---|
| Compound # Structure |
113
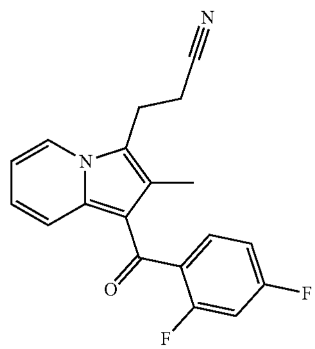 [SMILES: Cc1c(C(=O)c2ccc(F)cc2F)c2ccccn2c1CCC#N]
114
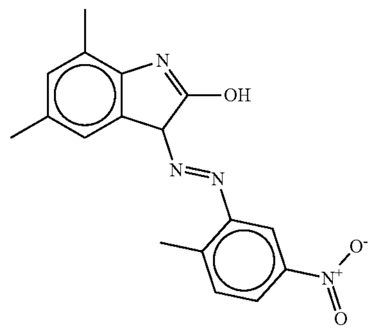
116
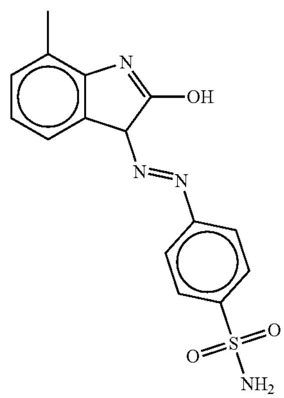
117
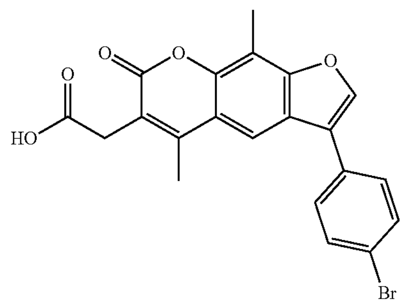 [SMILES: Cc1c(CC(=O)O)c(=O)oc2c(C)c3occ(-c4ccc(Br)cc4)c3cc12]

TABLE 1b-continued
| Additonal compound as *E. Coli* DNA gyrase inhibitors. | |
|---|---|
| Compound # | Structure |
| 119 | 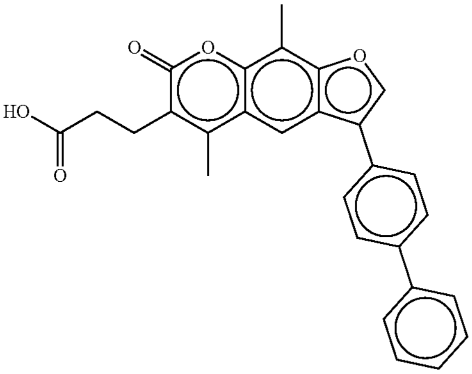 |
| 120 | 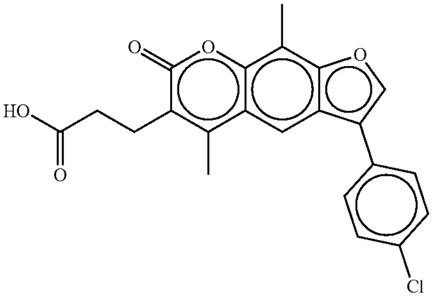 |
| 121 | 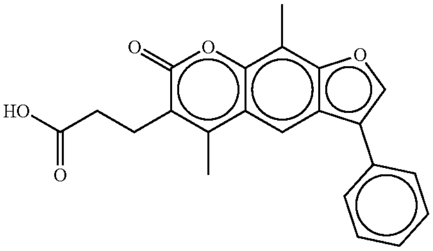 |
| 123 | 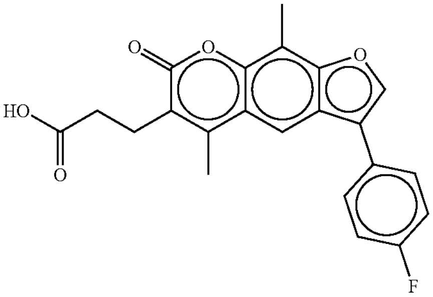 |
| 124 | 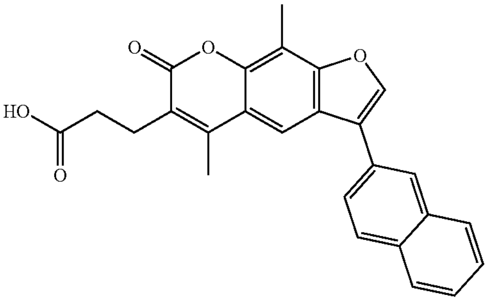 [SMILES: Cc1c(CCC(=O)O)c(=O)oc2c(C)c3occ(-c4ccc5ccccc5c4)c3cc12] |

TABLE 1b-continued
| Additonal compound as *E. Coli* DNA gyrase inhibitors. | |
|---|---|
| Compound # | Structure |
| 125 | 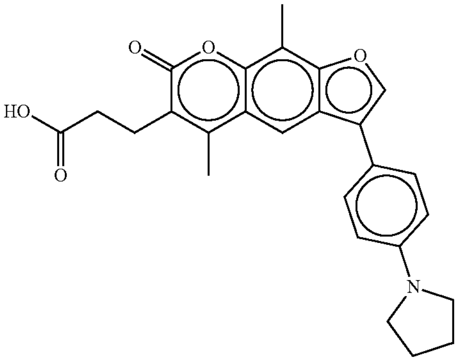 |
| 126 | 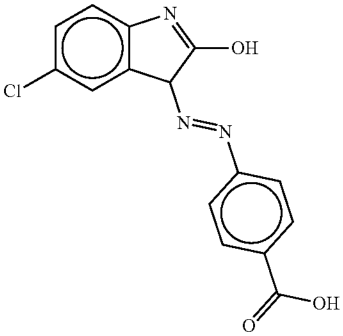 |
| 127 | 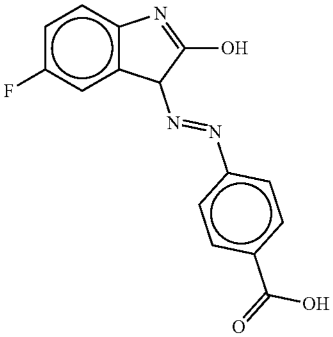 |
| 128 | 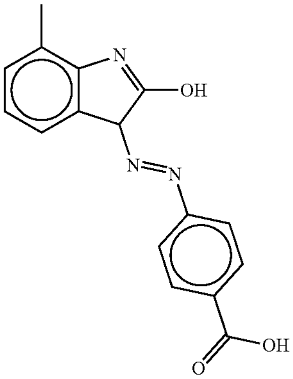 |

TABLE 1b-continued
| Additonal compound as *E. Coli* DNA gyrase inhibitors. |
|---|
| Compound # Structure |
| 133 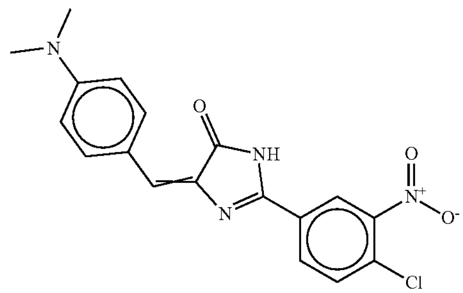 |
| 134 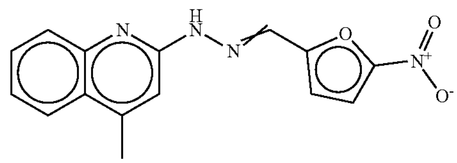 |
| 141 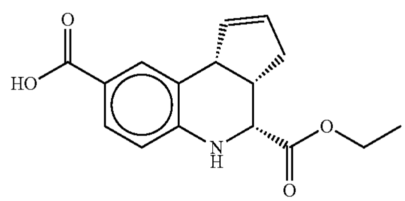 |
| 147 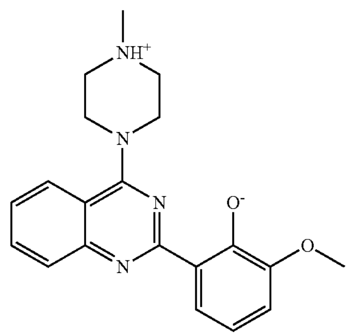 [SMILES: COc1cccc(-c2nc(N3CC[NH+](C)CC3)c3ccccc3n2)c1[O-]] |
| 148 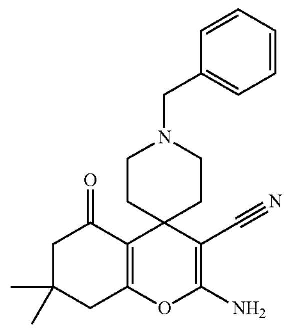 [SMILES: CC1(C)CC(=O)C2=C(C1)OC(N)=C(C#N)C21CCN(Cc2ccccc2)CC1] |

TABLE 1b-continued
| Additonal compound as *E. Coli* DNA gyrase inhibitors. |
|---|
| Compound # Structure |
| 151 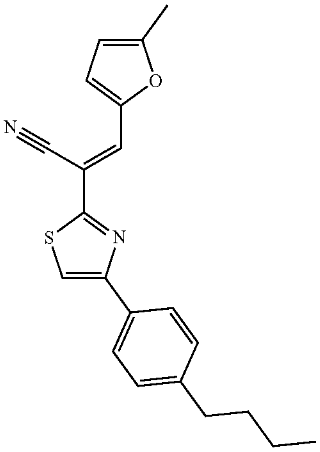 [SMILES: CCCCc1ccc(-c2csc(/C(C#N)=C/c3ccc(C)o3)n2)cc1] |
| 152 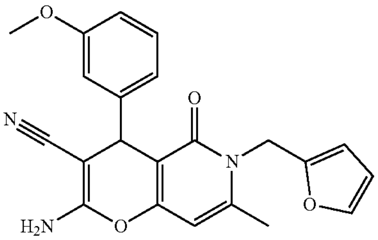 [SMILES: COc1cccc(C2C(C#N)=C(N)Oc3cc(C)n(Cc4ccco4)c(=O)c32)c1] |
| 153 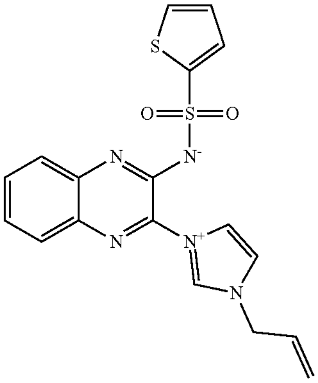 [SMILES: C=CCn1cc[n+](-c2nc3ccccc3nc2[N-]S(=O)(=O)c2cccs2)c1] |
| 156 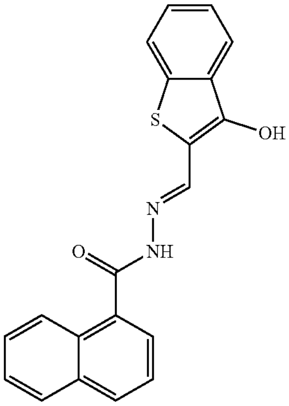 [SMILES: O=C(N/N=C/c1sc2ccccc2c1O)c1cccc2ccccc12] |

TABLE 1b-continued
| Additonal compound as *E. Coli* DNA gyrase inhibitors. | |
|---|---|
| Compound # | Structure |
| 158 | 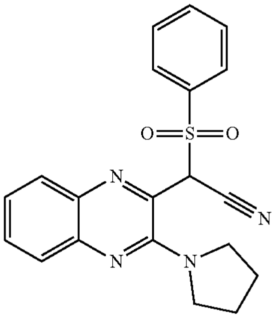 [SMILES: N#CC(c1nc2ccccc2nc1N1CCCC1)S(=O)(=O)c1ccccc1] |
| 160 | 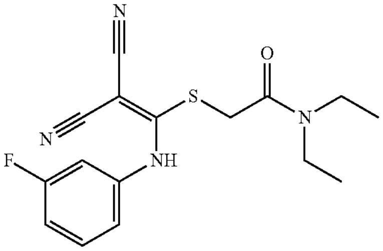 [SMILES: CCN(CC)C(=O)CSC(Nc1cccc(F)c1)=C(C#N)C#N] |
| 162 | 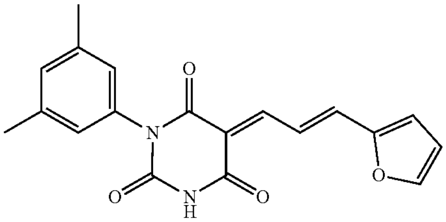 [SMILES: Cc1cc(C)cc(N2C(=O)NC(=O)/C(=C\C=C\c3ccco3)C2=O)c1] |
| 164 | 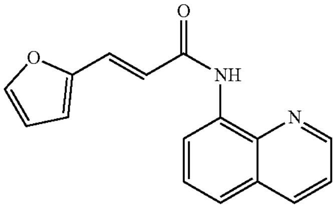 [SMILES: O=C(/C=C/c1ccco1)Nc1cccc2cccnc12] |
| 166 | 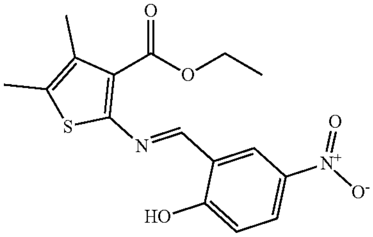 [SMILES: CCOC(=O)c1c(/N=C/c2cc([N+](=O)[O-])ccc2O)sc(C)c1C] |
| 170 | 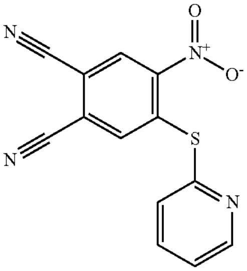 [SMILES: N#Cc1cc(Sc2ccccn2)c([N+](=O)[O-])cc1C#N] |

TABLE 1b-continued
| Additonal compound as *E. Coli* DNA gyrase inhibitors. |
|---|
| Compound # Structure |
172
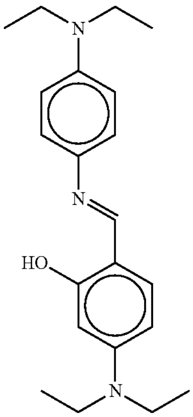
174
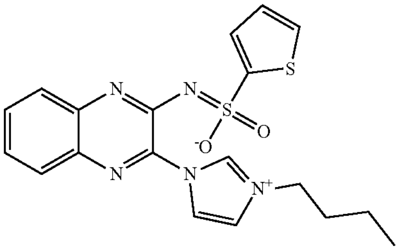
175
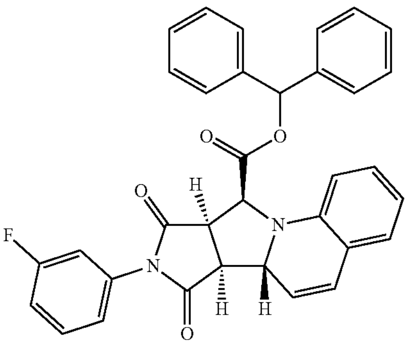 [SMILES: O=C(OC(c1ccccc1)c1ccccc1)[C@@H]1[C@@H]2C(=O)N(c3cccc(F)c3)C(=O)[C@@H]2[C@H]2C=Cc3ccccc3N21]
182
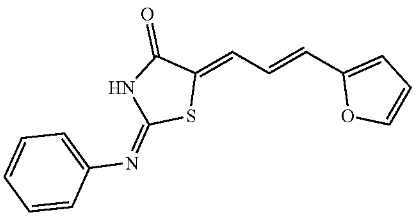 [SMILES: O=C1N/C(=N\c2ccccc2)S/C1=C\C=C\c1ccco1]
183
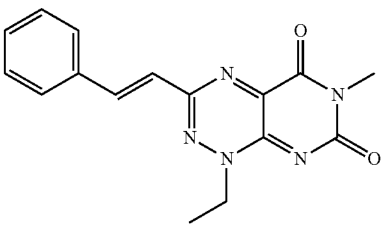 [SMILES: CCn1nc(/C=C/c2ccccc2)nc2c(=O)n(C)c(=O)nc1-2]

TABLE 1b-continued
| Additonal compound as *E. Coli* DNA gyrase inhibitors. | |
|---|---|
| Compound # | Structure |
| 191 | 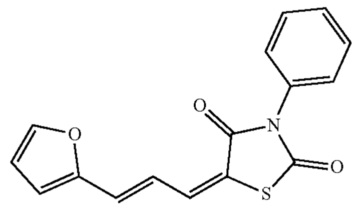 [SMILES: O=C1S/C(=C/C=C/c2ccco2)C(=O)N1c1ccccc1] |
| 217 | 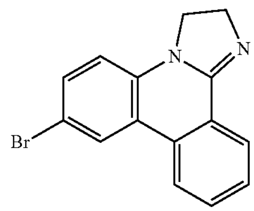 [SMILES: Brc1ccc2c(c1)-c1ccccc1C1=NCCN12] |
| 224 | 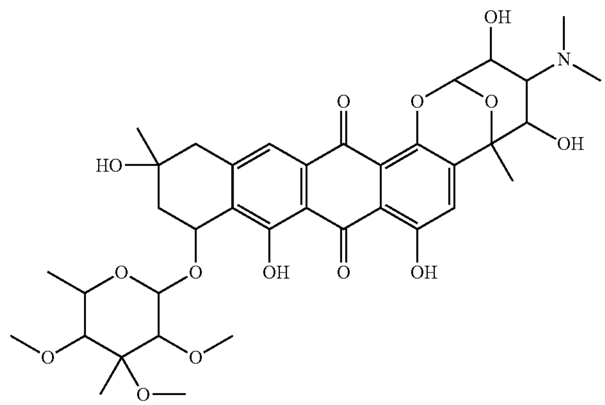 |
| 236 | 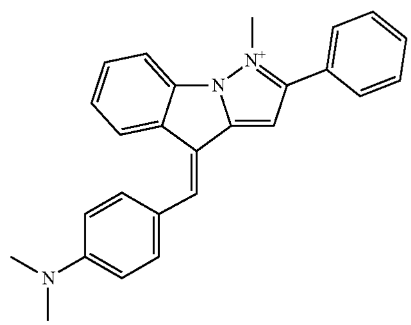 [SMILES: CN(C)c1ccc(/C=c2\c3ccccc3n3c2cc(-c2ccccc2)[n+]3C)cc1] |
| 237 | 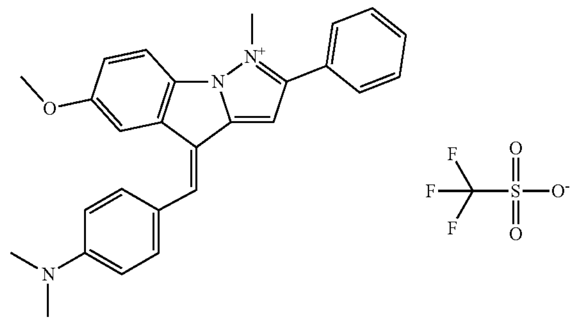 [SMILES: COc1ccc2c(c1)/c(=C\c1ccc(N(C)C)cc1)c1cc(-c3ccccc3)[n+](C)n12 ; O=S(=O)([O-])C(F)(F)F] |

TABLE 1b-continued
| Additonal compound as *E. Coli* DNA gyrase inhibitors. | |
|---|---|
| Compound # | Structure |
| 238 | 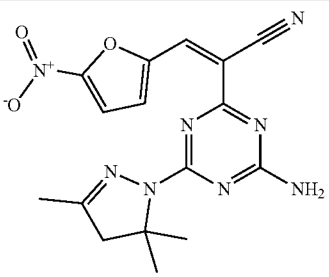 |
| 239 | 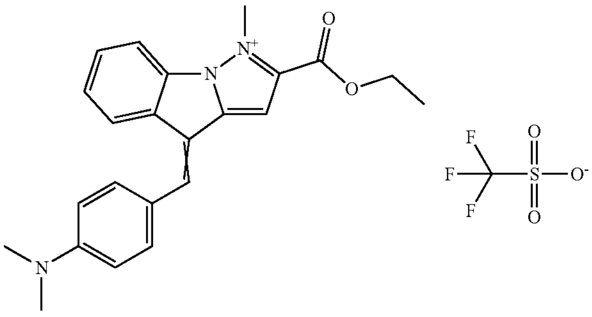 [SMILES: CCOC(=O)c1cc2c(=Cc3ccc(N(C)C)cc3)c3ccccc3n2[n+]1C ; O=S(=O)([O-])C(F)(F)F] |
| 240 | 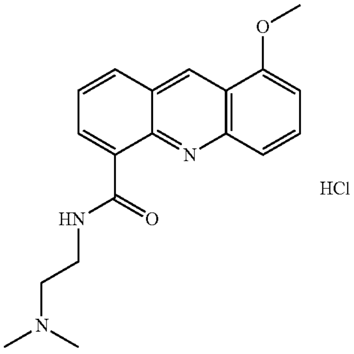 |
| 241 | 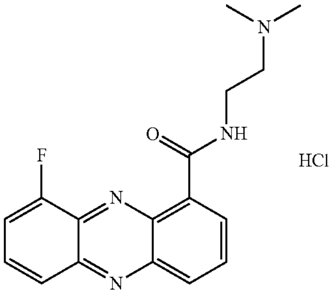 [SMILES: CN(C)CCNC(=O)c1cccc2nc3cccc(F)c3nc12 ; Cl] |
| 243 | 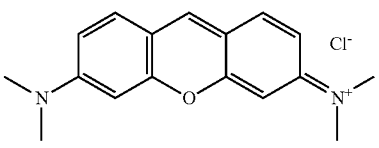 |
| 245 | 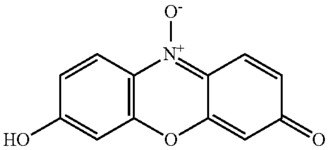 [SMILES: O=c1ccc2[n+]([O-])c3ccc(O)cc3oc-2c1] |

TABLE 1b-continued
Additonal compound as *E. Coli* DNA gyrase inhibitors.
| Compound # | Structure |
|---|---|
| 246 | 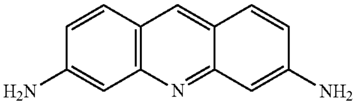 [SMILES: Nc1ccc2cc3ccc(N)cc3nc2c1] |
| 247 | 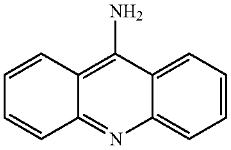 [SMILES: Nc1c2ccccc2nc2ccccc12] |
| 248 | 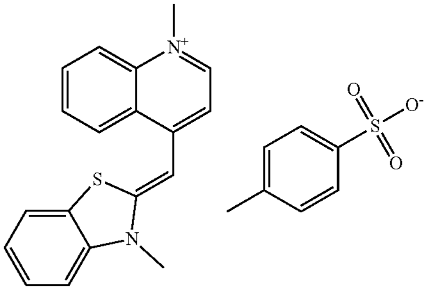 [SMILES: CN1/C(=C/c2cc[n+](C)c3ccccc23)Sc2ccccc21 ; Cc1ccc(S(=O)(=O)[O-])cc1] |
| 249 | 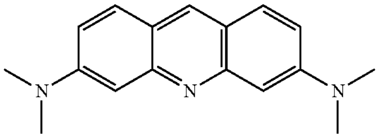 |
| 255 | 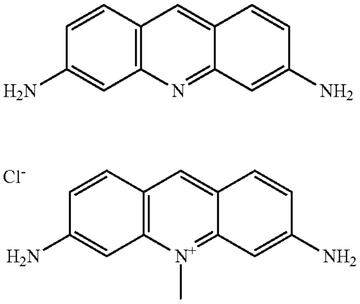 |
| 257 | 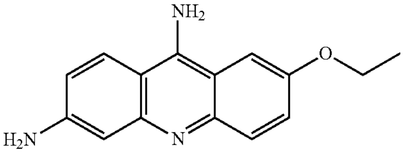 [SMILES: CCOc1ccc2nc3cc(N)ccc3c(N)c2c1] |

TABLE 1b-continued

| Additonal compound as *E. Coli* DNA gyrase inhibitors. | |
|---|---|
| Compound # | Structure |
| 258 | 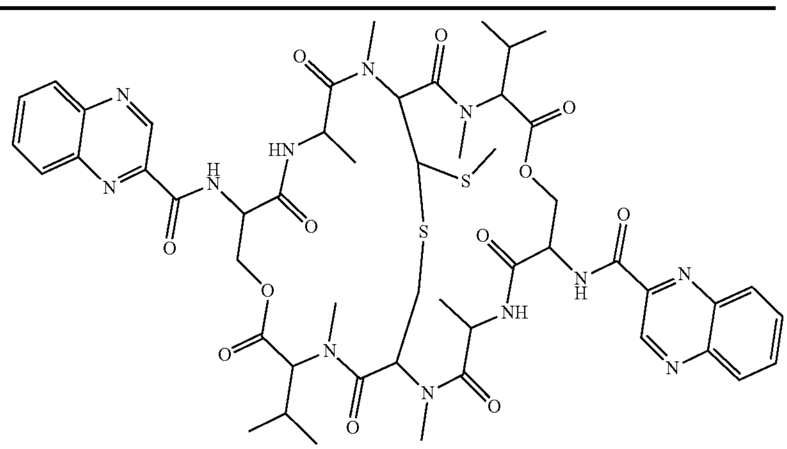 |

Figures 24A, 24B, 24C, 24D, 24E, 24F, 24G, 24H, 24I, 24J, 24K, 24L:
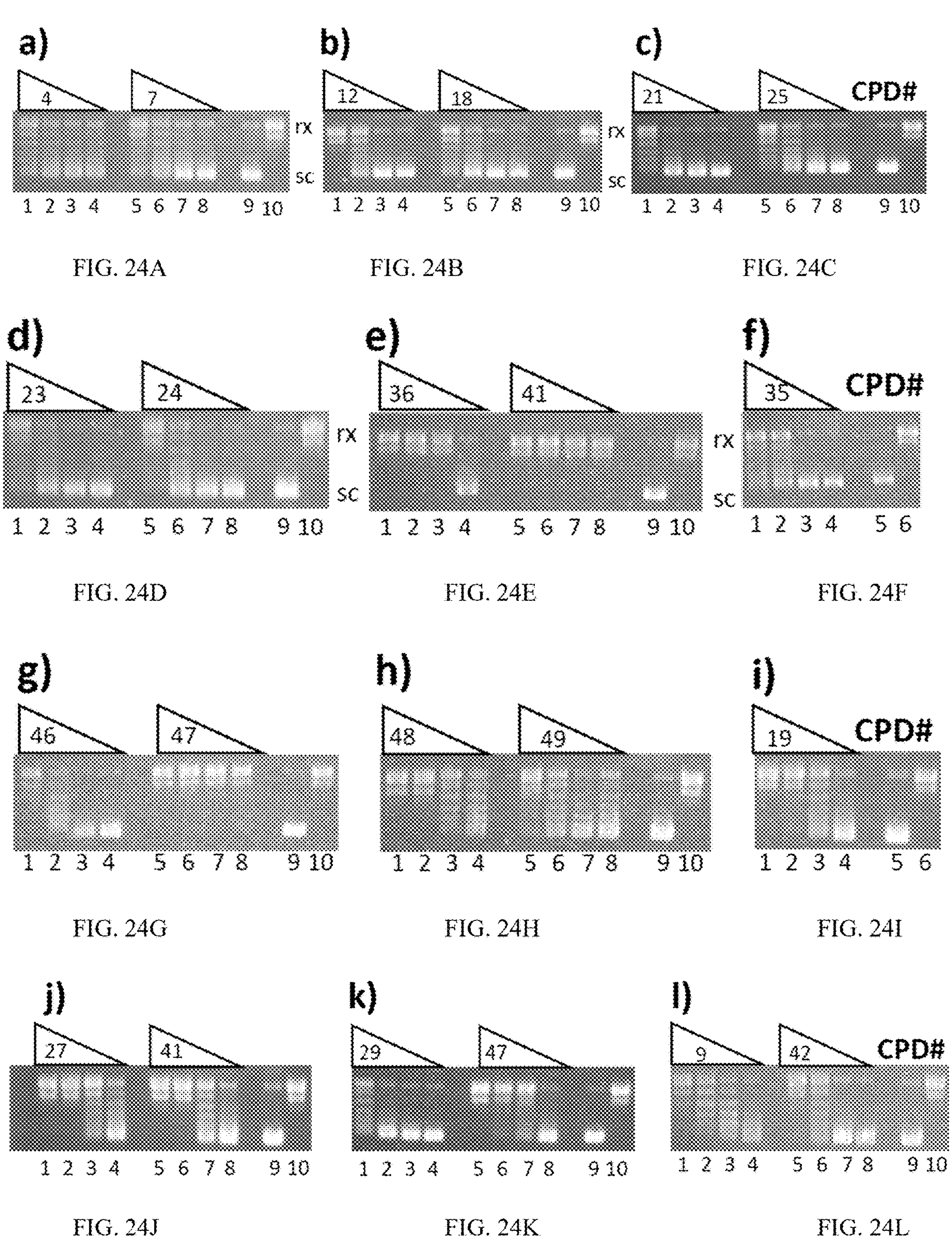
FIGS. 24A-24L show agarose gel-based gyrase inhibition assays to determine the inhibition $IC_{50}$ of MolPort compounds against *E. coli* DNA gyrase. Agarose gel-based gyrase inhibition assays were described in Methods. Compound # are placed above the gels. (A) to (H). Lanes 1-4 or 5-8 correspond, respectively, to 50, 25, 12.5, and 6.25 μM of the compounds used in the assays. (I) to (L). Lanes 1-4 or 5-8 correspond, respectively, to 12.5, 6.25, 3.13, and 1.56 μM of the compounds used in the assays. All compounds' $IC_{50}$ values are less than 50 μM. (A)-(E), (G), (H), and (J)-(L) Lanes 9 and 10 are sc and rx pAB1, respectively. (F) and (I) Lanes 5 and 6 are sc and rx pAB1, respectively.
Figures 25A, 25B, 25C, 25D, 25E, 25F, 25G, 25H, 25I, 25J, 25K, 25L, 25M:
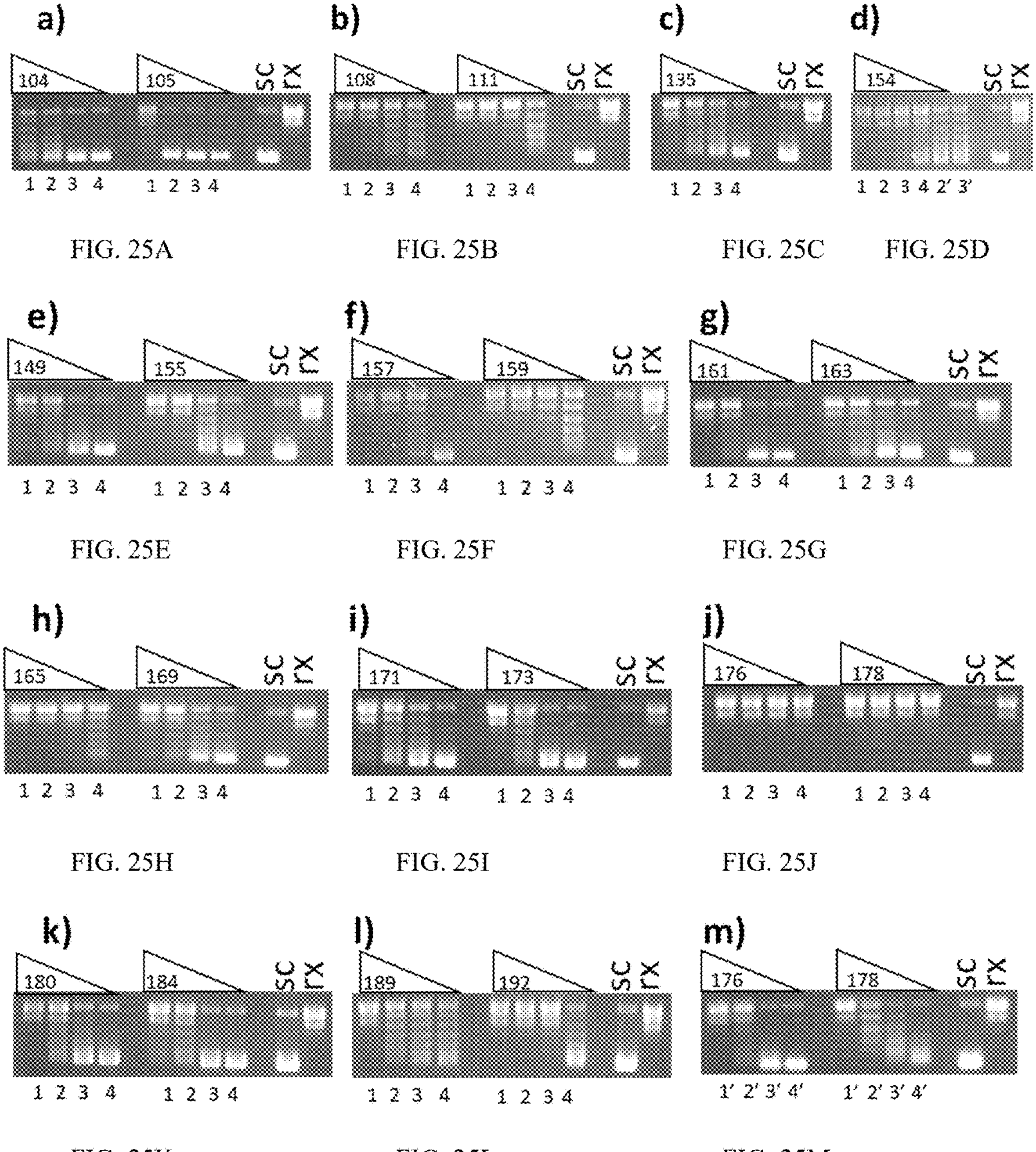
FIGS. 25A-25M show agarose gel-based gyrase inhibition assays to determine the inhibition $IC_{50}$ of MolPort compounds against *E. coli* DNA gyrase. Agarose gel-based gyrase inhibition assays were described in Methods. Compound # are placed above the gels. (A) to (L). Lanes 1-4 correspond, respectively, to 50, 25, 12.5, and 6.25 μM of the compounds used in the assays. (M). Lanes 1'-4' correspond, respectively, to 12.5, 6.25, 3.125, and 1.56 μM of the compounds used in the assays. All compounds' $IC_{50}$ values are less than 50 μM. sc and rx pAB1 are shown.

Agarose gel-based and SDFQ-based titration experiments confirmed the results (FIGS. 24, 25 and 26). Advantageously, new gyrase inhibitors having potent anti-bacterial activities (Tables 3a, 3b and 3c) have been identified.

TABLE 3a

Minimum inhibitory concentration (μM) of new gyrase inhibitors against different bacteria.

| | Minimum Inhibitory Concentration (μM) | | | | |
|---|---|---|---|---|---|
| Compound | *E. coli* | *E. coli imp* | *S. aureus* | *S. aureus* MRSA | *B. subtilis* |
| 4 | N | N | 50 | 50 | 100 |
| 9 | N | N | 3.125 | 3.125 | 25 |
| 21 | N | 100 | N | N | 100 |
| 25 | N | 25 | N | N | N |
| 36 | N | N | N | N | 12.5 |
| 40 | N | N | N | N | 100 |
| 41 | N | N | N | N | 6.25 |
| 44 | N | 25 | 12.5 | 25 | 25 |
| 45 | N | 100 | 100 | 100 | 100 |
| 46 | N | 6.25 | N | N | N |
| 48 | N | N | 3.125 | 3.125 | N |
| 55 | N | N | N | 25 | N |
| 58 | N | 100 | 100 | 100 | 100 |
| 72 | 100 | N | N | N | N |
| 79 | 200 | 50 | 200 | 200 | 100 |
| 82 | N | N | 50 | N | 50 |
| 87 | 25 | 12.5 | 25 | 25 | 6.25 |

TABLE 3b

Minimum inhibitory concentration (μM) of new gyrase inhibitors against different bacteria.

| | MIC (μM) | | | | |
|---|---|---|---|---|---|
| Compound | *E. coli* | *E. coli imp* | *S. aureus* | MRSA | *B. subtilis* |
| 104 | N | 50 | 100 | 100 | 50 |
| 105 | N | 100 | 50 | 100 | 25 |
| 108 | N | 200 | 200 | 200 | N |
| 111 | N | N | N | N | 100 |
| 117 | N | N | 1.56 | 1.56 | N |
| 119 | N | N | 0.78 | 0.78 | N |
| 120 | N | N | 1.56 | 1.56 | N |
| 121 | N | 100 | 3.125 | 3.125 | 50 |

TABLE 3b-continued

Minimum inhibitory concentration (μM) of new gyrase inhibitors against different bacteria.

| | MIC (μM) | | | | |
|---|---|---|---|---|---|
| Compound | *E. coli* | *E. coli imp* | *S. aureus* | MRSA | *B. subtilis* |
| 123 | N | N | 1.56 | 1.56 | 6.25 |
| 124 | N | N | 1.56 | 1.56 | 50-25 |
| 126 | N | N | 100 | 100 | 100 |
| 127 | N | N | 50 | 50 | 25 |
| 128 | N | 50 | 50 | 50 | 25 |
| 132 | N | N | N | N | N |

TABLE 3c

Minimum inhibitory concentration (μM) of new gyrase inhibitors against different bacteria.

| | MIC (μM) | | | | |
|---|---|---|---|---|---|
| Compound | *E. coli* | *E. coli imp* | *S. aureus* | MRSA | *B. subtilis* |
| 134 | N | N | 200 | 200 | N |
| 135 | 200 | 50 | 50 | 50 | 50 |
| 149 | N | N | N | N | N |
| 154 | 50 | 50-100 | 25 | 25 | 25 |
| 155 | N | 100 | 100 | 50 | 50 |
| 157 | N | 100 | 200 | 200 | 200 |
| 159 | N | 200 | 50 | 100 | 200 |
| 161 | N | 200 | N | N | 200 |
| 164 | N | 100 | 200 | 200 | N |
| 173 | N | N | N | 100 | N |
| 180 | N | 100 | N | N | N |
| 184 | N | N | 200 | 200 | N |
| 189 | N | 100 | N | N | 100 |

According to these results, structure activity relationships (SARs) studies of derivatives of several gyrase inhibitors were performed.

Example 3. Psoralen Derivatives as Novel Bacterial DNA Gyrase Inhibitors

There are 3 psoralen derivatives among the hits: compounds 25, 46, and 48 that are potent bacterial DNA gyrase inhibitors although psoralen per se is not a gyrase inhibitor.

Figures 27C, 27D, 27E, 27F, 28A:
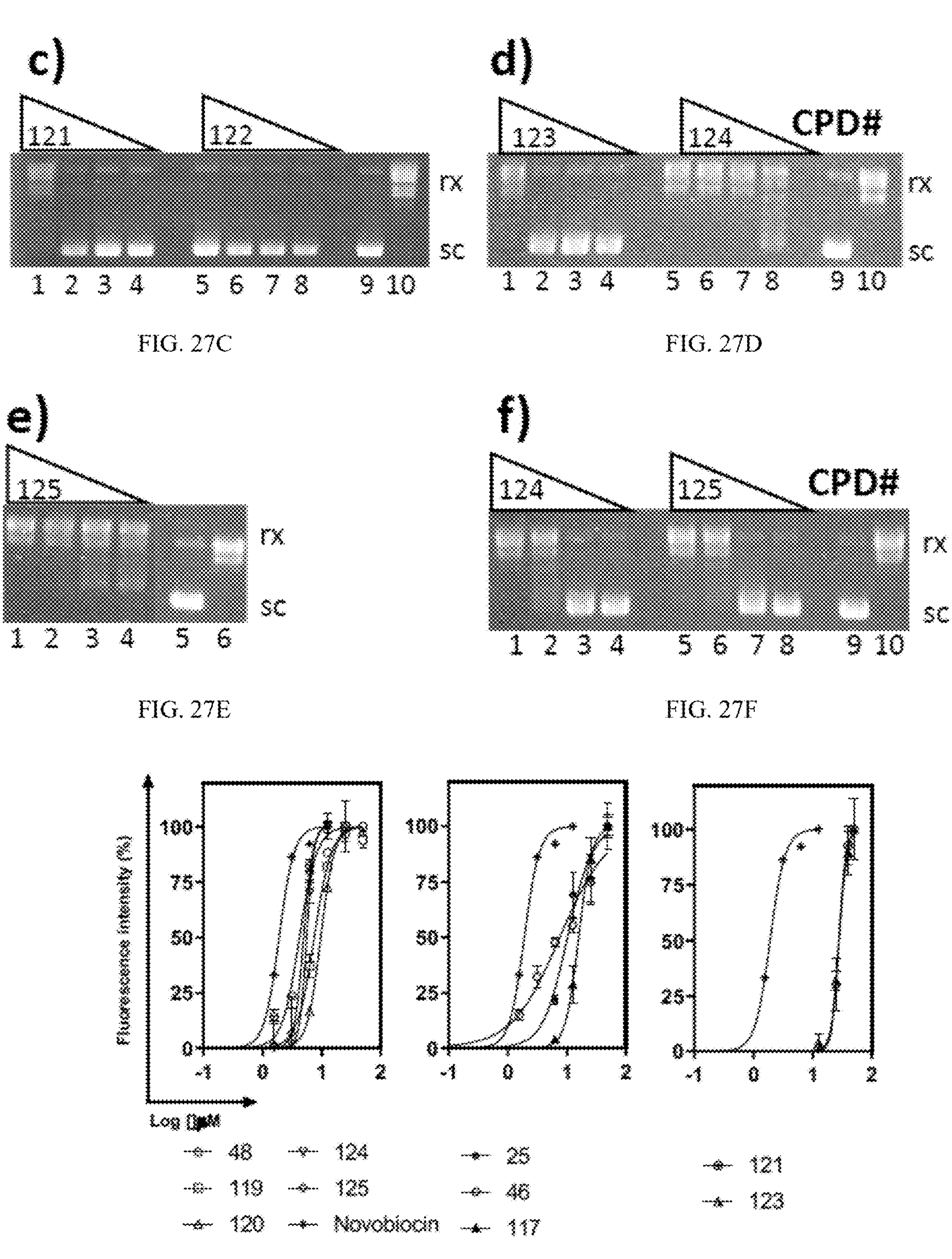

Another 9 psoralen derivatives were purchased and tested in anti DNA gyrase assays using the agarose gel-based and SDFQ-based gyrase assays (FIGS. 27-28). Table 4 shows the chemical structures of psoralen derivatives used in this study.

TABLE 4

Chemical structures of psoralen derivatives.

| Cpd. # | Structure |
|---|---|
| 25 | 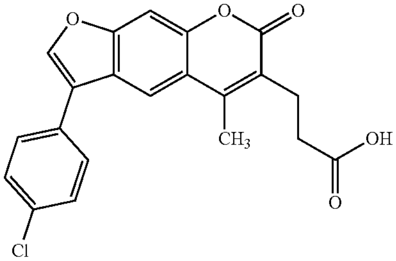 [SMILES: Cc1c(CCC(=O)O)c(=O)oc2cc3occ(-c4ccc(Cl)cc4)c3cc12] |
| 46 | 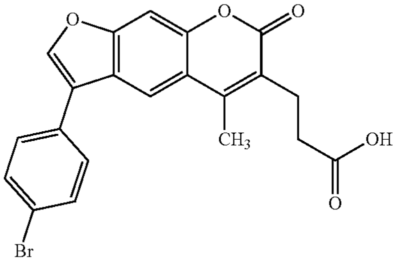 [SMILES: Cc1c(CCC(=O)O)c(=O)oc2cc3occ(-c4ccc(Br)cc4)c3cc12] |
| 48 | 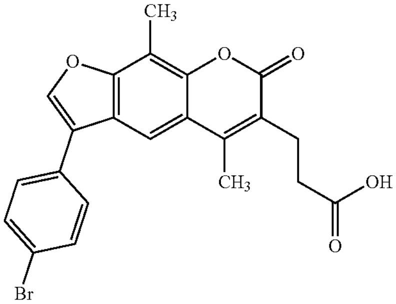 [SMILES: Cc1c(CCC(=O)O)c(=O)oc2c(C)c3occ(-c4ccc(Br)cc4)c3cc12] |
| 117 | 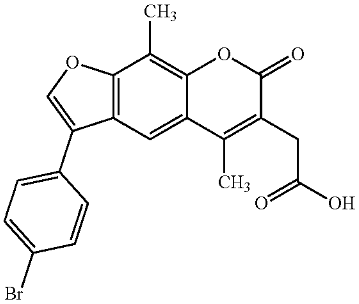 [SMILES: Cc1c(CC(=O)O)c(=O)oc2c(C)c3occ(-c4ccc(Br)cc4)c3cc12] |

TABLE 4-continued

Chemical structures of psoralen derivatives.

| Cpd. # | Structure |
|---|---|
| 118 | 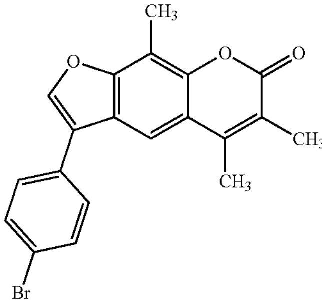 [SMILES: Cc1c(C)c2cc3c(-c4ccc(Br)cc4)coc3c(C)c2oc1=O] |
| 119 | 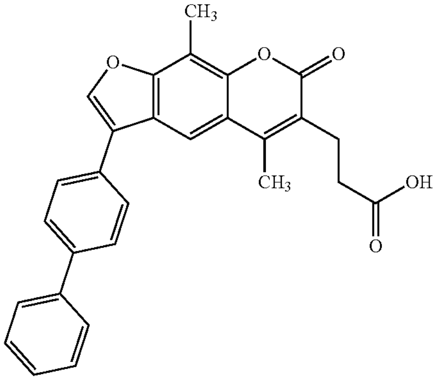 [SMILES: Cc1c(CCC(=O)O)c(=O)oc2c(C)c3occ(-c4ccc(-c5ccccc5)cc4)c3cc12] |
| 120 | 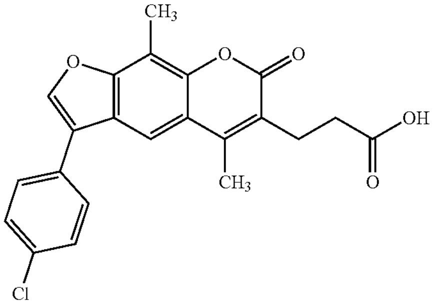 [SMILES: Cc1c(CCC(=O)O)c(=O)oc2c(C)c3occ(-c4ccc(Cl)cc4)c3cc12] |
| 121 | 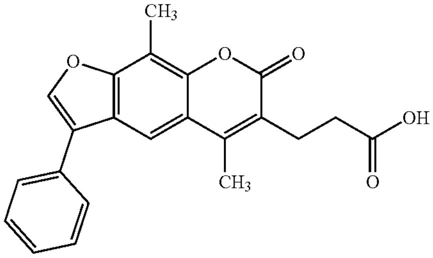 [SMILES: Cc1c(CCC(=O)O)c(=O)oc2c(C)c3occ(-c4ccccc4)c3cc12] |
| 122 | 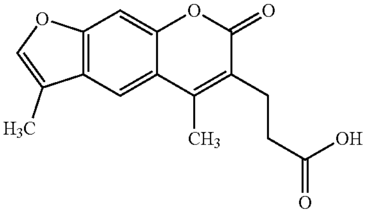 [SMILES: Cc1coc2cc3oc(=O)c(CCC(=O)O)c(C)c3cc12] |

TABLE 4-continued

| Cpd. # | Structure |
|---|---|
| 123 | 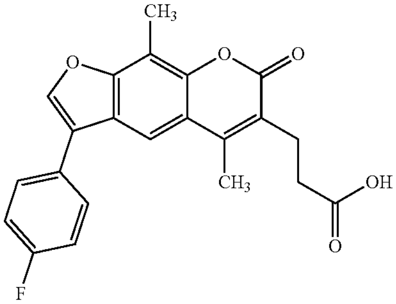 [SMILES: Cc1c(CCC(=O)O)c(=O)oc2c(C)c3occ(-c4ccc(F)cc4)c3cc12] |
| 124 | 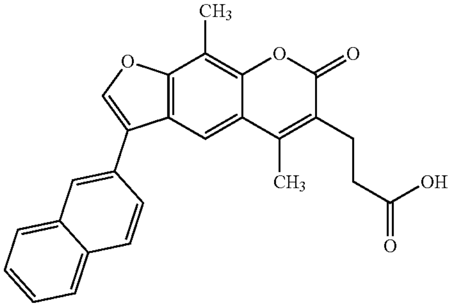 [SMILES: Cc1c(CCC(=O)O)c(=O)oc2c(C)c3occ(-c4ccc5ccccc5c4)c3cc12] |
| 125 | 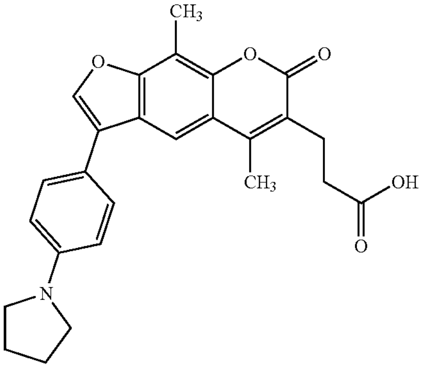 [SMILES: Cc1c(CCC(=O)O)c(=O)oc2c(C)c3occ(-c4ccc(N5CCCC5)cc4)c3cc12] |

Figures 28B, 29:
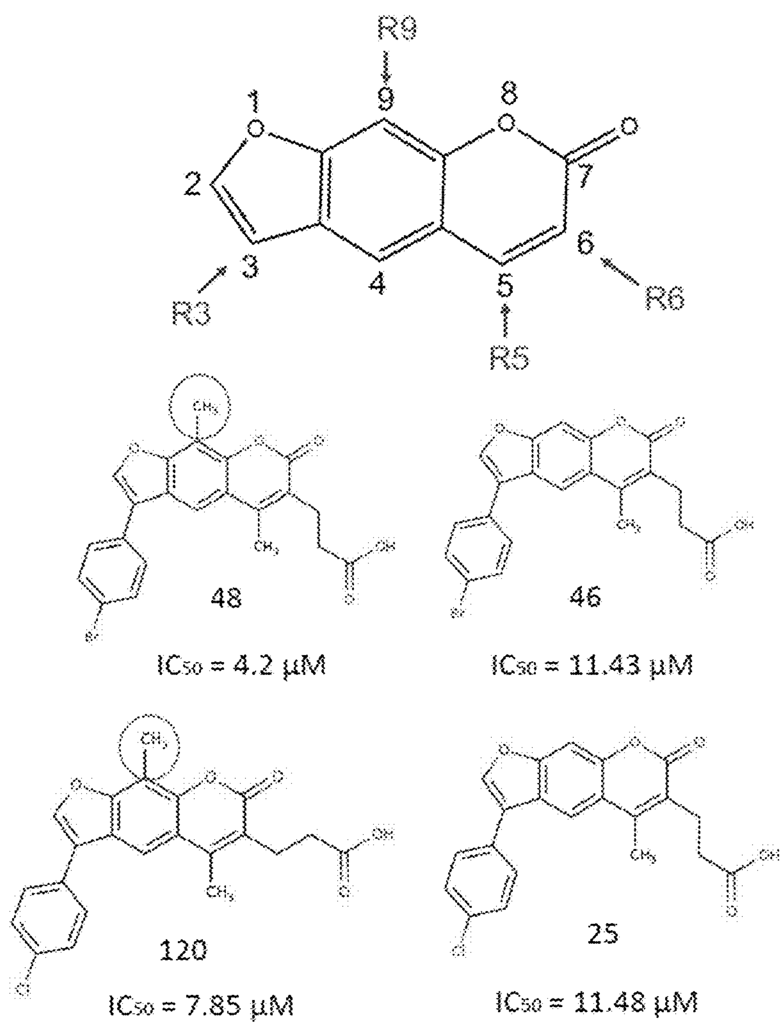
Figure 30A:
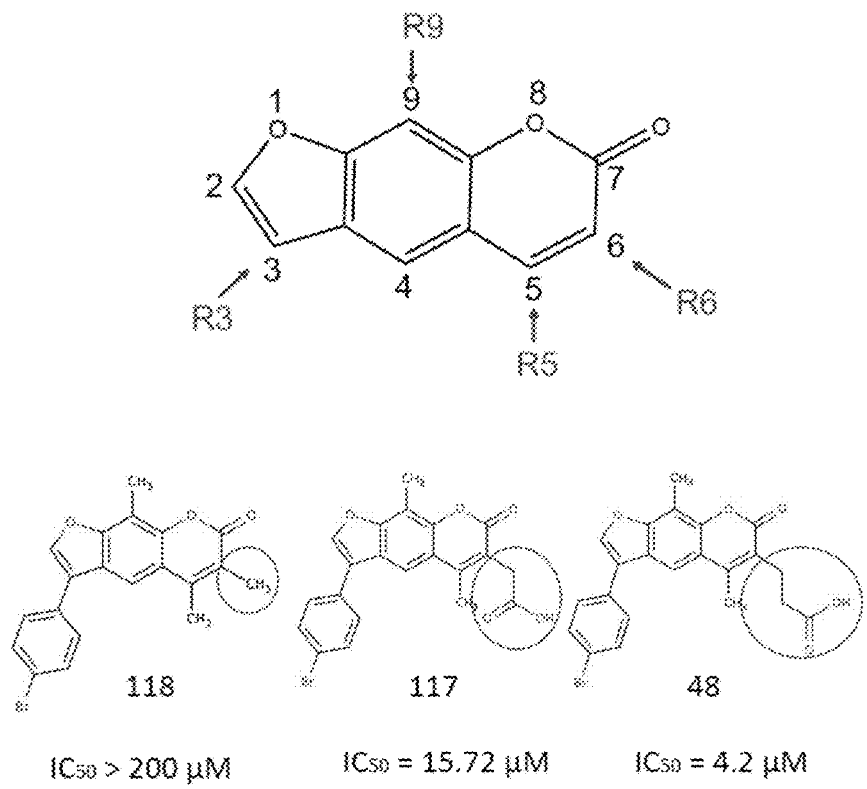
FIGS. 30A-30C show structure-activity relationships. (A) A carboxyl group in R6 is required for the in vitro inhibitory activities against *E. coli* DNA gyrase. (B) A large hydrophobic group at R3 position significantly improves the in vitro inhibitory activities against *E. coli* DNA gyrase. (C) A large hydrophobic group at R3 position significantly improves the in vitro inhibitory activities against *E. coli* DNA gyrase.
Figure 30B:
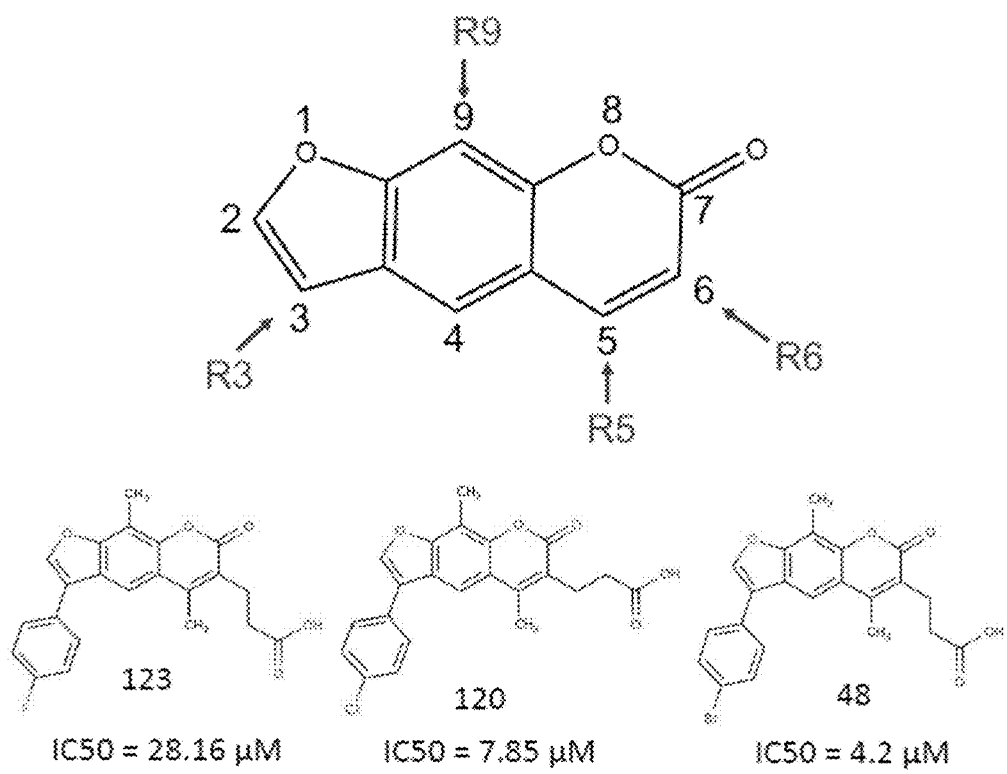
Figure 30C:
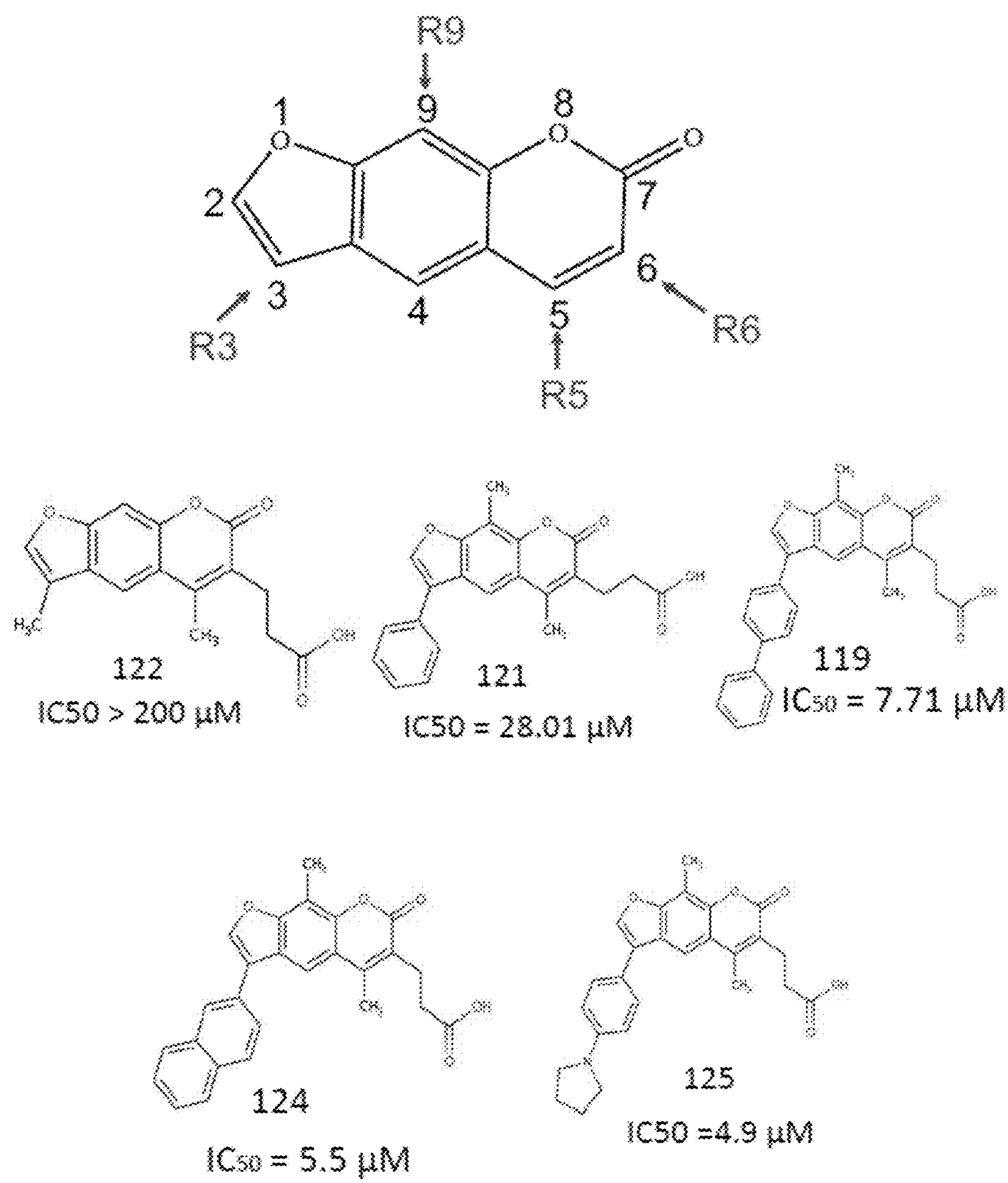

All psoralen derivatives inhibited *E. coli* and Mtb DNA gyrase activities except compounds 118 and 122. Their MIC against *S. aureus* and MRSA were determined (FIG. 28*b*). Antibacterial activities against *E. coli, S. aureus*, MRSA, and Mtb are shown in Table 5. Some exhibited potent activities against Mtb, and *S. aureus* (including a MRSA strain) with 46, 119, and 124 most active for Mtb.

TABLE 5

Psoralen derivatives are potent gyrase inhibitors with antibacterial activities.

| CPD | | | | | $IC_{50}$ (μM) | | MIC (μM) | | % Mtb |
|---|---|---|---|---|---|---|---|---|---|
| # | R3 | R5 | R6 | R9 | EC | Mtb | SA | MRSA | inhibition |
| 25 | 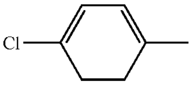 | $CH_3$ | $(CH)_2)_2COOH$ | H | 11.5 | 65 | >200 | >200 | 0.8 |
| 46 | 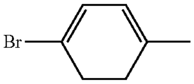 | $CH_3$ | $(CH)_2)_2COOH$ | H | 11.4 | 75 | >200 | >200 | 82.3 |
| 48 | 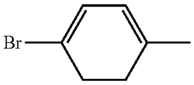 | $CH_3$ | $(CH)_2)_2COOH$ | $CH_3$ | 4.2 | 57 | 3.1 | 3.1 | 38.6 |
| 117 | 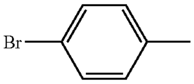 | $CH_3$ | $CH_2COOH$ | $CH_3$ | 15.7 | 50 | 1.6 | 1.6 | 24.7 |
| 118 | 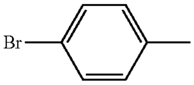 | $CH_3$ | $CH_3$ | $CH_3$ | >200 | >200 | >200 | >200 | 21.8 |
| 119 | 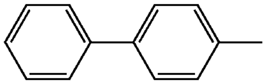 | $CH_3$ | $(CH)_2)_2COOH$ | $CH_3$ | 7.7 | 16 | 0.8 | 0.8 | 70.4 |
| 120 | 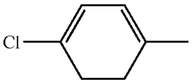 | $CH_3$ | $(CH)_2)_2COOH$ | $CH_3$ | 7.9 | 33 | 1.6 | 1.6 | 18.7 |

TABLE 5-continued

Psoralen derivatives are potent gyrase inhibitors with antibacterial activities.

| CPD | | | | | $IC_{50}$ (μM) | | MIC (μM) | | % Mtb |
|---|---|---|---|---|---|---|---|---|---|
| # | R3 | R5 | R6 | R9 | EC | Mtb | SA | MRSA | inhibition |
| 121 | 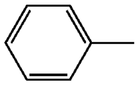 | $CH_3$ | $(CH)_2)_2COOH$ | $CH_3$ | 28 | 58 | 3.1 | 3.1 | 36.7 |
| 122 | $CH_3$ | $CH_3$ | $(CH)_2)_2COOH$ | $CH_3$ | >200 | >200 | >200 | >200 | 15.7 |
| 123 | 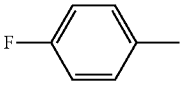 | $CH_3$ | $(CH)_2)_2COOH$ | $CH_3$ | 28.1 | 34 | 1.6 | 1.6 | 31.8 |
| 124 | 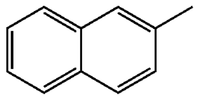 | $CH_3$ | $(CH)_2)_2COOH$ | $CH_3$ | 5.5 | 3 | 1.6 | 1.6 | 80.4 |
| 125 | 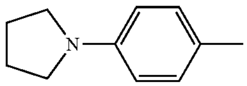 | $CH_3$ | $(CH)_2)_2COOH$ | $CH_3$ | 4.9 | 55 | >200 | >200 | 10.2 |

Figure 31A:
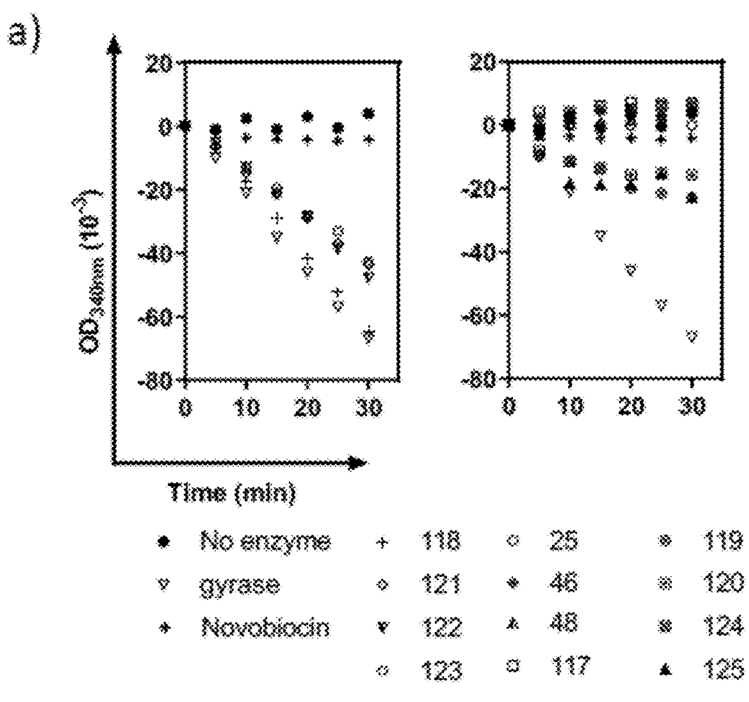
FIGS. 31A-31B show the inhibition of the ATPase activates of *E. coli* DNA gyrase by psoralen derivatives.
Figure 31B:
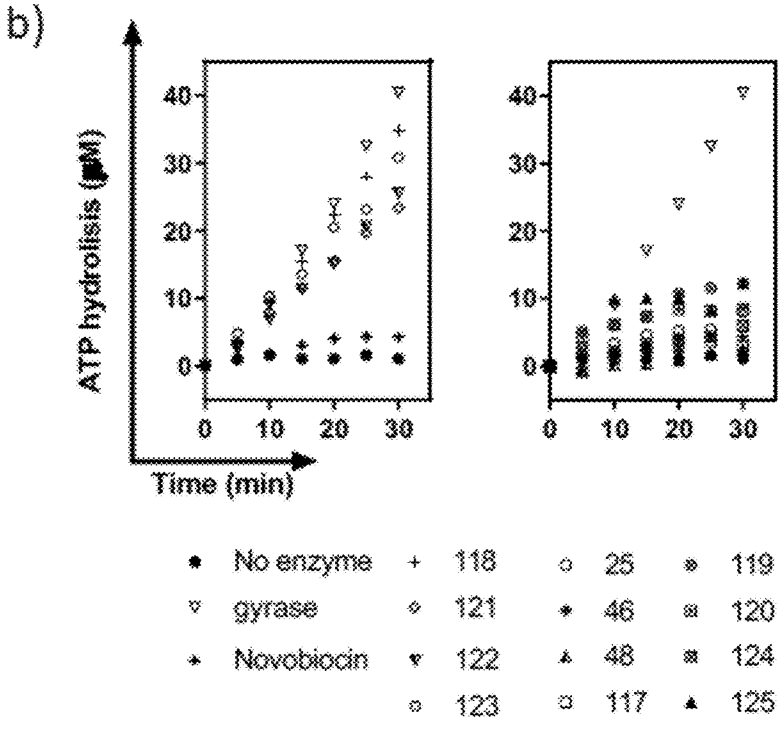
Figures 32A, 32B:
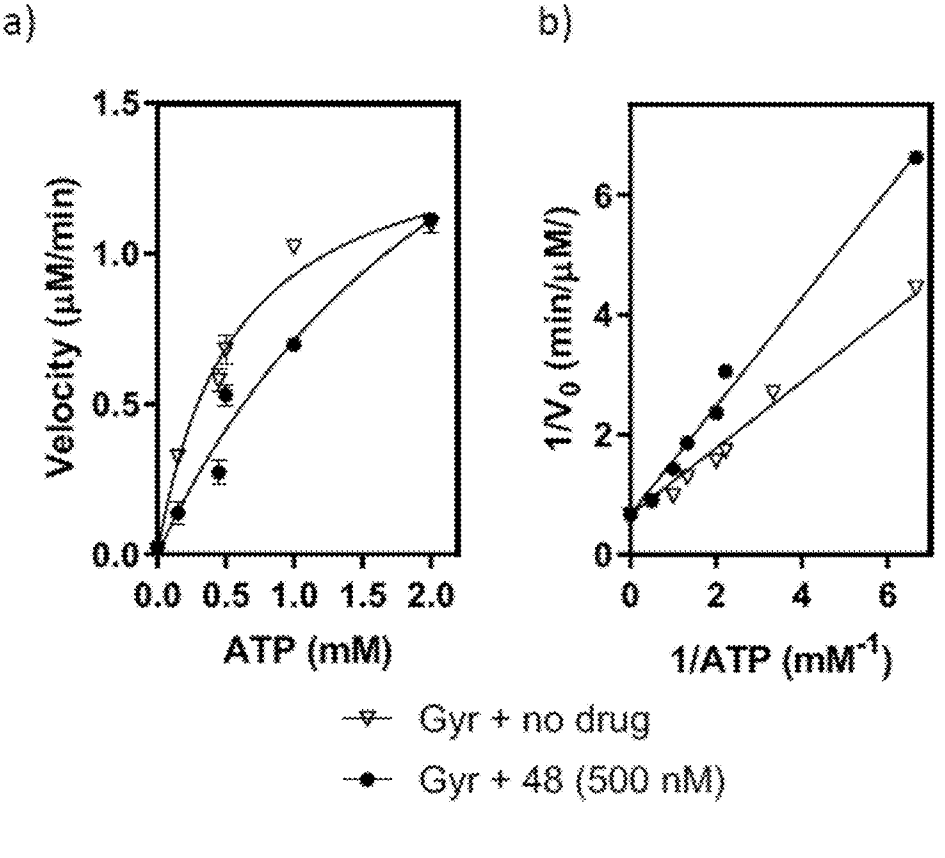
FIGS. 32A-32B show that Psoralen derivative compound 48 is an ATP competitive inhibitor of *E. coli* DNA gyrase.

Interestingly, the results showed that the anti-bacterial activities of these psoralen derivatives are correlated with the anti-DNA gyrase activities (FIG. 28*b*). The methyl group at $R^9$ position enhances the anti-gyrase potency and is required for the anti-bacterial activities against *S. aureus* and MRSA (FIGS. 28 and 29). A bulky hydrophobic group at the 3rd position and a carboxyl group at the $6^{th}$ position are required for the anti-gyrase and anti-bacterial activities (FIGS. 28 and 30A-C). Intriguingly, although compound 125 potently inhibited the *E. coli* DNA gyrase activities, it did not inhibit the growth of *S. aureus* and MRSA (FIG. 28). It is possible that the amine in the bulky hydrophobic group at the 3rd position prevented the entry of the compound to the bacterial cells. The ATPase assays showed that all psoralen derivatives are the ATP competitive inhibitors of DNA gyrase (FIG. 31). A further analysis of compound 48 shows that it inhibited the ATPase activities of *E. coli* DNA gyrase with a Ki (the dissociation constant for the inhibitor) value of 150 nM (FIG. 32).

The results showed that the psoralen analogs do not bind to DNA tightly and also do not cause the photo-induced interstrand DNA crosslinks. A likely reason is that they (except CPD 118) contain a carboxyl group at the $R^6$ position. At neutral pH, these CPDs are negatively charged and should not bind to DNA with high affinity. These CPDs contain a bulky hydrophobic group at the $R^3$ position that prevents them from intercalating into DNA base pairs. They also do not strongly inhibit human DNA TopoIIα with $IC_{50}$ more than 100 μM for all psoralen derivatives. For instance, the results show that the $IC_{50}$ of CPDs 119 and 124 against human TopoIIα are 133 and 117 μM, respectively. This yields selectivity index (Mtb gyrase over human TopoIIα) of 8.3 and 39 for these two CPDs.

Consistent with this data, psoralen analogs displayed excellent selectivity, with no cytotoxicity evident after treatment of two cell lines (J774, HepG2) with 200 μM of CPDs 46, 119, and 124 (Table 6). The Mtb active hits also include isatin-phenylhydrazones (CPDs 127, 128), pyrido-thieno-pyrimidines (CPD 19), amino-benzothiazoles (CPD 178), and thiazolo[3,2-a]benzimidazoles (CPD 47).

TABLE 6

Selective anti-Mtb gyrase inhibitors

| | % inhibition | $IC_{50}$ (μM) | |
|---|---|---|---|
| Compounds # | (20 μM) | J774 | HepG2 |
| NSC229 | 99.3 | NT | NT |
| 46 | 82.3 | >200 | >200 |
| 119 | 70.4 | >200 | >200 |
| 124 | 80.4 | >200 | NT |
| 127 | 97.8 | NT | NT |
| 128 | 67.1 | NT | NT |
| 178 | 84.8 | NT | NT |
| 19 | 75 | >200 | >200 |
| 30 | 82.4 | NT | NT |
| 47 | 79.3 | NT | NT |
| 54 | 78.6 | NT | NT |
| 110 | 100 | >200 | NT |
| NSC212 | 84.6 | NT | NT |
| 64 | 88 | NT | NT |

>200: loss of cell viability only at highest [drug]
NT = no toxicity at highest concentration (200 μM)

Figures 34C, 34D, 35A, 35B:
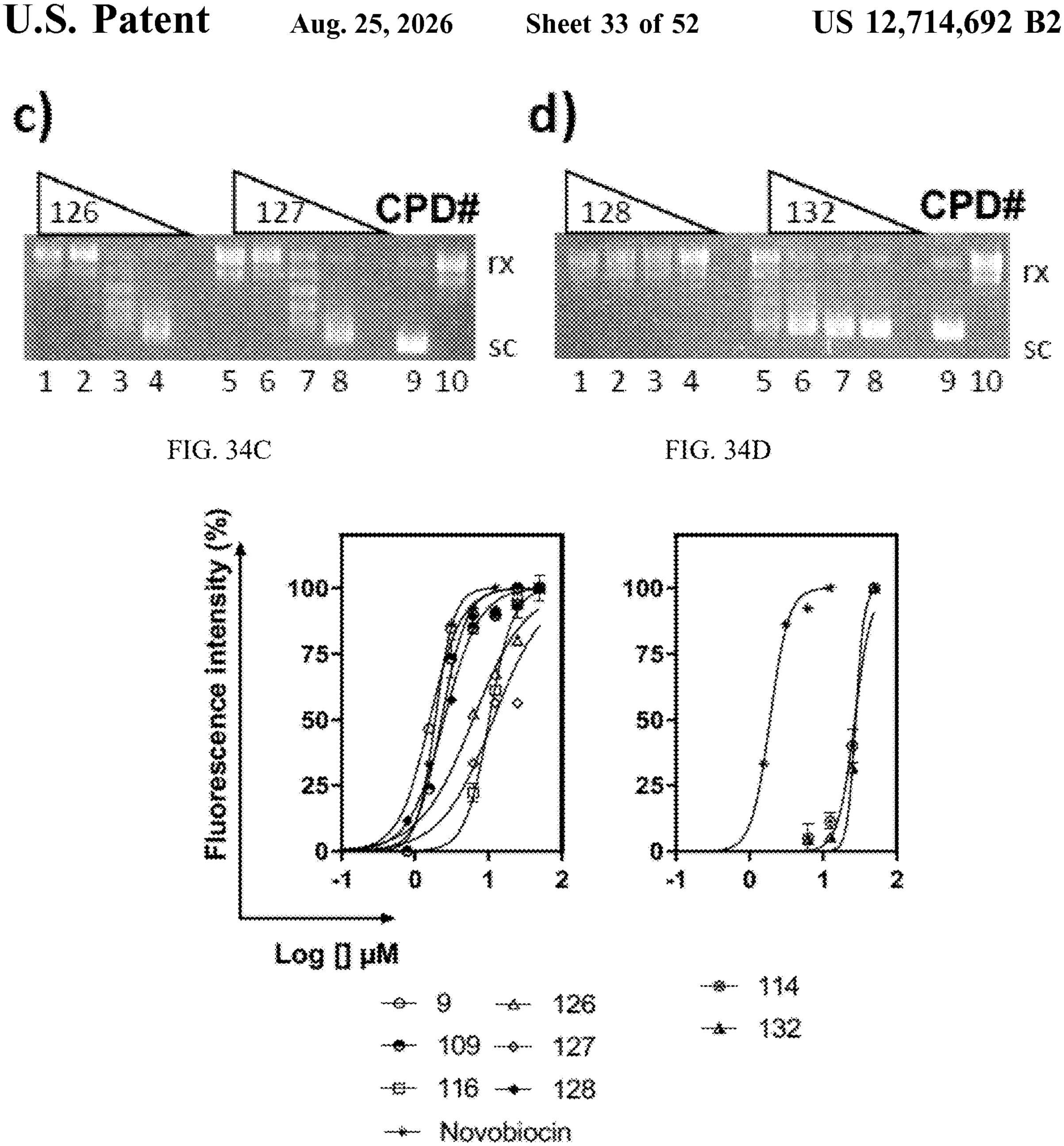

Example 4. 4-[2-(5,7-Dimethyl-2-oxoindol-3-yl)hydrazinyl]benzoic acid (compound 9) and derivatives Since 4-[2-(5,7-Dimethyl-2-oxoindol-3-yl)hydrazinyl]benzoic acid (compound 9) is a potent gyrase inhibitor and strongly inhibited the growth of *S. aureus* and MRSA, 9 derivatives of compound 9 were tested to examine their anti-gyrase and anti-bacterial activities (FIG. 33). The carboxyl group at position 1 is required for the anti-bacterial activities against *S. aureus* and MRSA (FIGS. 34 and 35). Changing the carboxyl group to a different group also reduced their anti-gyrase activities (FIGS. 34 and 35).

Example 5. Several Common Dyes Potently Inhibit *E. coli* DNA Gyrase Activities

Figure 36:
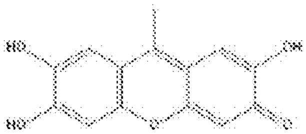
FIG. 36 shows chemical structures of certain common dyes and natural products that inhibit *E coli* DNA gyrase potently.
Figure 36:
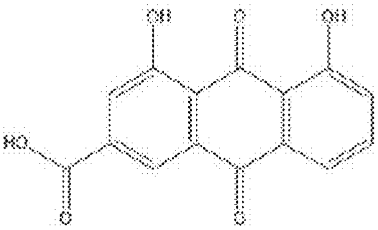
Figure 36:
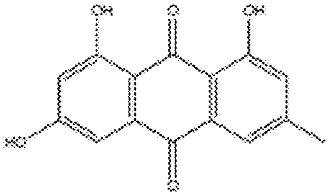
Figure 36:
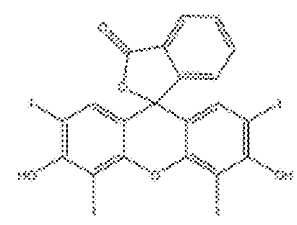
Figure 36:
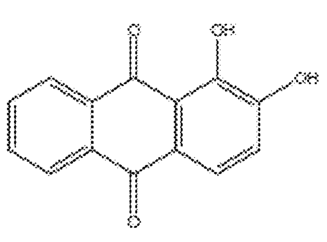
Figure 36:
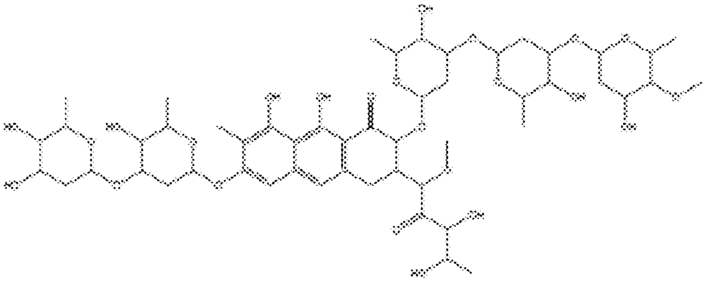

Several common dyes including erythrosine B (Red No. 3), alizarin (Mordant Red 11 or Turkey Red), and methyl fluorone black strongly inhibit *E. coli* DNA gyrase activities with $IC_{50}$ less than 10 μM (FIG. 36). Emodin and rhein, two anthraquinones with similar structures also potently inhibited *E. coli* DNA gyrase activities (FIG. 36).

Example 6. Antibiotic Variamycin is a Potent Gyrase Inhibitor

Antibiotic variamycin (mithramycin or plicamycin) is an antitumor antibiotic produced by *Streptomyces plicatus*. It strongly inhibited *E. coli* DNA gyrase activities (FIG. 36).

Figure 37:
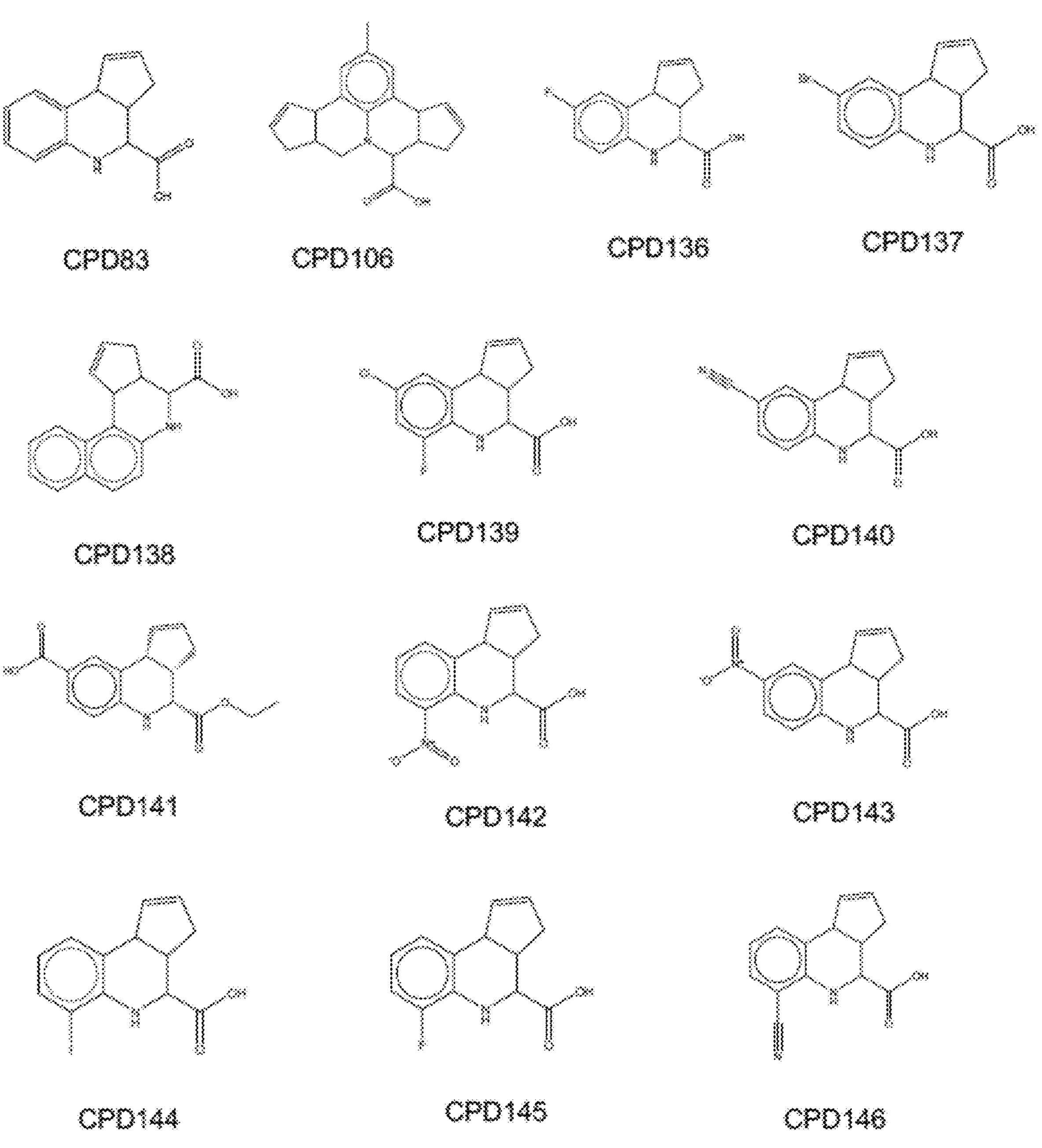
FIG. 37 shows chemical structures of 3a,4,5,9b-Tetrahydro-3H-cyclopenta[c]quinoline-4-carboxylic acid and derivatives. Compounds 83, 106, 141, and 144 inhibit *E. coli* DNA gyrase strongly. All derivatives inhibit *E. coli* DNA gyrase at 50 μM.

Example 7. 3a,4,5,9b-Tetrahydro-3H-cyclopenta[c]quinoline-4-carboxylic acid and Derivatives FIG. 37 shows the chemical structures of 3a,4,5,9b-Tetrahydro-3H-cyclopenta[c]quinoline-4-carboxylic acid and derivatives. They all inhibited *E. coli* DNA gyrase activities.

Figure 38:
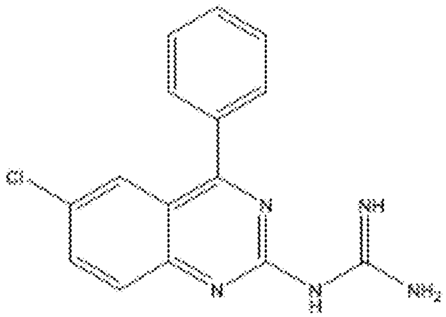
FIG. 38 shows chemical structures of new bacterial DNA gyrase inhibitors that cause DNA nicking (NK) and double stranded DNA breaks (DSDB).
Figure 38:
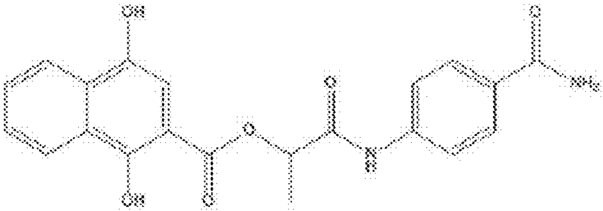
Figure 38:
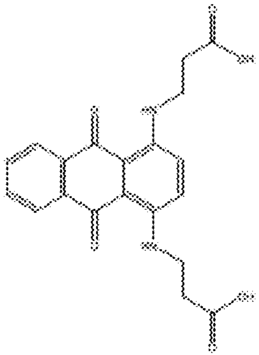
Figure 38:
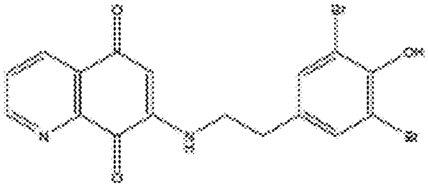

Example 8. New Gyrase Inhibitors Causing Double Stranded DNA Breaks and DNA Nicking Several compounds cause DNA gyrase-mediated double stranded DNA breaks and DNA nicking. These compounds may also be DNA gyrase poisons. N-(6-chloro-4-phenylquinazolin-2-yl)guanidine (compound 154, FIG. 38) causes DNA gyrase-mediated double stranded DNA breaks. 1-[(4-carbamoylphenyl)carbamoyl]ethyl 1,4-dihydroxynaphthalene-2-carboxylate (compound 40, FIG. 38) causes DNA gyrase-mediated double stranded DNA breaks and DNA nicking. 3-({4-[(2-carboxyethyl)amino]-9,10-dioxo-9,10-dihydroanthracen-1-yl}amino)propanoic acid (compound 173, FIG. 38) and 7-((2-(3,5-Dibromo-4-hydroxyphenyl)ethyl)amino)-5,8-quinolinedione (compound 232, NSC668394, FIG. 38) cause DNA nicking.

Compound 154 is a quinazoline derivative and strongly inhibits *E. coli* DNA gyrase activities with an $IC_{50}$ of 7 μM (FIGS. 39A and 39B). Intriguingly, compound 154 also causes the gyrase-mediated DNA double-stranded breaks and single-stranded nicks (FIG. 39C). A likely MoA of this gyrase inhibitor is to stabilize the enzyme-DNA cleavage-complex, which leads to the DNA breaks and nicks.

In other words, compound 154 is a bacterial DNA gyrase poison. Although the induced DNA breaks and nicks are generally proportional to the added inhibitor, high concentrations of compound 154 inhibit the formation of the double-stranded DNA breaks (compare lanes 4 to 6 of FIG. 39C). The result shows that compound 154 inhibits human DNA topoisomerase 2a with an estimated $IC_{50}$ of ~50 μM (FIG. 39D). Surprisingly, compound 154 also causes the human topoisomerase 2α-mediated DNA nicks and double-stranded breaks (FIG. 39E). Thus, compound 154 is a human DNA topoisomerase 2a poison as well.

FIG. 39F shows that compound 154 is a novel gyrase poison that inhibits *E. Coli* DNA gyrase and Topoisomerase IV. FIGS. 39G and 39H show molecular models of compound 154 binding to gyrase-DNA complexes. The molecular modeling results show that compound 154 intercalates into DNA base pairs near the gyrase cleavage sites in the gyrase-DNA-drug complex.

Figure 40D:
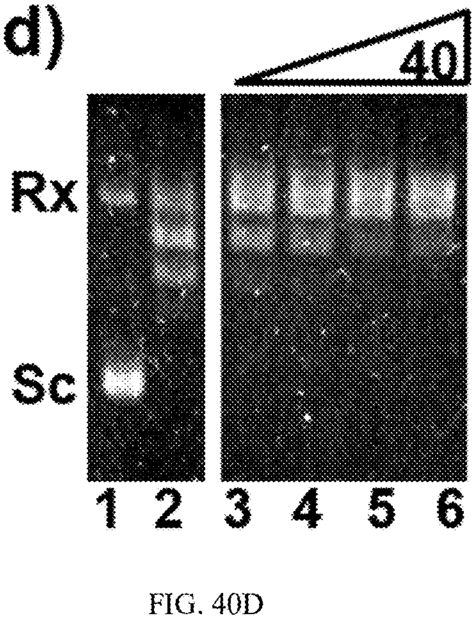
Figure 40E:
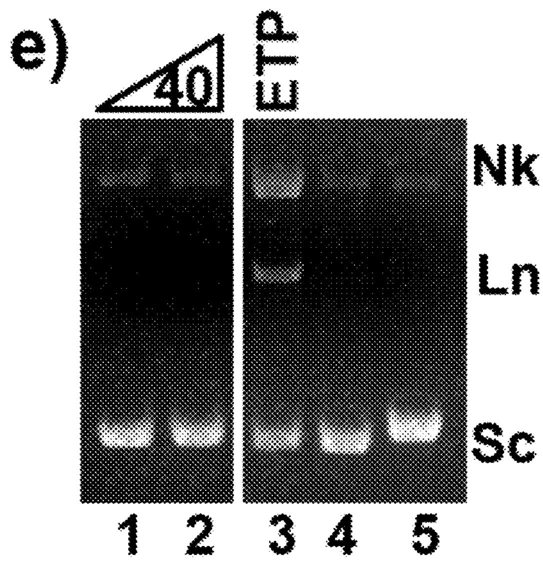

Compound 40 also inhibits *E. coli* DNA gyrase activities with an $IC_{50}$ of 50 μM (FIGS. 40A and 40B). Similar to compound 154, it causes gyrase-mediated DNA double-stranded breaks and single-stranded nicks, and is a bacterial DNA gyrase poison (FIG. 40C). Compound 40 causes much more DNA nicks than double-stranded DNA breaks (compare lanes 1 to 4 of FIG. 40C). Compound 40 does not inhibit human DNA topoisomerase 2α (FIG. 40D). It does not cause the human topoisomerase 2α-mediated DNA nicks and double-stranded breaks (FIG. 40E).

Compound 154 shows significant antibacterial activities against bacterial strains including the wildtype *E. coli* strain ATCC 25922, *Staphylococcus aureus* ATCC 14775, and MRSA (ATCC 33591) (Table 3c). Compound 40 shows anti *Bacillus subtilis* activities at 39 μg/mL. Intriguingly, the anti-bacterial activities of these psoralen derivatives are correlated with the anti-DNA gyrase activities.

Figure 40F:
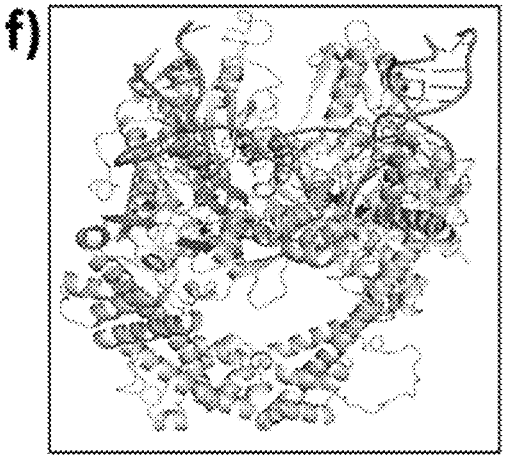
Figure 40G:
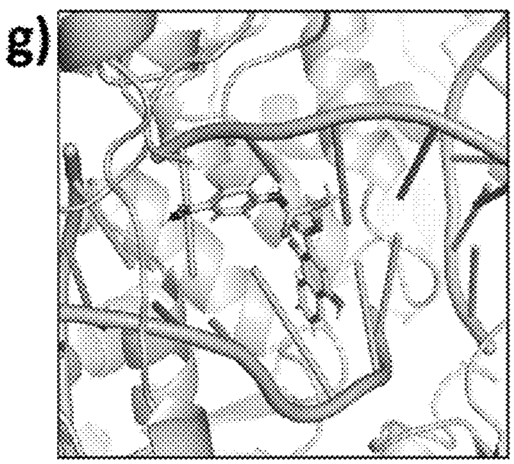
Figure 41A:
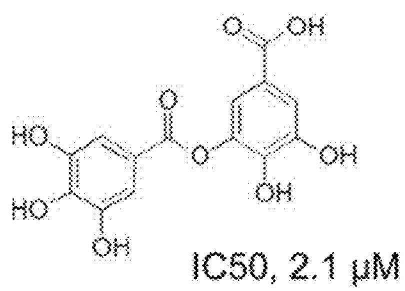
FIGS. 41A-41F show chemical structure of gallic acid derivatives. (A) digallic acid, (B) butyl gallate, (C) octyl gallate, (D) dodecyl gallate, (E) phenyl gallate and (F) bi-phenyl gallate. The inhibition $IC_{50}$ values against *E. coli* DNA gyrase were determined by SDFQ or agarose gel based DNA gyrase assays.
Figure 41B:
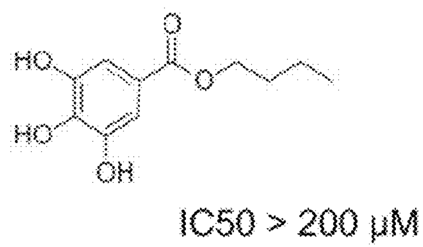
Figure 41C:
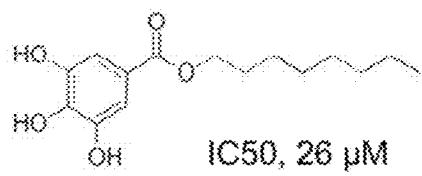
Figure 41D:
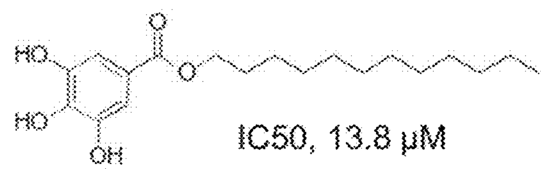
Figure 41E:
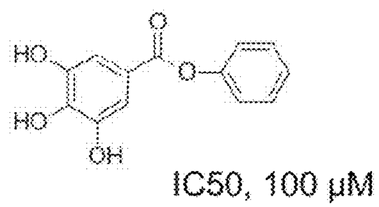
Figure 41F:
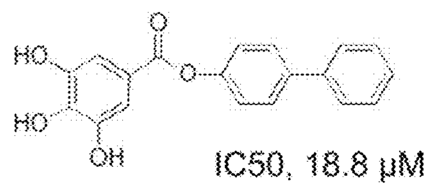

Molecular modeling studies were performed based on a cryoEM structure of *E. coli* DNA gyrase nucleoprotein complex with gepotidacin, an NTBI. The molecular modeling results show that the fused six-member aromatic ring system intercalates into DNA base pairs of the nicking site (FIGS. 40F and 40G), and the benzamide group lies on the floor of the major groove (FIGS. 40F and 40G), unlike the binding of gepotidacin to the gyrase nucleoprotein complex likely due to the short linker of compound 40.

Example 9. Digallic Acids and Derivatives as New Gyrase Inhibitors

Digallic acid and derivatives potently inhibit bacterial DNA gyrase and have anti-bacterial activities (FIG. 41 and Table 7).

TABLE 7

| Antimicrobial activity of gallic acid derivatives | | | | | |
|---|---|---|---|---|---|
| | MIC (μg/mL) | | | | |
| Compound | *B. subtilis* ATCC 6633 | *S. aureus* ATCC 14775 | *S. aureus* (MRSA) ATCC BAA44 | *E. coli* ATCC 25922 | *E. coli imp* |
| Digallic acid | >64 | 64 | 64 | N/A | N/A |
| Butyl gallate | >64 | N/A | N/A | N/A | N/A |
| Octyl gallate | 4 | 56.46 | 56.46 | 225.86 | 14.11 |
| Dodecyl gallate | 8 | 67.68 | 67.68 | N/A | 67.68 |
| Phenyl gallate | >64 | 64 | 64 | N/A | N/A |
| Biphenyl gallate | 16 | 16 | 16 | 517.29 | 36.43 |
| Ciprofloxacin | <2 | <2 | <2 | 2 | <2 |

Figure 42A:
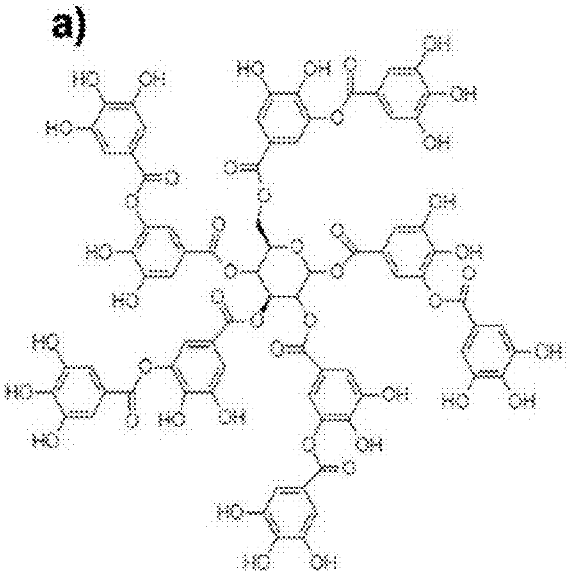
Figures 42B, 42C, 42D:
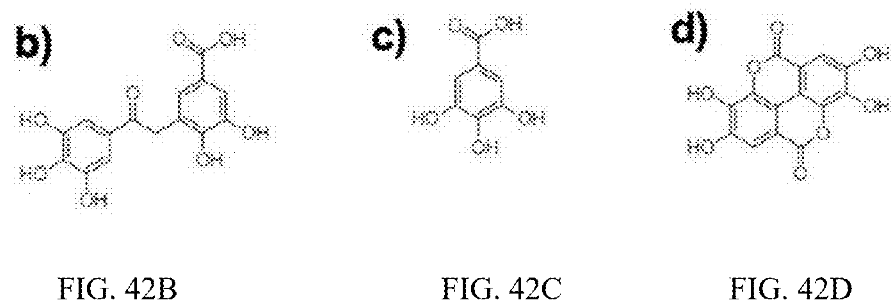
Figures 42E, 42F:
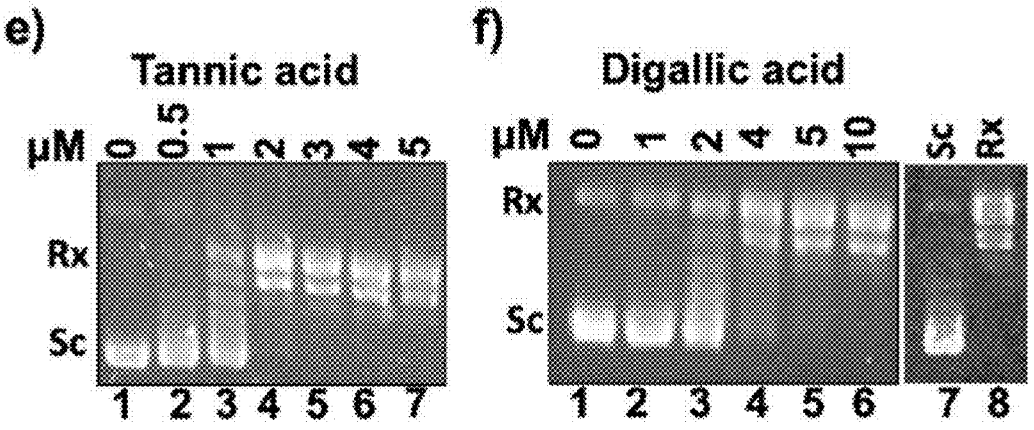

Polyphenols such as ellagic acid and EGCG, and 3,5-dicaffeoylquinic acid strongly inhibit *E. coli* DNA gyrase (FIG. 42). Tannic acid also potently inhibits *E. coli* DNA gyrase with an IC50 of 1 μM (FIG. 42E). Digallic acid potently inhibits *E. coli* DNA gyrase with an estimated IC50 of 2 μM (FIG. 42F). In contrast, gallic acid does not inhibit *E. coli* DNA gyrase up to 500 μM (FIG. 42G, and Table 8).

TABLE 8

IC50 values [μM] of gallate derivatives against *E. coli* DNA gyrase and topoisomerase IV.

| Compound | Gyrase | | Topoisomerase IV | |
|---|---|---|---|---|
| | Gel-based | SDFQ | Gel-based | SDFQ |
| gallic acid | >500 | N/A[a] | >500 | N/A[a] |
| digallic acid | 2 | 1.9 | 8 | 7.3 |
| butyl gallate | >100 | >100 | >100 | >100 |
| octyl gallate | 50 | 25.96 | 50 | 41.2 |
| dodecyl gallate | 15 | 13.77 | 50 | 36.9 |
| phenyl gallate | >100 | >100 | >100 | >100 |
| biphenyl gallate | 20 | 18.8 | 25 | 23.6 |
| novobiocin | 0.5 | 0.45 | 10 | 4.3 |

[a]Not available.

Next, several compounds with a gallic acid or gallate attached to a hydrophobic moiety through an ester bond (FIGS. 41B-F) were tested for their inhibition activities against *E. coli* DNA gyrase. The results are shown in FIGS. 43A and 43B. All these gallate derivatives inhibit *E. coli* DNA gyrase (FIG. 43 and Table 8). Interestingly, a long hydrophobic chain or group significantly increases the inhibition activities of these gallate derivatives against *E. coli* DNA gyrase. For example, the IC50 value of dodecyl gallate is much lower than that of butyl gallate (FIG. 43 and Table 8). Likewise, the IC50 value of biphenyl gallate is also lower than that of phenyl gallate (FIG. 43 and Table 8).

The inhibition of *E. coli* DNA gyrase by these gallate derivatives was also confirmed using a supercoiling-dependent fluorescence quenching (SDFQ) assay (FIG. 44A). As shown in FIG. 44A, supercoiling of the fluorescently-labeled plasmid pAB1_FL905 greatly decreases the fluorescence intensity of the plasmid. In the presence of a gyrase inhibitor, the fluorescence intensity of pAB1_FL905 should not change. The SDFQ assay is an excellent assay to quantitatively analyze the inhibition of DNA gyrase by inhibitors. Indeed, the IC50 values obtained through the SDFQ assays are almost identical to those obtained by gel-based gyrase inhibition assays (Table 8).

Previous studies showed that ellagic acid (a condensed dimer of gallic acid) and epigallocatechin gallate (a gallate derivative) are competitive inhibitors of bacterial DNA gyrase's ATPase. Thus, the ATPase kinetic studies were conducted in the absence or presence of digallic acid or other gallate derivatives. The results are shown in FIGS. 44C and 44D. Digallic acid and other gallate derivatives greatly inhibit the ATPase activities of *E. coli* DNA gyrase. Fitting of these kinetic results to the Michaelis-Menten equation yielded the following kinetic parameters: $K_M$ of 0.59±0.22 mM and $V_{max}$ of 16.3±2.5 nM/s in the absence of an inhibitor and $K_M$ of 1.44±0.73 mM and $V_{max}$ of 17.8±5.0 nM/s in the presence of 500 nM of digallic acid. These results demonstrate that digallic acid is a competitive inhibitor of bacterial DNA gyrase's ATPase (FIG. 44C): the intercept on the $1/V_0$ axis of the Lineweaver-Burk or double-reciprocal plot is the same in the presence or absence of digallic acid showing that digallic acid competes with ATP for its binding sites of *E. coli* gyrase. The Ki was calculated to be 347 nM.

The inhibition activities of digallic acid and other gallate derivatives against *E. coli* DNA topoisomerase IV were also tested. The results are shown in FIG. 45 for relaxation. Novobiocin is a known topoisomerase IV inhibitor with an IC50 of ~10 μM. Digallic acid potently inhibits *E. coli* topoisomerase IV with an estimated IC50 ~8 μM for relaxation (FIGS. 45A and 45D) and ~4 μM for decatenation. Octyl gallate, dodecyl gallate, and biphenyl gallate also strongly inhibit *E. coli* DNA topoisomerase IV (FIGS. 45B, C and D, Table 8). Interestingly, digallic acid and these gallate derivatives also inhibit the ATPase activities of bacterial DNA topoisomerase IV (FIG. 45E). In contrast, at 100 μM, digallic acid and other gallate derivatives do not inhibit *E. coli* DNA topoisomerase I (FIG. 46A), human DNA topoisomerase I (FIG. 46B), and IIα (FIG. 46C). These results suggest that these gallic acid derivatives only target bacterial DNA gyrase and topoisomerase IV. Additionally, the DNA cleavage assays showed that digallic acid and other gallate derivatives are not bacterial DNA gyrase poisons, specific DNA gyrase inhibitors that stabilize and stimulate gyrase-mediated double-stranded breaks and single-stranded nicks (FIG. 46D).

Figures 47D, 47E, 47F:
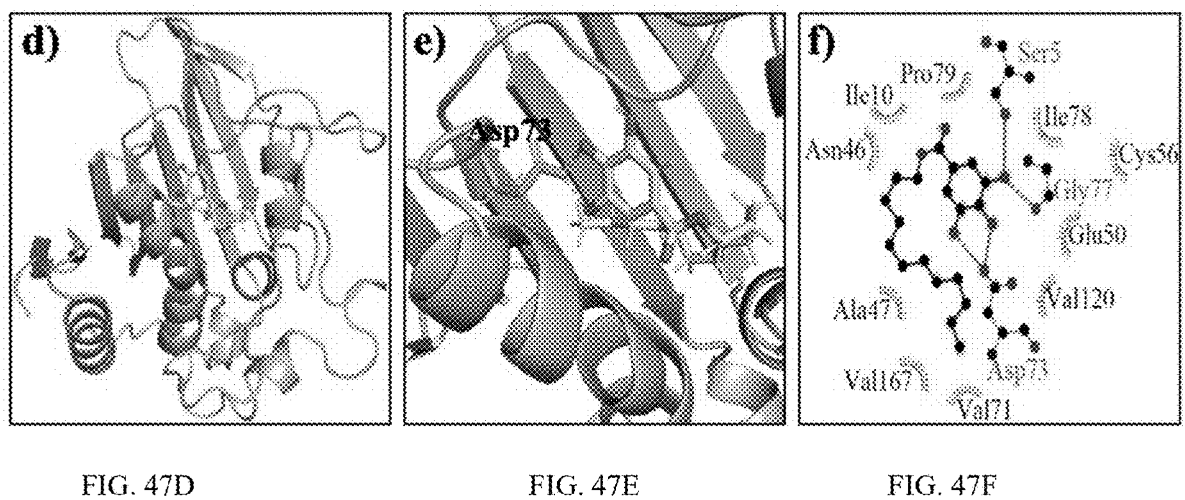
Figures 47G, 47H, 47I:
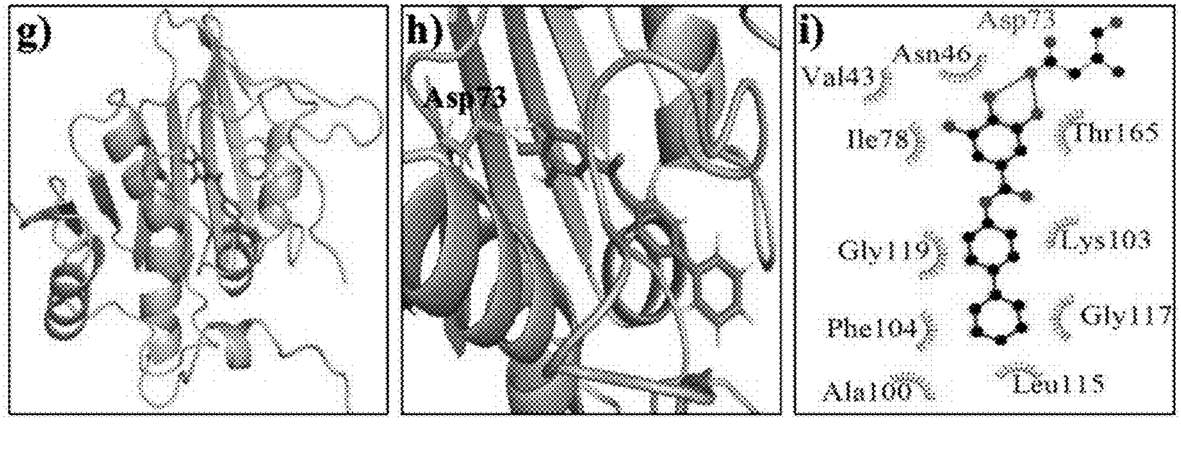

FIG. 47 shows molecular models for digallic acid, dodecyl gallate, and biphenyl gallate binding to *E. coli* DNA gyrase B subunit. These models were generated by molecular docking with the crystal structure of gyrase B subunit (PDB ID: 1E11), followed by 100 ns molecular dynamics simulations. The method is validated by docking ADPNP to *E. coli* DNA gyrase subunit B followed by molecular dynamic simulation, which resulted in a similar complex to the experimentally obtained ADPNP-*E coli* DNA gyrase complex (PDB ID: 1EI1). Similar to novobiocin, digallic acid, dodecyl gallate, and biphenyl gallate also bind to the ATP binding site of the gyrase B subunit. Digallic acid, dodecyl gallate or biphenyl gallate form a hydrogen bond with Asp73 (FIG. 47). It is found that the hydrophobic groups of gallate derivatives are in contact with the hydrophobic amino acids, which may greatly enhance the inhibition against *E. coli* DNA gyrase.

The antibacterial activities of digallic acids and these gallate derivatives were tested and their MICs against several bacterial strains were determined. The results are summarized in Table 9. Octyl and dodecyl gallate showed antibacterial activities against *B. subtilis, S. aureus*, and MRSA. Digallic acid also showed some antibacterial activities against these two gram-positive bacteria. Interestingly, the antibacterial activities of these gallate derivatives coincided with their inhibition against bacterial DNA gyrase, suggesting that DNA gyrase is a potential target for these compounds for their antibacterial activities. Biphenyl gallate showed some antibacterial activities against *E. coli*.

TABLE 9

Antibacterial activity of gallate derivatives.

| Bacterial strains | MIC (μM) | | | | | | | |
|---|---|---|---|---|---|---|---|---|
| | Digallic acid | Butyl gallate | Octyl gallate | Dodecyl gallate | Phenyl gallate | Biphenyl gallate | Ciprofloxacin | Novobiocin |
| *S. aureus* ATCC 14775 | 200 | >200 | 200 | 200 | 200 | 50 | 1.25 | <6.25 |
| MRSA ATCC 33591 | 200 | >200 | 100 | 200 | 200 | 50 | 40 | <6.25 |

TABLE 9-continued

Antibacterial activity of gallate derivatives.

| Bacterial strains | MIC (μM) Digallic acid | Butyl gallate | Octyl gallate | Dodecyl gallate | Phenyl gallate | Biphenyl gallate | Ciprofloxacin | Novobiocin |
|---|---|---|---|---|---|---|---|---|
| *B. subtilis* ATCC 6633 | >200 | >200 | 12.5-25 | 25-50 | >200 | 50-100 | 0.4 | <6.25 |
| *E. coli* ATCC 25922 | >200 | >200 | >200 | >200 | >200 | >200 | 0.0125 | 157.5 |
| *E. coli* imp BAS3023 | >200 | >200 | 50 | 200 | >200 | 200 | 0.0019 | 6.25 |

One advantage of these new gallate-based gyrase inhibitors is that they can be easily modified/derivatized to enhance their potency. For instance, new functional groups can be attached to the gallate through an ester or amide bond.

Example 10. Compound 229 and Analogs are Novel Bacterial DNA Gyrase Poisons with Potent Anti-Bacterial Activities Based on the SDFQ assay, a miniaturized, automated HTS assay of *E. coli* gyrase was established in the 1536-well plate format and 370,620 CPDs of MLSMR were screen at 5 μM. Compound 229, an 4-(1-methylimidazo[1,2-a]pyridine-1-ium derivative, is a promising novel gyrase inhibitor. It inhibits *E. coli* gyrase with an estimated $IC_{50}$ of 16 μM (FIG. 48A) and enhances the *E. coli* gyrase-mediated DNA nicking (FIG. 48B). This compound is an even more potent inhibitor of Mtb DNA gyrase with an $IC_{50}$ of ~2.6 μM.

Importantly, CPD 229 significantly enhances the gyrase-mediated DNA nicking and double-stranded breaks for Mtb gyrase (FIG. 48D, lanes 1-2). A likely MoA of CPD 229 is to stabilize the enzyme-DNA cleavage-complex, which leads to the DNA nicks and breaks. In other words, it is an Mtb gyrase poison.

Six analogs of CPD 229 were obtained from the NCI Developmental Therapeutics Program (dtp.cancer.gov). All except 262 potently inhibit Mtb gyrase with low micromolar $IC_{50}$s (Table 10). All of these analogs cause the Mb gyrase-mediated DNA nicking and double-strand breaks (FIG. 48D).

TABLE 10
CPD 229 series-gyrase and anti-Mtb activity profiling
| Compound # | IC50 (μM) Mtb gyrase | MIC (μM) Ec | MIC (μM) Sa | MIC (μM) Mtb | MIC (μM) Mab | IC50 (μM) HepG2 | SI Mtb/ Mab |
|---|---|---|---|---|---|---|---|
| 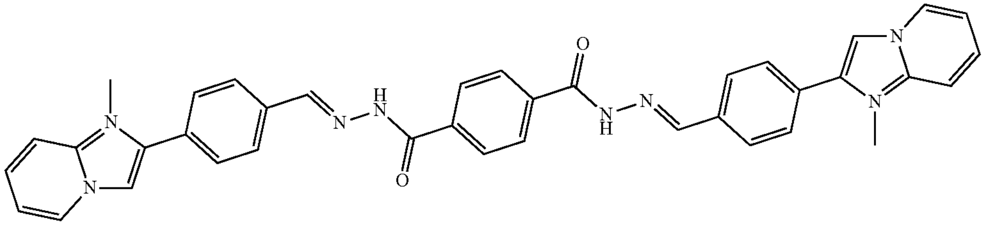 CPD229 (NSC375161) | 2.6 | 12.5 | >200 | 7.1 | 10.08 | NT | >28/ >18.5 |
| 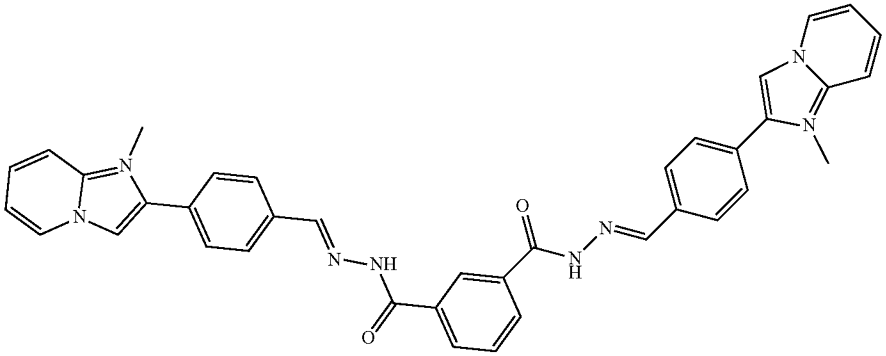 CPD259 (NSC380479) | 2.6 | >200 | 200 | NA | NA | NT | — |

TABLE 10-continued
| CPD 229 series-gyrase and anti-Mtb activity profiling | | | | | | | |
|---|---|---|---|---|---|---|---|
| Compound # | IC50 (μM) Mtb gyrase | MIC (μM) Ec | MIC (μM) Sa | MIC (μM) Mtb | MIC (μM) Mab | IC50 (μM) HepG2 | SI Mtb/ Mab |
| 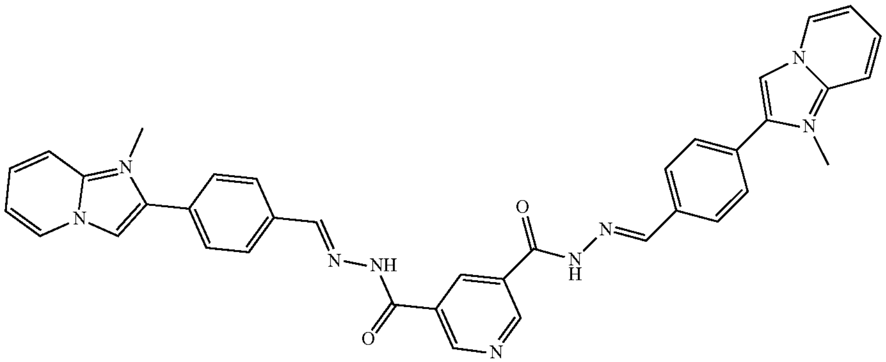 CPD260 (NSC380481) | 9.2 | >200 | >200 | >200 | >200 | NT | — |
| 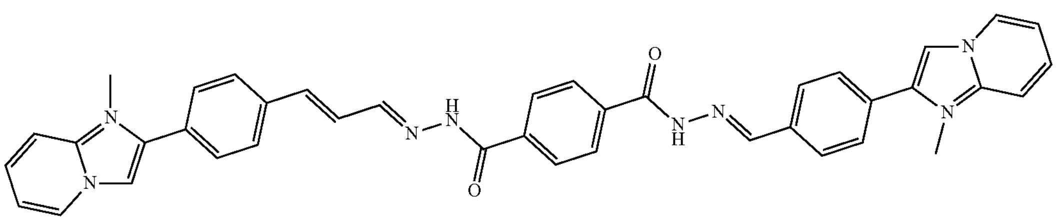 CPD261 (NSC603169) | 9.3 | 50 | >200 | 109.4 | 22.9 | NT | >1.8/ >8.7 |
| 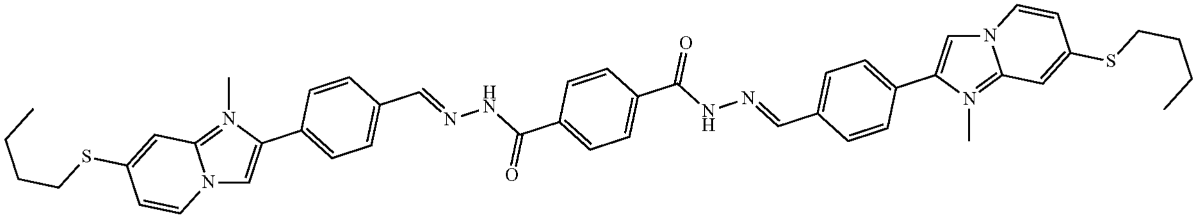 CPD262 (NSC603170) | 118 | >200 | >200 | 122 | NA | NT | >1.6/- |

TABLE 10-continued

| CPD 229 series-gyrase and anti-Mtb activity profiling | | | | | | | |
|---|---|---|---|---|---|---|---|
| Compound # | IC50 (µM) Mtb gyrase | MIC (µM) Ec | MIC (µM) Sa | MIC (µM) Mtb | MIC (µM) Mab | IC50 (µM) HepG2 | SI Mtb/ Mab |
| 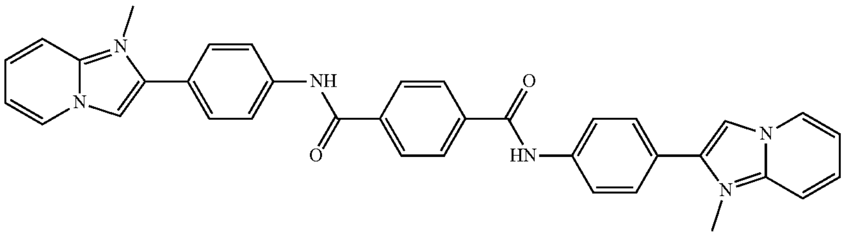 CPD263 (NSC603173) | 7.7 | 0.19 | 0.39 | 11.3 | >200 | NT | >17.7/- |
| 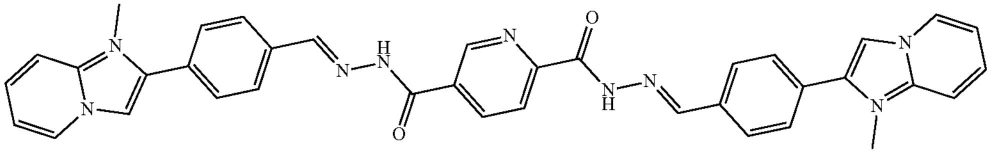 CPD264 (NSC613800) | 2.1 | 3.1 | 100 | 6.2 | 13.5 | NT | >32.3/ >15 |

>200: loss of cell viability only at highest [drug];
NT = No toxicity at higher concentration (200 µM)
SI = IC50(HepG2 toxicity)/MIC. For compounds with no toxicity at 200 µM, >## indicates minimum SI. NA represents Not Active at 200 µM.
Ec, *E. coli* strain ATCC25922.
Sa, *S. aureus* stain ATCC14775.

Noticeably, CPD 261 (FIG. 48D, lane 5) causes substantial amount of DNA nicking and nicked more than half of the DNA sample at 100 μM. Multiple CPDs in this series exhibited potent bactericidal activity against Mtb including CPDs 229, 263, and 264 with MIC=7.1, 11.3, and 6.2 μM, respectively (Table 10).

All 7 analogs were also assayed against *M. abscessus*, a notoriously drug resistant opportunistic pathogen. Intriguingly, although CPDs 229 and 264 showed comparable activity against Mab, it is noted that species-specific activity of CPD 261 against Mab and CPD 263 against Mtb attributable perhaps to differences in the gyrase enzymes or cell wall permeability. CPDs 229, 263, and 264 were also found to be active against wild type *E. coli* strain ATCC 25922 (MIC 6.25-12.5 μM) (Table 10), indicating potential as broad-spectrum antimicrobials against Gram-negative bacteria. CPD 263 is very potent against both *E. coli* strain ATCC 25922 and *S. aureus* strain ATCC 14775 with MIC in the nanomolar range (Table 10).

These 4-(1-methylimidazo[1,2-a]pyridine-1-ium CPDs offer a large therapeutic window, with no toxicity observed upon exposure of HepG2 cells to 200 μM overnight. Likewise, screening of CPDs 229, 261, and 263 against the NCI panel of 60 cancer cell lines revealed no cytotoxicity even at high concentrations (up to 1 mM; results of NCI DTP (Developmental Therapeutics Program)). CPD 229 was also well-tolerated in mice (CDF1 mice, 800 mg/kg, 100% survival for 5 days,) in NCI in vivo screening studies (results of NCI DTP). The results show that 229 does not bind to DNA tightly. It should not intercalate into DNA base pairs due to the bulky methyl group and rigid chemical structure. This indicates in vivo efficacy of this chemical series as a novel antimycobacterial agent.

Figure 49:
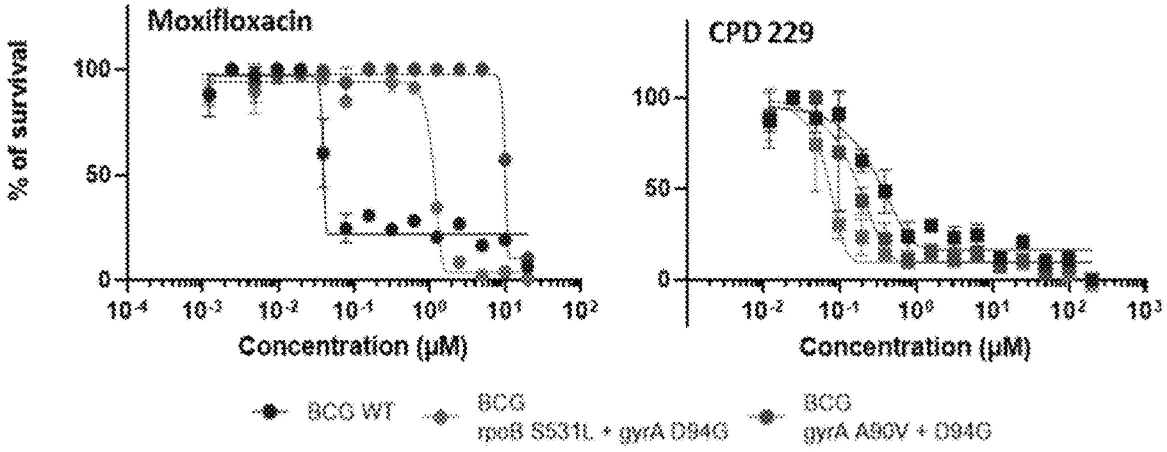
FIG. 49 shows the cross-resistance of novel anti-Mtb gyrase inhibitors with FQs. Dose response curves of MOX (FQ control) and CPD229 against wild-type BCG, $FQ^R$ BCG (with A90V/D94G double mutation in gyrA QRDR), and $FQ^R$ (D94G) $Rif^R$ (rpoB S531L). After treatment with drugs for 5 days, resazurin was added overnight before fluorescence detection (Ex-530 nm, Em-590 nm). MIC for MOX were 0.04 (WT), 1.49 ($FQ^R RIF^R$), 10.93 ($FQ^R$_double mutation). MIC for CPD229 were 0.9, 0.12, and 0.4 for the same strains, respectively.

To determine whether novel gyrase inhibitors exhibit unwanted cross-resistance with FQs, the MIC of 229 (FIG. 49) against wild-type *M bovis* BCG, $FQ^R$ BCG (with A90V/D94G double mutations), and $FQ^R$ (D94G) $Rif^R$ (rpoB S531L). The dose-response profile of MOX (FIG. 49) validates the resistance phenotypes of the strains. 229 kills $drug^R$ BCG with equal (if not slightly better) potency as wild-type, consistent with novel mechanism of gyrase inhibition and killing (FIG. 49).

Analogs of 229 can be synthesized by retaining the backbone, but varying the R groups to explore the importance of distinct pharmacophore components by varying properties, such as acidity/basicity, hydrogen bonding strength, solubility, and microsomal stability as well as mycobacterial cell wall permeability. In vitro Topo assays can serve to prioritize CPDs for optimal target inhibition and selectivity. Mtb whole-cell assays allow selection of cell wall permeable scaffolds with potent antimycobacterial activity. Cytotoxicity assays can be used to eliminate toxic CPDs. A panel of secondary assays can provide additional decision-driving data such as activity against dormant and intracellular Mtb, frequency of resistance, cross-resistance, synergy, and efflux. In vitro ADME/DMPK assays can identify optimal CPDs or highlight liabilities to be addressed in subsequent rounds of analog synthesis.

Figure 50:
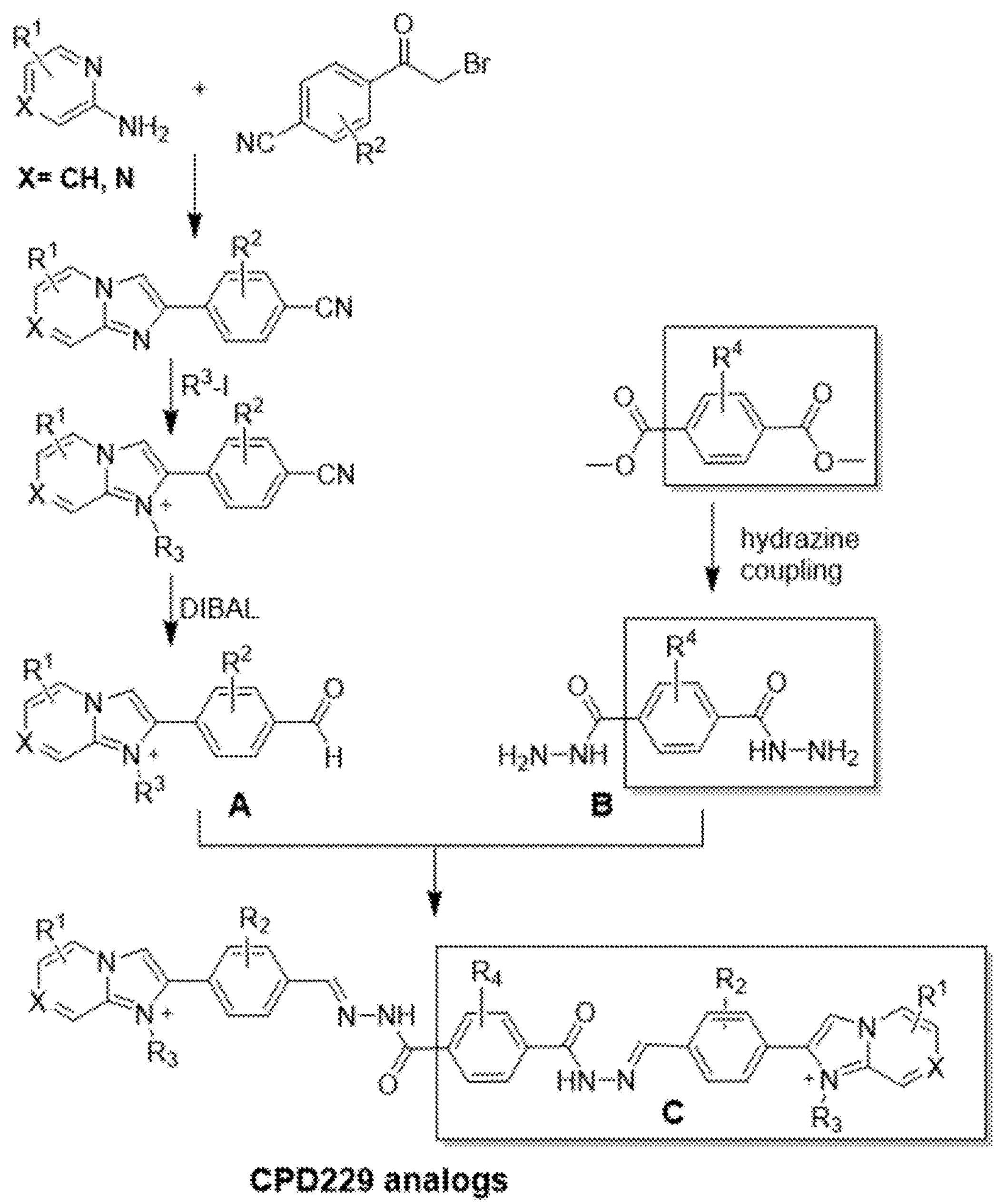
FIG. 50 shows the scheme of synthesizing 229 analogs.

The initial structure activity relationship (SAR) studies show that symmetrical 1,4-disubstituted CPDs around the arylhydrazide group are more active than the corresponding 1,3-analogs. The approach to the synthesis of 229 analogs is outlined in FIG. 50. The condensation of commercially-available substituted 2-amino pyridine, or 2-amino pyrazine CPDs with substituted 4-(2-bromoacetyl)benzonitrile derivatives can lead to the substituted 4-(imidazo[1,2-a]pyridin-2-yl)benzonitrile derivatives. Treatment with alkyl iodide will generate the corresponding N-1 alkylated analogs, which follows reduction with diisobutylaluminium hydride (DIBAL) can generate the substituted 4-formylphenyl-1-alkylylimidazo[1,2-a]pyridin-1-ium CPDs A.

The terephthalohydrazide CPDs B can be prepared by treatment of commercially-available substituted dimethyl terephthalate with hydrazine, and the final desired 229 analogs are formed following condensation of the terephthalohydrazide CPDs B with the imidazopyridin-1-ium CPDs A. Based on Mtb permeability prediction tools, building blocks can be selected to improve the solubility and Mtb permeability of the CPDs to prepare 35 to 40 analogs of 229. In parallel, the same number of truncation analogs C (FIG. 50), monomers of 229 analogs can also be prepared.

Figure 51:
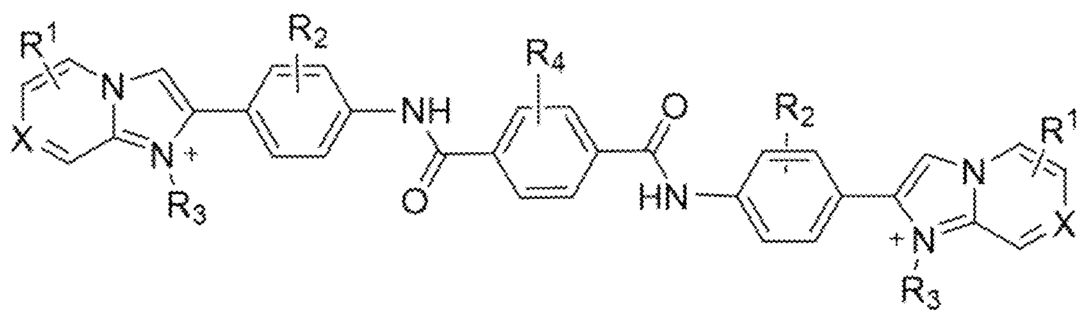
FIG. 51 shows the structure of terephthalamide analogs.

Analogs can also be prepared by replacing the terephthalohydrazide group by the terephthalamide group (FIG. 51) like CPD 263, which showed interesting activity in in vitro Mtb DNA gyrase inhibition assays and in whole cell Mtb assays with no toxicity seen at 200 PM.

In addition, analogs can further be prepared by replacing the phenyl group of the terephthalohydrazide moiety with heteroaryl groups such as, pyridine, pyrazine, furan and/or pyrimidine. The incorporation of heteroaryl group can increase the solubility and permeability of the CPD as was observed with 264.

The SAR studies can proceed sequentially. All CPDs can be first screened in gyrase inhibition assays and whole cell Mtb assays and active CPDs with improved potency can be tested in secondary Mtb assays. Modifications that increase the selectivity index can be preserved in the next round of optimization. For CPDs with excellent potency, the molecular mass (Mr), log P, and polar surface area (PSA) can be calculated, as these pharmacological properties are useful to guide optimization balancing mycobacterial permeability and oral bioavailability.

SDFQ- and Gel-based Mtb gyrase and human TopoIIα titration assays in triplicate at 10 concentrations spanning 3 log units can be used to determine the IC50 against Mtb gyrase and human TopoIIα. Only CPDs with reproducible concentration response curves will advance for further evaluation.

Metabolism, serum protein binding, and permeability/transport are good criteria to drive optimization CPDs towards the goal of oral bioavailability and long serum half-life to maximize time above MIC. In vitro ADME assays can be conducted on up to 10 analogs, with prioritization based on activity profiles from secondary assays. Using standard, well-validated assays, Eurofins Pharmacology Discovery Services will assess aqueous solubility (PBS pH 7.4, gastric fluid, intestinal fluid), partition coefficients (log D), intrinsic clearance (human hepatic microsomal stability), plasma protein binding to determine unbound fraction available for antimicrobial activity, and Caco-2 permeability (apical to basolateral transport as well as efflux).

Based on the results, lead analogs of 229 can be identified with improved potency and selectivity. 229 and analogs are Mtb gyrase poisons and show great potential. Three analogs have potent activities against Mtb whole cells and gyrase. These CPDs are not toxic to mammalian/human cells and mice at high concentrations. Additionally, 229 overcomes the FQ-resistance (FIG. 49).

Three psoralen derivatives (46, 119, and 124) are potent Mtb gyrase inhibitors and have anti-Mtb whole cell activities. They do not show toxicity upon exposure of HepG2 cells to 200 μM.

The mechanism of action (MoA) studies can be used for the development of a potent and effective drug. The MoA studies can provide important information to guide optimization efforts. Gel- and SDFQ-based titration assays can be used to confirm the selectivity of these new gyrase inhibitors for inhibition of Mtb gyrase over human Topos.

Gyrase poisoning is a preferred MoA for gyrase inhibitors and can result in bactericidal activity. For example, following treatment of *E. coli* with norfloxacin (a gyrase poison), a ~4-fold increase in the number of covalent gyrase cleavage complex per cell is sufficient for growth inhibition, and further increase of the gyrase covalent complex at >1×MIC drug concentrations correlate with >99% cell killing. The results showed that 229 and analogs are gyrase poisons that can shift the DNA cleavage-religation equilibrium to increase the level of the covalent cleavage complex. To further study the poisoning MoA of 229 and analogs, two gel-based assays can be used for this study. The first assay is a plasmid-based assay. The second assay is an oligomer-based cleavage assay.

Previous studies showed that FQ mutations mainly occurred in the QRDR of GyrA. The two most frequent mutations in GyrA are A90V and D94G. The double mutation of A90V and D94G was also identified in clinical samples and is more resistant to FQs. Three FQ GyrA mutants: A90V, D94G, and A90V D94G can be generated using site-directed mutagenesis. The GyrA mutants can be purified and reconstituted with GyrB. The inhibition of the gyrase mutants by the new gyrase inhibitors can be tested. FQs, such as moxifloxacin, can be tested as a control. The new gyrase inhibitors should efficiently inhibit these FQ-mutants. In contrast, these Mtb gyrase mutants should be resistant to moxifloxacin.

DNA binding studies of new gyrase inhibitors can be performed using UV melting, fluorescence titration, and ITC. Since small molecules tightly binding to DNA are usually toxic to human cells, gyrase inhibitors with high affinity to DNA are excluded from further development. Mtb gyrase binding can be explored by different biophysical methods including ITC, DSC, and mass spectrometry. ITC and DSC are excellent tools to investigate ligand-protein interactions and were used previously to study inhibitors binding to *E. coli* gyrase.

Molecular docking and molecular dynamics simulation of gyrase inhibitors with Mtb gyrase and mutants can be performed using structures 5BS8 (Mtb-GyrA) and 6GAU (Mtb-GyrB) for the simulations.

The in vitro target-based studies and whole cell Mtb assays should demonstrate that new gyrase inhibitors are on target and inhibit Mtb growth through inhibiting Mtb gyrase. 229 and analogs are Mtb gyrase poisons. The new gyrase inhibitors should overcome FQ-mutations.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for inhibiting a DNA gyrase, comprising contacting the DNA gyrase with a compound having a structure of formula (V):

(V)

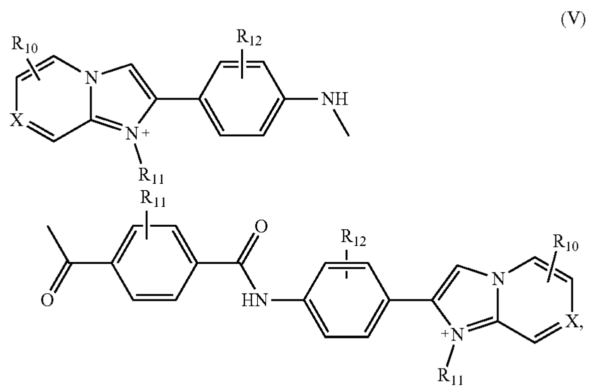

wherein X is selected from CH, CR and N; R, $R_{10}$ and $R_{12}$ are each independently selected from halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea; and $R_{11}$ is selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

2. The method of claim 1, the DNA gyrase being a *E. coli* DNA gyrase.

3. The method of claim 1, the DNA gyrase being a *S. aureus* DNA gyrase.

4. The method of claim 1, the DNA gyrase being a MRSA DNA gyrase.

5. The method of claim 1, the DNA gyrase being a *M. tuberculosis* DNA gyrase.

6. The method of claim 1, the compound being

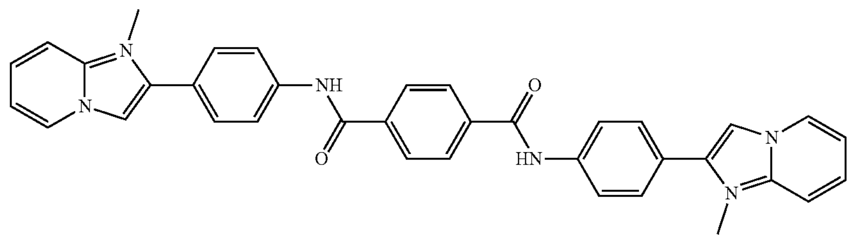

CPD263 (NSC603173)

7. A method for treating a bacterial infection in a subject, the method comprising administering to the subject in need of such treatment a pharmaceutical composition comprising a compound having a general structure of:
of formula (V)

(V)

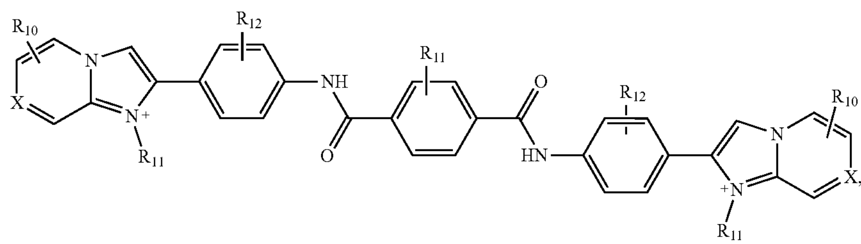

wherein X is selected from CH, CR and N; R, $R_{10}$ and $R_{12}$ are each independently selected from halogen, hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, haloalkyl, acyl, substituted acyl, alkoxyl, hydroxyl, carboxyl, carbonyl, amine, amide, ester, haloalkyl, haloaryl, thiol thioamide, urea, and thiourea; and $R_{11}$ is selected from hydrogen, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl substituted alkenyl, alkynyl, haloalkyl, acyl, substituted acyl, alkoxyl, hydroxyl, carboxyl, carbonyl, amine, amide, ester, haloalkyl, haloaryl, thiol, thioamide, urea, and thiourea.

8. The method of claim 7, the subject being an animal.

9. The method of claim 7, the bacterial infection being caused by *E. coli, S. aureus*, MRSA, *B. subtilis*, or *M. tuberculosis.*

10. The method of claim 7, said pharmaceutical composition being administered through oral, rectal, bronchial, nasal, topical, buccal, sub-lingual, transdermal, vaginal, intramuscular, intraperitoneal, intravenous, intra-arterial, intracerebral, or intraocular administration.

11. The method of claim 7, the bacterial infection being caused by *E. coli.*

12. The method of claim 7, the bacterial infection being caused by *S. aureus.*

13. The method of claim 7, the bacterial infection being caused by *M. tuberculosis.*

14. The method of claim 7, the bacterial infection being caused by MRSA.

15. The method of claim 7, the compound being

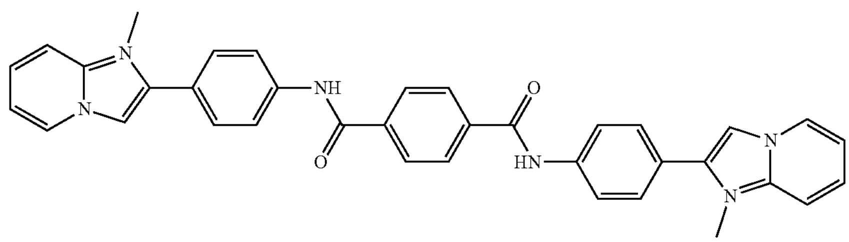

CPD263 (NSC603173)

* * * * *